(12) United States Patent
Tasler et al.

(10) Patent No.: US 10,723,743 B2
(45) Date of Patent: Jul. 28, 2020

(54) KV1.3 INHIBITORS AND THEIR MEDICAL APPLICATION

(71) Applicant: 4SC AG, Planegg-Martinsried (DE)

(72) Inventors: Stefan Tasler, Seefeld (DE); Ilga Krimmelbein, Munich (DE); Juergen Kraus, Andechs (DE); Mirko Zaja, Munich (DE)

(73) Assignee: 4SC AG, Planegg-Martinsried (DE)

( * ) Notice: Subject to any disclaimer, the term of this patent is extended or adjusted under 35 U.S.C. 154(b) by 0 days.

(21) Appl. No.: 16/274,748

(22) Filed: Feb. 13, 2019

(65) Prior Publication Data

US 2019/0185483 A1 Jun. 20, 2019

Related U.S. Application Data

(62) Division of application No. 15/557,696, filed as application No. PCT/EP2016/055451 on Mar. 14, 2016.

(30) Foreign Application Priority Data

Mar. 13, 2015 (EP) .................................. 15159080

(51) Int. Cl.
| | |
|---|---|
| *C07D 491/153* | (2006.01) |
| *C07D 493/04* | (2006.01) |
| *C07D 495/04* | (2006.01) |
| *C07D 498/04* | (2006.01) |
| *A61K 31/4741* | (2006.01) |
| *C07D 495/14* | (2006.01) |
| *C07D 498/14* | (2006.01) |

(52) U.S. Cl.
CPC ........ *C07D 493/04* (2013.01); *A61K 31/4741* (2013.01); *C07D 491/153* (2013.01); *C07D 495/04* (2013.01); *C07D 495/14* (2013.01); *C07D 498/04* (2013.01); *C07D 498/14* (2013.01)

(58) Field of Classification Search
CPC .................................................. C07D 491/153
See application file for complete search history.

(56) References Cited

PUBLICATIONS

International Search Report for PCT/EP2016/055451 dated May 6, 2016.
Wernekenschnieder, A. et al., "3-Alkyl- and 3-aryl-7H-furo[3,2-g]chromen-7-ones as blockers of the voltage gated potassium channel KV1.3" Die Pharmazie, Govi Verlag Pharmazeutischer Verlag GMBH, Apr. 1, 2004, vol. 59, No. 4, pp. 319-320.
Wulff, H. et al., "Alkoxypsoralens, Novel Nonpeptide Blockers of Shaker-Type K+ Channels: Synthesis and Photoreactivity," J. Med. Chem., 1998, vol. 41, pp. 4542-4549.
Kum, N. H. Pardanani et al., "Studies in the Synthesis of Coumarino-alpha-pyrones and Furocoumarins Part IV. Synthesis of Alkyl-psoralenes," Journal Indian Chem Soc, 1959, vol. 46, No. 11.
Garazd, M. M. et al., "Modified Coumarins. I. Synthesis of 5-Phenyl-7H-Furo[2,3-g]Chromen-7-ones and 9-phenyl-7H-Furo-[2,3-f]chromen-7-ones," Chemistry of Natural Compounds, 2000, vol. 36, No. 5, pp. 478-484.

*Primary Examiner* — Brian E McDowell
(74) *Attorney, Agent, or Firm* — Millen White Zelano and Branigan, PC; Csaba Henter

(57) ABSTRACT

Compounds of formula (II) or a pharmaceutically acceptable salt or solvate thereof, the medical uses thereof for diseases or medical conditions where the inhibition of the voltage-gated potassium channel Kv1.3 is beneficial, and methods for their preparation.

16 Claims, 1 Drawing Sheet

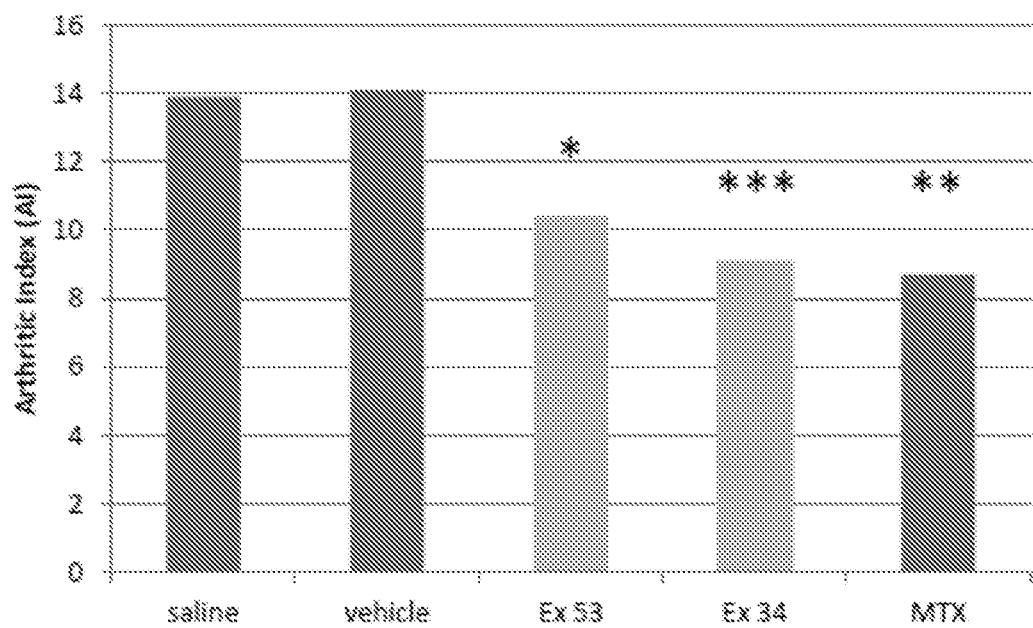

KV1.3 INHIBITORS AND THEIR MEDICAL APPLICATION

The present invention relates to inhibitors of the voltage-gated potassium channel Kv1.3, and their application for the treatment of conditions in which Kv1.3 activity contributes to the disease state, in particular for those mediated by activated effector memory T-cells.

BACKGROUND OF THE INVENTION

Voltage-gated potassium channels constitute the major ionic conductance detected in both excitable and non-excitable cells and are important players in cellular processes like regulation of ion balance, membrane potential, secretion and cell excitability (Lan et al., Cancer Biol. Ther. 2005, 4, 1342). Such events can mediate or trigger certain signaling cascades, resulting in cellular processes of great diversity.

Certain cells of the immune system, for example, require a complex interplay of different ion channels in order to convert a pathogenic stimulus into an appropriate action like proliferation and/or cytokine secretion. Especially in T- and B-lymphocytes, this type of activation triggers a calcium signal within the cell, which has to be maintained for an extended period in order to result in transcriptional activity and thus a completion of the activation program. For T-cells, the activation via the T-cell receptor (TCR) triggers a signaling cascade resulting in the calcium release from the endoplasmatic reticulum into the cytosol. This release triggers the opening of the CRAC ($Ca^{2+}$-release activated channel), enabling a strong calcium influx into the cell. For maintaining such a calcium influx for an extended period of time, which is required for an efficient T-cell response on a cellular level, potassium has to be released from the cytosol. For this purpose, T-cells are equipped with two potassium channels, the KCa3.1(IK-1), which is calcium-gated and thus opens upon increasing cytosolic calcium concentrations, and Kv1.3, which is voltage-gated and opens due to the depolarization of the membrane potential caused by the calcium influx. Both act together for potassium efflux, now allowing for further calcium influx via CRAC into the cell. This interplay of CRAC, IK-1 and Kv1.3 is crucial for an activation of lymphocytes to result in proliferation and/or cytokine production (Lewis, Annu. Rev. Immunol. 2001, 19, 497; Vig et al., Nat. Immunol. 2009, 10, 21; Feske et al., Nat. Rev. Immunol. 2012, 12, 532).

Different T- and B-cell subsets display different expression numbers of IK-1 and Kv1.3, of which class-switched memory B-cells and repeatedly activated effector memory T-cells ($T_{EM}$ cells; $CD4^+$ T-cells and $CD8^+$ T-cells) are dominated by Kv1.3. These lymphocyte subsets are of the $Kv1.3^{high}IK-1^{low}$ phenotype, in which Kv1.3 expression numbers of 1000 to 2900 channels per cell were found, whereas IK-1 channel numbers in these cells are clearly below 100. In contrast, other activated T- and B-cell subsets display rather similar expression numbers for Kv1.3 and IK-1 of several hundred per cell each, and in some instances even with a favour of IK-1 (for further information see the review articles listed below).

Inhibition of Kv1.3 is thus effective in decreasing lymphocyte proliferation and/or cytokine production in lymphocytes of the $Kv1.3^{high}IK-1^{low}$ phenotype, whereas other lymphocyte subsets are expected not to respond significantly (for further information see the review articles listed in the following paragraph and Shah et al., Cell. Immunol. 2003, 22, 100).

Several review articles deal with Kv1.3 channel architecture, distribution in human tissues and cell types and the pharmacological potential in its inhibition to treat diseases, including: Wulff et al., Chem. Rev. 2008, 108, 1744; Lam et al., Drug Dev. Res. 2011, 72, 573; Wang et al., Pharmacother. 2013, 33, 515.

$T_{EM}$ cells of the $Kv1.3^{high}IK-1^{low}$ phenotype have been postulated to be the crucial subset of disease-mediating lymphocytes in T-cell driven autoimmune disorders (for further information see the review articles listed in the preceding paragraph). This has been directly demonstrated within isolates from human patients with, e.g., Type 1 diabetes (T1D; PNAS 2006, 103, 17414), rheumatoid arthritis (RA; PNAS 2006, 103, 17414), multiple sclerosis (MS; J. Clin. Invest. 2003, 111, 1703; PNAS 2005, 102, 11094), psoriasis and psoriatic arthritis (J. Invest. Dermatol. 2011, 131, 118; J. Autoimmunity 2014, 55, 63), and anti-glomerular basement membrane glomerulonephritis (Am. J. Physiol. Renal Physiol. 2010, 299, F1258). In PBMCs isolated from patients with acute coronary syndrome (ACS), the number of $CD4^+CD28^{null}$ T-cells was significantly higher than in healthy controls and directly correlated with hs-CRP levels in these patients. This disease relevant T-cell subset significantly overexpressed Kv1.3 in these patients (Huang et al., J. Geriatric Cardiol. 2010, 7, 40) and was identified to consist mainly of $T_{EM}$ cells (Xu et al., Clin. Immunol. 2012, 142, 209). Within induced sputum form asthma patiens, increased levels of $T_{EM}$ cells were identified, being of the Kv1.3high phenotype (Koshy et al., J. Biol. Chem. 2014, 289, 12623).

$T_{EM}$ cells have also been reported to be important contributors to disease development and/or progression in chronic diseases like anti-neutrophil cytoplasmic autoantibody (ANCA) associated vasculitis (AAV; Abdulahad et al., Arthritis Res. Ther. 2011, 13, 236; Wilde et al., Arthritis Res. Ther. 2010, 12, 204), systemic lupus erythematosus (SLE; Dolff et al., Ann. Rheum. Dis. 2010, 69, 2034), Graft-versus-Host disease (Yamashita et al., Blood 2004, 103, 3986; Zhang et al., J. Immunol. 2005, 174, 3051; Beeton et al., Neuroscientist 2005, 11, 550), Inflammatory Bowel Diseases (IBDs; Kanai et al., Am. J. Physiol. Gastrointest. Liver Physiol. 2006, 290, G1051) including Crohn's disease (de Tena et al., J. Clin. Immunol. 2004, 24, 185; Beeton et al., Neuroscientist 2005, 11, 550), autoimmune thyroiditis and Hashimoto disease (Seddon et al., J. Exp. Med. 1999, 189, 279; Beeton et al., Neuroscientist 2005, 11, 550), Uveitis including pars planitis (Pedroza-Seres et al., Br. J. Ophthalmol. 2007, 91, 1393; Oh et al., J. Immunol. 2011, 187, 3338; Beeton et al., Neuroscientist 2005, 11, 550), alopecia areata (Gilhar et al., J. Invest. Dermatol. 2013, 133, 2088), vitiligo, pemphigus foliaceus, inclusion body myositis, dermatomyositis, and scleroderma (Beeton et al., Neuroscientist 2005, 11, 550). Furthermore, the important role of class-switched memory B-cells for disease pathogenesis has also been described for T1D, RA and MS (Wulff et al., J. Immunol. 2004, 173, 776), Grave and Hashimoto disease, and Sjögren syndrome (Beeton et al., Neuroscientist 2005, 11, 550). In addition, Kv1.3 inhibitors have been reported to inhibit $CD8^+$ $T_{EM}/T_{EMRA}$ cell differentiation and proliferation and their Granzyme B release, and linked to a reduction of their neurotoxicity and thus to a potential treatment of neuroinflammatory disorders like MS (Wang et al., PLoS One 2012, 7, e43950; Hu et al., PLoS One 2013, 8, e54267).

Furthermore, Kv1.3 has been identified in other cell types of the immune system like macrophages (DeCoursey et al., J. Membrane Biol. 1996, 152, 141; Villalonga et al., Biochem. Biophys. Res. Commun. 2007, 352, 913), microglia (Eder, Am. J. Physiol. Cell Physiol. 1998, 275, C327; Menteyne et al., PLoS One 2009, 4, e6770; Pannasch et al., Mol. Cell. Neurosci. 2006, 33, 401), dendritic cells (Zsiros et al., J. Immunol. 2009, 183, 4483), non-adherent natural killer cells (Koshy et al., PLoS One 2013, 8, e76740), in cells of the CNS like human neural progenitor cells (Wang et al., J. Neurosci. 2010, 30, 5020; Peng et al., J. Neurosci. 2010, 30, 10609), postganglionic sympathetic neurons (Doczi et al., Am. J. Physiol. Regul. Integr. Comp. Physiol. 2008, 295, 733), select central and peripheral neurons, neurons in the nucleus of the solitary tract (Ramirez-Navarro et al., J. Neurophysiol. 2011, 105, 2772), and oligodendrocytes (Tegla et al., Exp. Mol. Pathol. 2011, 91, 335.). With regard to microglia, their neurotoxic effect upon activation with either HIV-1 glycoprotein gp120 or HIV-1 Tat protein was abrogated upon treatment with Kv1.3 inhibitors, which underlines their potential for therapy of HIV-1-associated neurocognitive disorders (HAND) and other inflammation-mediated neurological disorders (Liu et al., Cell Death Dis. 2012, 3, e254; and PLoS One 2013, 8, e64904). Furthermore, priming of microglia by amyloid-β resulting in reactive oxygen species (ROS) production upon secondary stimulation was inhibited by treatment with Kv1.3 inhibitors, thus rendering Kv1.3 channels potential targets to reduce microglia-induced oxidative stress in Alzheimer's disease (Schilling et al., J. Cell. Physiol. 2011, 226, 3295). Furthermore, Kv1.3 inhibition was shown to decrease microglia migration (Nutile-McMenemy et al., J. Neurochem. 2007, 103, 2035). Concerning macrophages, Kv1.3 inhibitors were shown to e.g. modulate cholesterol-metabolism-associated molecules thus inhibiting macrophages' differentiation into foam cells, which represents a strategy for the treatment of atherosclerosis (also known as arteriosclerotic vascular disease or ASVD) (Yang et al., J. Lipid Res. 2013, 54, 34).

Kv1.3 has also been identified in retinal ganglion cells (Koeberle et al., Cell Death Diff. 2010, 17, 134), platelets and megakaryocytes (McCloskey et al., J. Physiol. 2010, 588, 1399; Emerson, J. Physiol. 2010, 588, 1809), and tumorigenic human mammary epithelial cells (Jang et al., BMB reports 2009, 42, 535), human ovarian cancer cells like SKOV3 (Weng et al., Prog. Mod. Biomed. 2011, 11, 2053), human lung adenocarcinoma cells A549 (Jang et al., Eur. J. Pharmacol. 2011, 651, 26), brown adipose tissue and hepatocytes (Upadhyay et al., PNAS 2013, 110, E2239) and skeletal muscle cell lines (Hamilton et al., J. Physiol. Sci. 2014, 64, 13). In addition, Kv1.3 was reported to represent a potential sensor of metabolism within the olfactory bulb (Fadool et al., PLoS One 2011, 6, e24921; Tucker et al., J. Physiol. 2013, 10, 2541 and J. Neuroendocrinol. 2012, 24, 1087). Furthermore, Kv1.3 was identified in the inner membrane of mitochondria, where they are involved in the intrinsic apoptosis pathway, and their inhibition was evaluated for the treatment of chronic lymphocytic leukemia (B-CLL) (Leanza et al., Leukemia 2013, 27, 1782), osteosarcoma, neuroblastoma and melanoma (Leanza et al., EMBO Mol. Med. 2012, 4, 577; Wu et al., Int. J. Mol. Sci. 2013, 14, 19245; Leanza et al., Curr. Pharmaceut. Design 2014, 20, 189), and suggested for the depletion of tumor-associated macrophages (Leanza et al., Curr. Med. Chem. 2012, 19, 5394). Inhibitors of Kv1.3 were also shown to potently suppress migration and proliferation of vascular smooth muscle cells, which might represent a new principle for the treatment of restenosis/neointimal hyperplasia (Jackson, Arterioscler. Thromb. Vasc. Biol. 2010, 30, 1073; Cheong et al., Cardiovasc. Res. 2011, 89, 282; Olschewski, Cardiovasc. Res. 2011, 89, 255; Cidad et al., Arterioscler. Thromb. Vasc. Biol. 2012, 32, 1299; Ishii et al., Free Rad. Biol. Med. 2013, 65, 102; Cidad et al., Pflugers Arch. Eur. J. Physiol.; DOI 10.1007/s00424-014-1607-y).

Kv1.3 expression has also been shown to be a potential disease marker in biopsies of inflamed mucosa from ulcerative colitis patients and correlated with certain cytokine expression levels (Hansen et al., J. Crohn's Col. 2014, 8, 1378).

A Kv1.3 inhibitor has been shown to decrease activation levels of Th2-cells and cytotoxic $CD8^+$ T-cells in PBMCs from patients with acute ischemic stroke (AIS), potentially reducing its unwanted clinical consequences (Folyovich et al., CNS Neurol. Diorders Drug Targets 2014, 13, 801).

For $CD4^+$ T lymphocytes from PBMCs isolated from patients with essential hypertension, a chronic low-grade inflammatory disease, increased Kv1.3 expression levels compared to undiseased control group were reported (Li, Exp. Clin. Cardiol. 2014, 20, 5870).

Efficacy of Kv1.3 inhibitors has been reported in relevant animal models for autoimmune diseases like Psoriasis, MS, alopecia areata, rheumatoid arthritis, type I diabetes, allergic and irritant contact dermatitis (Azam et al., J. Invest. Dermatol. 2007, 127, 1419; Ueyama et al., Clin. Experiment. Dermatol. 2013, 38, 897; Kundu-Raychaudhuri et al., J. Autoimmunity 2014, 55, 63), anti-glomerular basement membrane glomerulonephritis (as a cause of rapidly progressive glomerulonephritis), and also for asthma, chronic kidney disease, renal fibrosis in chronic renal failure and end-stage renal disease (Kazama, J. Physiol. Sci. 2015, 65, 25; Kazama et al., Int. J. Nephrol. 2012, article ID 581581), and for melanoma, obesity, insulin resistance, and neuroprotection and neurorestoration (Peng et al., Neuro-Oncology 2014, 16, 528). A Kv1.3 inhibitor was reported to reduce tumor volume in a xenograft model using the human lung adenocarcinoma cells A549 (Jang et al., Eur. J. Pharmacol. 2011, 651, 26), and to decrease intimal hyperplasia formation, indicating a therapeutic potential against restenosis (Cidad et al., Cardiovasc. Drugs Ther. 2014, 28, 501). Kv1.3 inhibition prevented plaque formation and decreased exocytosis of cytoplasmic granules from $CD4^+CD28^{null}$ T-cells in a rat model for artherosclerosis, revealing a potential for suppression of the development of atherosclerosis and prevention of acute coronary syndrome (Wu et al., Heart Vessels 2015, 30, 108).

A combination of an IK-1 inhibitor and a Kv1.3 inhibitor has been shown to be effective in preventing transplant rejection in an animal model (Grgic et al., Transplant. Proc. 2009, 41, 2601). A similar effect was reported for the Kv1.3 inhibitor Correolide C within a vascularized composite allotransplantation (VCA) model (Hautz et al., Transplant. Int. 2013, 26, 552). Kv1.3 inhibition has also been shown to be effective in preventing T-cell mediated inflammatory bone resorption disease (Valverde et al., J. Bone Miner. Res. 2004, 19, 155).

Certain small molecule Kv1.3 inhibitors have been reported. For a brief overview, cf. Wulff et al., Chem. Rev. 2008, 108, 1744; and Wulff et al., Nat. Rev. Drug Disc. 2009, 8, 982. Furthermore, certain compounds were published as Kv1.3 inhibitors, belonging to scaffolds like sulfonamides (WO2011/073269, WO2011/073273, WO2011/073277, WO2010/130638, WO2010/023448), spiro compounds (WO2010/066840), pyrazoles and imidazoles (WO2007/020286), dioxidobenzothiazols (Haffner et al., Bioorg. Med. Chem. Lett. 2010, 20, 6983 and 6989; WO2005/11304), and phenanthridines (Pegoraro et al., Bioorg. Med. Chem. Lett. 2009, 19, 2299 and 2011, 21, 5647).

Out of this set of compounds, especially certain khellinones (Baell et al., J. Med. Chem. 2004, 47, 2326; Harvey et al., J. Med. Chem. 2006, 49, 1433; Cianci et al., Bioorg. Med. Chem. Lett. 2008, 18, 2055; WO03/078416; WO2006/096911; WO2008/040057; WO2008/040058; WO2009/043117; WO2009/149508) and the psoralen derivative PAP-1 (Vennekamp et al., Mol. Pharmacol. 2004, 65, 1364; Schmitz et al., Mol. Pharmacol. 2005, 68, 1254; Bodendiek et al., Eur. J. Med. Chem. 2009, 44, 1838; WO2006/041800; U.S. Pat. No. 7,772,408) have been evaluated with regard to their potential as Kv1.3 inhibitors.

Furthermore, certain Kv1.3 inhibitors have been described in the field of cardiovascular pathologies, particularly in the field of diseases derived from hyperplasia of the tunica intima (WO2010/040803) and for application in neurodegenerative diseases, in particular for neuroprotection and stimulation of neural growth (WO2007/139771) and reduction of microglia-mediated neurotoxicity (WO2012/170917). Kv1.3 inhibitors have also been reported to affect weight control, control of body fat and food intake and thus for treating obesity, diabetes and insulin insensitivity (WO2002/100248). Furthermore, a combination treatment of a Kv1.3 inhibitor with a pre-implantation factor peptide for the treatment of intracellular damage resulting from e.g. Lyme disease, cardiovascular disease, duodenal peptic ulcer, atherosclerosis or tuberculosis was described (WO2012/119072). WO2013/052507 describes targeting the Kv1.3 channel as a treatment for obesity and obesity-related disorders.

Syntheses of certain 5-phenyl-furo[3,2-g]coumarin (that is 4-phenyl-psoralen) derivatives have been described in the literature, usually involving a Pechmann cyclization and a McLeod's reaction. Cf. for example Ansary, Bull. Fac. Pharm. Cairo Univ. 1998, 36, 85; Garazd et al., Chem. Nat. Comp. 2000, 36, 478; Garazd et al., Chem. Nat. Comp. 2002, 38, 539; Traven et al., Heterocyclic Commun. 1997, 3, 339; Pardanani et al., J. Ind. Chem. Soc. 1969, 46, 1014. A specific route for inverting the anellation order of the lacton-ring and the furan is described in Kawase et al., Bull. Chem. Soc. Jpn. 1978, 51, 1907-1908; Zhang et al., Eur. J. Med. Chem. 2010, 45, 5258. A synthetic route towards certain furo[3,2-g]quinolin-7(8H)-one, thieno[3,2-g]coumarin, 6H-chromeno[6,7-d]oxazol-6-one (i.e. oxazolocoumarin) and 8-azapsoralen derivatives is described in Guiotto et al., Il Farmaco 1995, 50, 479; Chilin et al., Gazz. Chim. Ital. 1988, 118, 513, and Rodighiero et al., J. Heterocyclic Chem. 1998, 35, 847, however, these compounds were all equipped only with methyl substituents.

Certain specific psoralens, and xanthotoxin in particular, have been described for their potential photobiological activities and for their use in photochemotherapy (PUVA=psoralen+UVA irradiation) (Pathak et al., J. Invest. Dermatol. 1959, 32, 255; Juettermann et al., Farmaco, Edizione Scientifica 1985, 40, 3; Toth et al., J. Photochem. Photobiol. B Biol. 1988, 2, 209; Nofal et al., Pakistan J. Scientific Ind. Res. 1990, 33, 148; Tuveson et al., Photochem. Photobiol. 1992, 56, 341; Becker et al., J. Chem. Soc. Faraday Trans. 1993, 89, 1007; Körner, Arch. Pharm. Med. Chem. 2002, 5, 187). Such investigations have also been performed for certain 5-phenyl-furo[3,2-g]coumarin (that is 4-phenyl-psoralen) derivatives: Farag, Eur. J. Med. Chem. 2009, 44, 18; Lown et al., Bioorg. Chem. 1978, 7, 85; Ansary, Bull. Fac. Pharm. Cairo Univ. 1998, 36, 85. For specific linear furo[3,2-g]quinolone, thieno[3,2-g]coumarin, 8-azapsoralen and thieno-[3,2-g]-8-aza-coumarin derivatives, such a photobiological effect has also been investigated: Guiotto et al., J. Heterocyclic Chem. 1989, 26, 917; Guiotto et al., Il Farmaco 1995, 50, 479; Aubin et al., J. Invest. Dermatol. 1991, 97, 50 and 995; Vedaldi et al., Il Farmaco 1991, 46, 1407.

Furthermore, certain 5-phenyl-furo[3,2-g]coumarins are reported to have potential in treating or preventing diseases caused or mediated by *Helicobacter pylori* (CN102091067, Zhang et al., Eur. J. Med. Chem. 2010, 45, 5258), in treating diabetes mellitus and complicating diseases thereof (CN101307056), for controlling coccids (JP63057590), and as inhibitors of NFkB and its functions in cystic fibrosis (Piccagli et al., Bioorg. Med. Chem. 2010, 18, 8341).

With regard to furoquinolones, certain biological activities have only been reported for 4-methylbenzofuro[3,2-g]quinolin-2(1H)-one: As inhibitor of FKBP52-enhanced steroid receptor activity (WO2011/034834), as inhibitor of ABCG2 protein for a method of enhancing treatment of tumor cells with a chemotherapeutic agent (WO2009/061770), and to stimulate or inhibit the binding to and lipid movements mediated by SR-BI and redirect uptake and metabolism of lipids and cholesterol by cells (WO2004/032716).

With regard to the treatment of inflammatory diseases driven by repeatedly activated $T_{EM}$ cells, especially autoimmune diseases, general immunosuppressants are utilized in currently applied treatment regimens (e.g. mycophenolate mofetil, cyclophosphamide, cyclosporine A, azathioprine, etc.) resulting in a general suppression of lymphocytes, thus increasing the risk for opportunistic infections. Furthermore, longterm treatment often results in side effects reducing the overall compliance (e.g. skin atrophy and enhanced risk of osteoporosis with glucocorticoid treatment, increased risk of skin cancer and rhabdomyolysis upon topical tacrolimus treatment, nausea and vomitting with cyclophosphamide and cyclosporine A). Recent approvals of medicaments for the treatment of such diseases include several biologics (e.g. Alefacept, Natalizumab, Adalimumab, Ustekinumab, Belimumab), which display a potential for a general side effect profile known for such drugs like sensitization, anaphylactic shock, resistance, and again often showed an enhanced risk for opportunistic infections.

There is, therefore, a need for new small molecule medicaments which, compared with the aforementioned therapeutics, are particularly more selective towards specific cell subsets of the immune system and particularly avoid the aforementioned adverse effects, in particular in the therapy of the above medical conditions.

DETAILED DESCRIPTION OF THE INVENTION

It has now been found that such a small molecule medicament can be represented by Kv1.3 inhibitors, which, compared with the aforementioned therapeutics, are particularly more selective towards $Kv1.3^{high}$ phenotype cells, particularly class-switched memory B-cells and/or effector memory T-cells which are of the $Kv1.3^{high}$ phenotype, and particularly avoid the aforementioned adverse effects, in particular in the therapy of the above medical conditions.

Embodiments of the present invention are detailed in the following items:

1. A compound of the general formula (II) or a salt or solvate thereof,

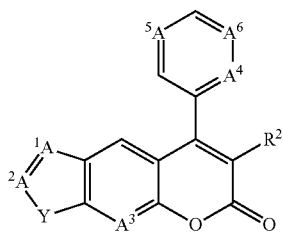

wherein
$A^1$ is selected from the group consisting of N and C—$R^8$;
$A^2$ is selected from the group consisting of N and C—$R^3$;
$A^3$ is selected from the group consisting of N and C—$R^9$;
$A^4$ and $A^5$ and $A^6$ are independently selected from the group consisting of N and C—$R^1$;
$R^1$ is selected from the group consisting of hydrogen, ($C_1$-$C_3$)alkyl, halogen, ($C_1$-$C_3$)alkoxy, and ($C_1$-$C_3$)haloalkyl;
$R^2$ is selected from the group consisting of hydrogen, halogen, and ($C_1$-$C_3$)alkyl;
$R^3$ is selected from the group consisting of hydrogen, ($C_1$-$C_3$)alkyl, $NR^4R^5$, ($C_1$-$C_3$)alkyl-$NR^4R^5$, and cyano, wherein $R^4$ and $R^5$ are independently selected from the group consisting of hydrogen, ($C_3$-$C_5$)cycloalkyl, ($C_3$-$C_5$)heterocycloalkyl and ($C_1$-$C_3$)alkyl, or $R^4$ and $R^5$ together with the nitrogen atom to which they are attached form a 5- to 7-membered heterocyclic ring optionally comprising in addition to the aforementioned nitrogen atom a further heteroatom group selected from the group consisting of O and $NR^6$, wherein $R^6$ is selected from the group consisting of hydrogen, methyl, acetyl and formyl;
Y is selected from the group consisting of O and S;
$R^8$ is selected from the group consisting of ($C_1$-$C_4$)alkyl, ($C_3$-$C_5$)cycloalkyl and ($C_3$-$C_5$)heterocycloalkyl; and
$R^9$ is selected from the group consisting of hydrogen, ($C_1$-$C_3$)alkyl and ($C_1$-$C_3$)alkoxy;
with the proviso that the following compounds are excluded:
3-methyl-5-phenyl-7H-furo[3,2-g]chromen-7-one, 2,3,9-trimethyl-5-phenyl-7H-furo[3,2-g]chromen-7-one, 3,9-dimethyl-5-phenyl-7H-furo[3,2-g]chromen-7-one, 2,3-dimethyl-5-phenyl-7H-furo[3,2-g]chromen-7-one, 3-ethyl-9-methyl-5-phenyl-7H-furo[3,2-g]chromen-7-one, 3-(tert-butyl)-5-phenyl-7H-furo[3,2-g]chromen-7-one, 3-(tert-butyl)-9-methyl-5-phenyl-7H-furo[3,2-g]chromen-7-one, and 2-methyl-8-phenyl-6H-chromeno[6,7-d]oxazol-6-one.

2. A compound according to item 1 or a salt or solvate thereof, wherein
$R^1$ is selected from the group consisting of hydrogen, methyl, chloro, fluoro, methoxy, ethoxy and trifluoromethyl;
$R^2$ is selected from the group consisting of hydrogen, bromo and methyl;
$R^3$ is selected from the group consisting of hydrogen, methyl, morpholinyl, morpholinomethyl, N-methylaminomethyl, N,N-dimethylaminomethyl and cyano;
$R^8$ is selected from the group consisting of methyl, ethyl and cyclopropyl; and
$R^9$ is selected from the group consisting of hydrogen, methyl and methoxy.

3. A compound according to item 1 or 2 or a salt or solvate thereof, wherein $R^2$ is selected from the group consisting of hydrogen and methyl; and $R^3$ is selected from the group consisting of hydrogen, morpholinyl, morpholinomethyl, N,N-dimethylaminomethyl and cyano.

4. A compound according to any of items 1 to 3 or a salt or solvate thereof, wherein Y is S, or Y is O, and if Y is O, at least one of $A^1$, $A^2$ or $A^3$ is N.

5. A compound according to any of items 1 to 3 or a salt or solvate thereof, wherein $A^1$ is C—$R^8$; $A^2$ is C—$R^3$; $A^3$ is C—$R^9$; and Y is O.

6. A compound according to any of items 1 to 5 or a salt or solvate thereof, wherein at least one of the following conditions is fulfilled: 1) $R^2$ is halogen, 2) $R^3$ is selected from the group consisting of $NR^4R^5$ and cyano, 3) $A^4$ or $A^5$ or $A^6$ is N.

7. A compound according to any of items 1 to 6 or a salt or solvate thereof, wherein one of $A^4$ and $A^5$ and $A^6$ is N and the others are selected from the group consisting of N and C—$R^1$.

8. A compound according to any of items 1 to 7 or a salt or solvate thereof, wherein $R^8$ is methyl; $R^9$ is methyl; $R^1$ is selected from the group consisting of hydrogen and methoxy; $R^2$ is selected from the group consisting of hydrogen and methyl; and $R^3$ is selected from the group consisting of hydrogen, methyl and N-methylaminomethyl.

9. A compound according to item 1, which is selected from the group consisting of the compounds listed as examples of the present invention in Table 1 or a salt or solvate thereof.

10. A pharmaceutical composition comprising a compound according to any of items 1 to 9 and a pharmaceutically acceptable carrier or diluent.

11. A compound according to any of items 1 to 9 for use in the treatment of diseases or medical conditions.

12. Use of a compound according to any of items 1 to 9 for the manufacture of a pharmaceutical composition for treating diseases or medical conditions.

13. The compound according to item 10 or the use according to item 11, wherein said disease or medical condition is a disease or medical condition wherein the inhibition of the voltage-gated potassium channel Kv1.3 is beneficial.

14. The compound or use according to item 13, wherein said disease or medical condition is selected from the group consisting of psoriasis, psoriatric arthritis, autoimmune thyroiditis, Hashimoto's disease, Grave's disease, rheumatoid arthritis, vitiligo, Crohn's disease, ulcerative colitis, inflammatory bowel disease, ankylosing spondylitis (Morbus Bechterew), periodontal disease, diabetes type I, multiple sclerosis, systemic lupus erythematosus, anti-glomerular basement membrane glomerulonephritis, rapidly progressive glomerulonephritis, advanced chronic renal failure, chronic kidney disease, renal fibrosis, uveitis, pars planitis, asthma, pemphigus foliaceus, inclusion body myositis, dermatomyositis, scleroderma, Behcet disease, atopic dermatitis, allergic and irritant contact dermatitis, Lichen planus, Sjögren's syndrome, Graft-versus-Host-Reaction, Host-versus-Graft-Reaction, transplant rejection, end-stage renal disease, vascularized composite allotransplantation rejection, alopecia areata, inflammatory bone resorption disease, anti-neutrophil cytoplasmic autoantibody-associated vasculitis, osteoarthritis, diseases associated with intimal hyperplasia, breast cancer, leukemia, chronic lymphocytic leukemia, human lung adenocarcinoma, cutaneous T-cell lymphoma, osteosarcoma, neuroblastoma, ovarian cancer and melanoma, neuroinflammatory disorders, neurodegeneration, HIV-1-associated neurocognitive disorders (HAND), microglia-induced oxidative stress in Alzheimer's disease, obesity, and insulin resistance, restenosis/neointimal hyperplasia, atherosclerosis (arteriosclerotic vascular disease or ASVD), acute coronary syndrome, acute ischemic stroke, hypertension.

15. A method for producing a compound according to item 1, wherein $A^1$ is C—$R^8$ and $A^2$ is selected from the group consisting of CH and N; and wherein said method is characterized by the following conversion:

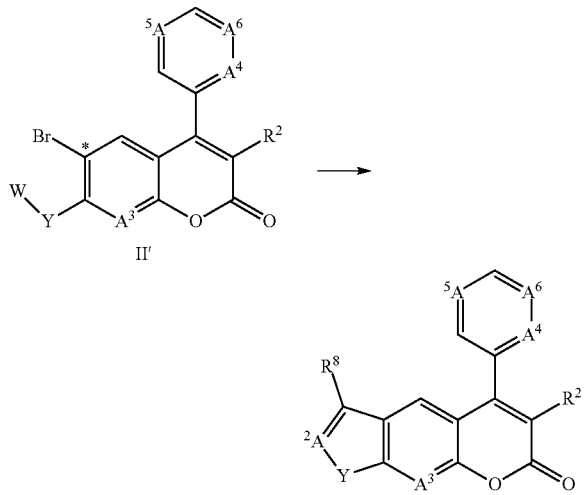

wherein $A^3$, $A^4$, $A^5$, $A^6$, $R^2$, $R^8$ and Y are as defined above; W is selected from the group consisting of

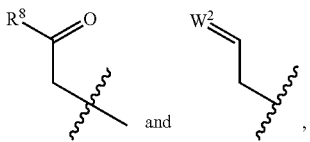

wherein $R^8$ is as defined above, and
$W^2$ is selected from the group consisting of $CH_2$, CH—$CH_3$, $C(CH_3)_2$, CH—$CH_2$—$CH_3$, $C(CH_3)$—$CH_2$—$CH_3$, CH—$CH(CH_3)$—$CH_3$, and CH—$CH_2$—$CH_2$—$CH_3$, and said method further comprises the step of transition metal mediated intramolecular alkylation at the position marked with an asterisk in the above formula II';
or W is hydrogen and said method further comprises transition metal mediated acylation at the position marked with an asterisk in the above formula II' using

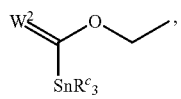

wherein $W^2$ is as defined above and $R^c$ is $(C_1\text{-}C_4)$alkyl; followed by cyclization using hydroxylamine.

Further embodiments of the present invention are detailed in the following items:
B1. A compound of the general formula (II) or a salt or solvate thereof, wherein $A^1$ is selected from the group consisting of N and C—$R^8$;
$A^2$ is selected from the group consisting of N and C—$R^3$;
$A^3$ is selected from the group consisting of N and C—$R^9$;
$A^4$ and $A^5$ and $A^6$ are independently selected from the group consisting of N and C—$R^1$;
$R^1$ is selected from the group consisting of hydrogen, methyl, chloro, fluoro, methoxy, ethoxy and trifluoromethyl;
$R^2$ is selected from the group consisting of hydrogen, bromo and methyl;
$R^3$ is selected from the group consisting of hydrogen, methyl, morpholinyl, morpholinomethyl, N-methylaminomethyl, N,N-dimethylaminomethyl and cyano;
Y is selected from the group consisting of O and S;
$R^8$ is selected from the group consisting of methyl, ethyl and cyclopropyl;
$R^9$ is selected from the group consisting of hydrogen, methyl and methoxy;
with the proviso that the following compounds are excluded:
3-methyl-5-phenyl-7H-furo[3,2-g]chromen-7-one, 2,3,9-trimethyl-5-phenyl-7H-furo[3,2-g]chromen-7-one, 3,9-dimethyl-5-phenyl-7H-furo[3,2-g]chromen-7-one, 2,3-dimethyl-5-phenyl-7H-furo[3,2-g]chromen-7-one, 3-ethyl-9-methyl-5-phenyl-7H-furo[3,2-g]chromen-7-one, and 2-methyl-8-phenyl-6H-chromeno[6,7-d]oxazol-6-one.

B2. A compound of the general formula (II) or a salt or solvate thereof, wherein
$A^1$ is selected from the group consisting of N and C—$R^8$;
$A^2$ is selected from the group consisting of N and C—$R^3$;
$A^3$ is selected from the group consisting of N and C—$R^9$;
$A^4$ and $A^5$ and $A^6$ are independently selected from the group consisting of N and C—$R^1$;
$R^1$ is selected from the group consisting of hydrogen, methyl, chloro, fluoro, methoxy, ethoxy and trifluoromethyl;
$R^2$ is selected from the group consisting of hydrogen and methyl;
$R^3$ is selected from the group consisting of hydrogen, methyl, morpholinyl, morpholinomethyl, N-methylaminomethyl, N,N-dimethylaminomethyl and cyano;
Y is selected from the group consisting of O and S;
$R^8$ is selected from the group consisting of methyl, ethyl and cyclopropyl;
$R^9$ is selected from the group consisting of hydrogen, methyl and methoxy;
with the proviso that the following compounds are excluded:
3-methyl-5-phenyl-7H-furo[3,2-g]chromen-7-one, 2,3,9-trimethyl-5-phenyl-7H-furo[3,2-g]chromen-7-one, 3,9-dimethyl-5-phenyl-7H-furo[3,2-g]chromen-7-one, 2,3-dimethyl-5-phenyl-7H-furo[3,2-g]chromen-7-one, 3-ethyl-9-methyl-5-phenyl-7H-furo[3,2-g]chromen-7-one, and 2-methyl-8-phenyl-6H-chromeno[6,7-d]oxazol-6-one.

B3. A compound of the general formula (II) or a salt or solvate thereof, wherein
$A^1$ is C—$R^8$; $A^2$ is C—$R^3$; $A^3$ is C—$R^9$; Y is O;
$A^4$ and $A^5$ and $A^6$ are independently selected from the group consisting of N and C—$R^1$;
$R^1$ is selected from the group consisting of hydrogen, $(C_1\text{-}C_3)$alkyl, halogen, $(C_1\text{-}C_3)$alkoxy and $(C_1\text{-}C_3)$haloalkyl;
$R^2$ is selected from the group consisting of hydrogen, halogen and $(C_1\text{-}C_3)$alkyl;

R³ is selected from the group consisting of hydrogen, (C₁-C₃)alkyl, NR⁴R⁵, (C₁-C₃)alkyl-NR⁴R⁵ and cyano;
wherein R⁴ and R⁵ are independently selected from the group consisting of hydrogen, (C₃-C₅)cycloalkyl, (C₃-C₅)heterocycloalkyl, (C₁-C₃)alkyl, or R⁴ and R⁵ together with the nitrogen atom to which they are attached form a 5- to 7-membered heterocyclic ring optionally comprising in addition to the aforementioned nitrogen atom a further heteroatom group selected from the group consisting of O and NR⁶, wherein R⁶ is selected from the group consisting of hydrogen, methyl, acetyl and formyl;
R⁸ is selected from the group consisting of (C₁-C₄)alkyl, (C₃-C₅)cycloalkyl and (C₃-C₅)heterocycloalkyl;
R⁹ is selected from the group consisting of hydrogen, (C₁-C₃)alkyl and (C₁-C₃)alkoxy;
with the proviso that the following compounds are excluded:
3-methyl-5-phenyl-7H-furo[3,2-g]chromen-7-one, 2,3,9-trimethyl-5-phenyl-7H-furo[3,2-g]chromen-7-one, 3,9-dimethyl-5-phenyl-7H-furo[3,2-g]chromen-7-one, 2,3-dimethyl-5-phenyl-7H-furo[3,2-g]chromen-7-one, 3-ethyl-9-methyl-5-phenyl-7H-furo[3,2-g]chromen-7-one, 3-(tert-butyl)-5-phenyl-7H-furo[3,2-g]chromen-7-one, and 3-(tert-butyl)-9-methyl-5-phenyl-7H-furo[3,2-g]chromen-7-one.

B4. A compound of the general formula (II) or a salt or solvate thereof, wherein
A¹ is C—R⁸; A² is C—R³; A³ is C—R⁹; Y is O;
A⁴ and A⁵ and A⁶ are independently selected from the group consisting of N and C—R¹;
R¹ is selected from the group consisting of hydrogen, methyl, chloro, fluoro, methoxy, ethoxy and trifluoromethyl;
R² is selected from the group consisting of hydrogen, bromo and methyl;
R³ is selected from the group consisting of hydrogen, methyl, morpholinyl, morpholinomethyl, N-methylaminomethyl, N,N-dimethylaminomethyl and cyano;
R⁸ is selected from the group consisting of methyl, ethyl and cyclopropyl;
R⁹ is selected from the group consisting of hydrogen, methyl and methoxy; with the proviso that the following compounds are excluded:
3-methyl-5-phenyl-7H-furo[3,2-g]chromen-7-one, 2,3,9-trimethyl-5-phenyl-7H-furo[3,2-g]chromen-7-one, 3,9-dimethyl-5-phenyl-7H-furo[3,2-g]chromen-7-one, 2,3-dimethyl-5-phenyl-7H-furo[3,2-g]chromen-7-one, and 3-ethyl-9-methyl-5-phenyl-7H-furo[3,2-g]chromen-7-one.

B5. A compound of the general formula (II) or a salt or solvate thereof, wherein
A¹ is C—R⁸; A² is C—R³; A³ is C—R⁹; Y is O;
A⁴ and A⁵ and A⁶ are independently selected from the group consisting of N and C—R¹;
R¹ is selected from the group consisting of hydrogen, methyl, chloro, fluoro, methoxy, ethoxy and trifluoromethyl;
R² is selected from the group consisting of hydrogen and methyl;
R³ is selected from the group consisting of hydrogen, morpholinyl, morpholinomethyl, N,N-dimethylaminomethyl and cyano;
R⁸ is selected from the group consisting of methyl, ethyl and cyclopropyl;
R⁹ is selected from the group consisting of hydrogen, methyl and methoxy;
with the proviso that the following compounds are excluded:
3-methyl-5-phenyl-7H-furo[3,2-g]chromen-7-one, 3,9-dimethyl-5-phenyl-7H-furo[3,2-g]chromen-7-one, and 3-ethyl-9-methyl-5-phenyl-7H-furo[3,2-g]chromen-7-one.

B6. A compound selected from the group consisting of:
5-(2-methoxyphenyl)-3,9-dimethyl-7H-furo[3,2-g]chromen-7-one,
5-(3-methoxyphenyl)-3,9-dimethyl-7H-furo[3,2-g]chromen-7-one,
5-(2-chlorophenyl)-3,9-dimethyl-7H-furo[3,2-g]chromen-7-one,
3,9-dimethyl-5-(3-(trifluoromethyl)phenyl)-7H-furo[3,2-g]chromen-7-one,
5-(2-fluorophenyl)-3,6,9-trimethyl-7H-furo[3,2-g]chromen-7-one,
5-(3-methoxyphenyl)-3,6,9-trimethyl-7H-furo[3,2-g]chromen-7-one,
5-(2-methoxyphenyl)-3,6,9-trimethyl-7H-furo[3,2-g]chromen-7-one,
5-(2-fluorophenyl)-3,9-dimethyl-7H-furo[3,2-g]chromen-7-one,
3,6,9-trimethyl-5-phenyl-7H-furo[3,2-g]chromen-7-one,
5-(2-ethoxyphenyl)-3,6,9-trimethyl-7H-furo[3,2-g]chromen-7-one,
5-(2-chlorophenyl)-3,6,9-trimethyl-7H-furo[3,2-g]chromen-7-one,
3,9-dimethyl-2-morpholino-5-phenyl-7H-furo[3,2-g]chromen-7-one,
3,9-dimethyl-7-oxo-5-phenyl-7H-furo[3,2-g]chromene-2-carbonitrile,
3,9-dimethyl-2-(morpholinomethyl)-5-phenyl-7H-furo[3,2-g]chromen-7-one,
2-((dimethylamino)methyl)-3,9-dimethyl-5-phenyl-7H-furo[3,2-g]chromen-7-one,
3-ethyl-6,9-dimethyl-5-phenyl-7H-furo[3,2-g]chromen-7-one,
3-methyl-5-(o-tolyl)-7H-furo[3,2-g]chromen-7-one,
3-methyl-5-(m-tolyl)-7H-furo[3,2-g]chromen-7-one,
5-(2-methoxyphenyl)-3-methyl-7H-furo[3,2-g]chromen-7-one,
5-(3-methoxyphenyl)-3-methyl-7H-furo[3,2-g]chromen-7-one,
5-(2-chlorophenyl)-3-methyl-7H-furo[3,2-g]chromen-7-one,
5-(3-chlorophenyl)-3-methyl-7H-furo[3,2-g]chromen-7-one,
9-methoxy-3-methyl-5-phenyl-7H-furo[3,2-g]chromen-7-one,
3-cyclopropyl-9-methyl-5-phenyl-7H-furo[3,2-g]chromen-7-one,
3-cyclopropyl-6,9-dimethyl-5-phenyl-7H-furo[3,2-g]chromen-7-one,
3,9-dimethyl-5-(pyridin-3-yl)-7H-furo[3,2-g]chromen-7-one,
3,9-dimethyl-7-oxo-5-phenyl-7H-furo[3,2-g]chromene-2-carbonitrile,
2-((dimethylamino)methyl)-3,6,9-trimethyl-5-phenyl-7H-furo[3,2-g]chromen-7-one,
3,6,9-trimethyl-5-(pyridin-3-yl)-7H-furo[3,2-g]chromen-7-one,
3,9-dimethyl-5-(pyridin-2-yl)-7H-furo[3,2-g]chromen-7-one,
3,9-dimethyl-5-(o-tolyl)-7H-furo[3,2-g]chromen-7-one,
5-(2-methoxypyridin-3-yl)-3,6,9-trimethyl-7H-furo[3,2-g]chromen-7-one, and 5-(4-methoxypyridin-3-yl)-3,6,9-trimethyl-7H-furo[3,2-g]
chromen-7-one,
or a salt or solvate thereof.

B7. A compound of the general formula (II) or a salt or
solvate thereof, wherein
$A^1$ is C—$R^8$; $A^2$ is C—$R^3$; $A^3$ is C—$R^9$; Y is O;
$A^4$ and $A^5$ and $A^6$ are independently selected from the
group consisting of N and C—$R^1$;
$R^1$ is selected from the group consisting of hydrogen,
($C_1$-$C_3$)alkyl, halogen, ($C_1$-$C_3$)alkoxy and ($C_1$-$C_3$)haloalkyl;
$R^2$ is selected from the group consisting of hydrogen,
halogen and ($C_1$-$C_3$)alkyl;
$R^3$ is selected from the group consisting of hydrogen,
($C_1$-$C_3$)alkyl, $NR^4R^5$, ($C_1$-$C_3$)alkyl-$NR^4R^5$ and cyano;
wherein $R^4$ and $R^5$ are independently selected from the
group consisting of hydrogen, ($C_3$-$C_5$)cycloalkyl, ($C_3$-$C_5$)heterocycloalkyl, and ($C_1$-$C_3$)alkyl, or $R^4$ and $R^5$
together with the nitrogen atom to which they are
attached form a 5- to 7-membered heterocyclic ring
optionally comprising in addition to the aforementioned nitrogen atom a further heteroatom group
selected from the group consisting of O and $NR^6$,
wherein $R^6$ is selected from the group consisting of
hydrogen, methyl, acetyl and formyl;
$R^8$ is selected from the group consisting of ($C_1$-$C_4$)alkyl,
($C_3$-$C_5$)cycloalkyl, and ($C_3$-$C_5$)heterocycloalkyl;
$R^9$ is selected from the group consisting of hydrogen,
($C_1$-$C_3$)alkyl and ($C_1$-$C_3$)alkoxy with the proviso that
at least one of the following conditions is fulfilled:
1) $R^2$ is halogen, or
2) $R^3$ is selected from the group consisting of $NR^4R^5$ and
cyano,
3) $A^4$ or $A^5$ or $A^6$ is N.

B8. A compound of the general formula (II) or a salt or
solvate thereof, wherein
$A^1$ is C—$R^8$; $A^2$ is C—$R^3$; $A^3$ is C—$R^9$; Y is O;
$A^4$ and $A^5$ and $A^6$ are independently selected from the
group consisting of N and C—$R^1$;
$R^1$ is selected from the group consisting of hydrogen,
methyl, chloro, fluoro, methoxy, ethoxy and trifluoromethyl;
$R^2$ is selected from the group consisting of hydrogen,
bromo and methyl;
$R^3$ is selected from the group consisting of hydrogen,
methyl, morpholinyl, morpholinomethyl, N-methylaminomethyl, N,N-dimethylaminomethyl and cyano;
$R^8$ is selected from the group consisting of methyl, ethyl
and cyclopropyl;
$R^9$ is selected from the group consisting of hydrogen,
methyl and methoxy;
with the proviso that at least one of the following conditions is fulfilled:
1) $R^2$ is bromo,
2) $R^3$ is selected from the group consisting of morpholinyl
and cyano,
3) $A^4$ or $A^5$ or $A^6$ is N.

B9. A compound of the general formula (II) or a salt or
solvate thereof, wherein
$A^1$ is C—$R^8$; $A^2$ is C—$R^3$; $A^3$ is C—$R^9$; Y is O;
$A^4$ and $A^5$ and $A^6$ are independently selected from the
group consisting of N and C—$R^1$;
$R^1$ is selected from the group consisting of hydrogen,
methyl, chloro, fluoro, methoxy, ethoxy and trifluoromethyl;
$R^2$ is selected from the group consisting of hydrogen,
methyl $R^3$ is selected from the group consisting of hydrogen,
morpholinyl, morpholinomethyl, N,N-dimethylaminomethyl and cyano;
$R^8$ is selected from the group consisting of methyl, ethyl
and cyclopropyl;
$R^9$ is selected from the group consisting of hydrogen,
methyl and methoxy;
with the proviso that at least one of the following conditions is fulfilled:
1) $R^3$ is selected from the group consisting of morpholinyl
and cyano
2) $A^4$ or $A^5$ or $A^6$ is N.

B10. A compound of the general formula (II) or a salt or
solvate thereof, wherein
$A^1$ is C—$CH_3$; $A^2$ is C—$R^3$; $A^3$ is C—$CH_3$; Y is O;
$A^4$ and $A^5$ and $A^6$ are independently selected from the
group consisting of N and C—H;
$R^2$ is selected from the group consisting of hydrogen and
methyl;
$R^3$ is selected from the group consisting of hydrogen,
morpholinyl and cyano;
with the proviso that at least one of the following conditions is fulfilled:
1) $R^3$ is selected from the group consisting of morpholinyl
and cyano
2) $A^4$ or $A^5$ or $A^6$ is N.

B11. A compound selected from the group consisting of:
3,9-dimethyl-2-morpholino-5-phenyl-7H-furo[3,2-g]
chromen-7-one,
3,9-dimethyl-7-oxo-5-phenyl-7H-furo[3,2-g]chromene-2-
carbonitrile,
3,9-dimethyl-5-(pyridin-3-yl)-7H-furo[3,2-g]chromen-7-
one,
3,9-dimethyl-7-oxo-5-phenyl-7H-furo[3,2-g]chromene-2-
carbonitrile,
3,6,9-trimethyl-5-(pyridin-3-yl)-7H-furo[3,2-g]chromen-7-
one,
3,9-dimethyl-5-(pyridin-2-yl)-7H-furo[3,2-g]chromen-7-
one,
5-(2-methoxypyridin-3-yl)-3,6,9-trimethyl-7H-furo[3,2-g]
chromen-7-one, and
5-(4-methoxypyridin-3-yl)-3,6,9-trimethyl-7H-furo[3,2-g]
chromen-7-one,
or a salt or solvate thereof.

B12. A compound of the general formula (II) or a salt or
solvate thereof, wherein
$A^1$ is C—$R^8$; $A^2$ is C—$R^3$; $A^3$ is C—$R^9$; Y is O;
one of $A^4$ and $A^5$ and $A^6$ is N and the others are independently selected from the group consisting of N and
C—$R^1$;
$R^1$ is selected from the group consisting of hydrogen,
($C_1$-$C_3$)alkyl, halogen, ($C_1$-$C_3$)alkoxy and ($C_1$-$C_3$)haloalkyl;
$R^2$ is selected from the group consisting of hydrogen,
halogen and ($C_1$-$C_3$)alkyl;
$R^3$ is selected from the group consisting of hydrogen,
($C_1$-$C_3$)alkyl, $NR^4R^5$, ($C_1$-$C_3$)alkyl-$NR^4R^5$ and cyano;
wherein $R^4$ and $R^5$ are independently selected from the
group consisting of hydrogen, ($C_3$-$C_5$)cycloalkyl, ($C_3$-$C_5$)heterocycloalkyl, and ($C_1$-$C_3$)alkyl, or $R^4$ and $R^5$
together with the nitrogen atom to which they are
attached form a 5- to 7-membered heterocyclic ring
optionally comprising in addition to the aforementioned nitrogen atom a further heteroatom group
selected from the group consisting of O and $NR^6$,
wherein $R^6$ is selected from the group consisting of
hydrogen, methyl, acetyl and formyl;

R$^8$ is selected from the group consisting of (C$_1$-C$_4$)alkyl, (C$_3$-C$_5$)cycloalkyl and (C$_3$-C$_5$)heterocycloalkyl;

R$^9$ is selected from the group consisting of hydrogen, (C$_1$-C$_3$)alkyl and (C$_1$-C$_3$)alkoxy.

B13. A compound of the general formula (II) or a salt or solvate thereof, wherein A$^1$ is C—R$^8$; A$^2$ is C—R$^3$; A$^3$ is C—R$^9$; Y is O;

one of A$^4$ and A$^5$ and A$^6$ is N and the others are independently selected from the group consisting of N and C—R$^1$;

R$^1$ is selected from the group consisting of hydrogen, methyl, chloro, fluoro, methoxy, ethoxy and trifluoromethyl;

R$^2$ is selected from the group consisting of hydrogen, bromo and methyl;

R$^3$ is selected from the group consisting of hydrogen, methyl, morpholinyl, morpholinomethyl, N-methylaminomethyl, N,N-dimethylaminomethyl and cyano;

R$^8$ is selected from the group consisting of methyl, ethyl and cyclopropyl;

R$^9$ is selected from the group consisting of hydrogen, methyl and methoxy.

B14. A compound of the general formula (II) or a salt or solvate thereof, wherein A$^1$ is C—R$^8$; A$^2$ is C—R$^3$; A$^3$ is C—R$^9$; Y is O;

one of A$^4$ and A$^5$ and A$^6$ is N and the others are independently selected from the group consisting of N and C—R$^1$;

R$^1$ is selected from the group consisting of hydrogen, methyl, chloro, fluoro, methoxy, ethoxy and trifluoromethyl;

R$^2$ is selected from the group consisting of hydrogen and methyl;

R$^3$ is selected from the group consisting of hydrogen, morpholinyl, morpholinomethyl, N,N-dimethylaminomethyl and cyano;

R$^8$ is selected from the group consisting of methyl, ethyl and cyclopropyl;

R$^9$ is selected from the group consisting of hydrogen, methyl and methoxy.

B15. A compound of the general formula (II) or a salt or solvate thereof, wherein A$^1$ is C—CH$_3$; A$^2$ is C—H; A$^3$ is C—CH$_3$; Y is O;

one of A$^4$ and A$^5$ and A$^6$ is N and the others are independently selected from the group consisting of N and C—H;

R$^2$ is selected from the group consisting of hydrogen and methyl.

B 16. A compound selected from the group consisting of:

3,9-dimethyl-5-(pyridin-3-yl)-7H-furo[3,2-g]chromen-7-one, 3,6,9-trimethyl-5-(pyridin-3-yl)-7H-furo[3,2-g]chromen-7-one, 3,9-dimethyl-5-(pyridin-2-yl)-7H-furo[3,2-g]chromen-7-one, 5-(2-methoxypyridin-3-yl)-3,6,9-trimethyl-7H-furo[3,2-g]chromen-7-one, and 5-(4-methoxypyridin-3-yl)-3,6,9-trimethyl-7H-furo[3,2-g]chromen-7-one, or a salt or solvate thereof.

B17. A compound of the general formula (II) or a salt or solvate thereof, wherein A$^1$ is selected from the group consisting of N and C—R$^8$;

A$^2$ is selected from the group consisting of N and C—R$^3$;

A$^3$ is selected from the group consisting of N and C—R$^9$;

A$^4$ and A$^5$ and A$^6$ are independently selected from the group consisting of N and C—R$^1$;

R$^1$ is selected from the group consisting of hydrogen, (C$_1$-C$_3$)alkyl, halogen, (C$_1$-C$_3$)alkoxy and (C$_1$-C$_3$)haloalkyl;

R$^2$ is selected from the group consisting of hydrogen, halogen and (C$_1$-C$_3$)alkyl;

R$^3$ is selected from the group consisting of hydrogen, (C$_1$-C$_3$)alkyl, NR$^4$R$^5$, (C$_1$-C$_3$)alkyl-NR$^4$R$^5$ and cyano;

wherein R$^4$ and R$^5$ are independently selected from the group consisting of hydrogen, (C$_3$-C$_5$)cycloalkyl, (C$_3$-C$_5$)heterocycloalkyl, (C$_1$-C$_3$)alkyl, or R$^4$ and R$^5$ together with the nitrogen atom to which they are attached form a 5- to 7-membered heterocyclic ring optionally comprising in addition to the aforementioned nitrogen atom a further heteroatom group selected from the group consisting of O and NR$^6$, wherein R$^6$ is selected from the group consisting of hydrogen, methyl, acetyl and formyl;

Y is selected from the group consisting of O and S, wherein if Y is O, at least one of A$^1$, A$^2$ or A$^3$ is N;

R$^8$ is selected from the group consisting of (C$_1$-C$_4$)alkyl, (C$_3$-C$_5$)cycloalkyl and (C$_3$-C$_5$)heterocycloalkyl;

R$^9$ is selected from the group consisting of hydrogen, (C$_1$-C$_3$)alkyl and (C$_1$-C$_3$)alkoxy;

with the proviso that 2-methyl-8-phenyl-6H-chromeno[6,7-d]oxazol-6-one is excluded.

B18. A compound of the general formula (II) or a salt or solvate thereof, wherein A$^1$ is selected from the group consisting of N and C—R$^8$;

A$^2$ is selected from the group consisting of N and C—R$^3$;

A$^3$ is selected from the group consisting of N and C—R$^9$;

A$^4$ and A$^5$ and A$^6$ are independently selected from the group consisting of N and C—R$^1$;

R$^1$ is selected from the group consisting of hydrogen, methyl, chloro, fluoro, methoxy, ethoxy and trifluoromethyl;

R$^2$ is selected from the group consisting of hydrogen, bromo and methyl;

R$^3$ is selected from the group consisting of hydrogen, methyl, morpholinyl, morpholinomethyl, N-methylaminomethyl, N,N-dimethylaminomethyl and cyano;

Y is selected from the group consisting of O and S, wherein if Y is O, at least one of A$^1$, A$^2$ or A$^3$ is N;

R$^8$ is selected from the group consisting of methyl, ethyl and cyclopropyl;

R$^9$ is selected from the group consisting of hydrogen, methyl and methoxy;

with the proviso that 2-methyl-8-phenyl-6H-chromeno[6,7-d]oxazol-6-one is excluded.

B19. A compound of the general formula (II) or a salt or solvate thereof, wherein A$^1$ is selected from the group consisting of N and C—CH$_3$;

A$^2$ is selected from the group consisting of N and C—R$^3$;

A$^3$ is selected from the group consisting of N and C—CH$_3$;

A$^4$ and A$^5$ and A$^6$ are independently selected from the group consisting of N and C—H;

R$^2$ is selected from the group consisting of hydrogen and methyl;

R$^3$ is selected from the group consisting of hydrogen, methyl and N-methylaminomethyl;

Y is selected from the group consisting of O and S, wherein if Y is O, at least one of A$^1$, A$^2$ or A$^3$ is N;

with the proviso that 2-methyl-8-phenyl-6H-chromeno[6,7-d]oxazol-6-one is excluded.

B20. A compound selected from the group consisting of:
3-methyl-5-phenyl-7H-furo[2,3-b]pyrano[3,2-e]pyridin-7-one,
3,6-dimethyl-5-phenyl-7H-furo[2,3-b]pyrano[3,2-e]pyridin-7-one,
3,6,9-trimethyl-5-phenyl-7H-chromeno[6,7-d]isoxazol-7-one,
6,9-dimethyl-4-phenyl-2H-thieno[3,2-g]chromen-2-one,
2,4-dimethyl-8-phenyl-6H-chromeno[6,7-d]oxazol-6-one,
4-methyl-2-((methylamino)methyl)-8-phenyl-6H-chromeno[6,7-d]oxazol-6-one,
3,6,9-trimethyl-4-phenyl-2H-thieno[3,2-g]chromen-2-one,
4-methyl-8-phenyl-6H-chromeno[6,7-d]oxazol-6-one,
2,4,7-trimethyl-8-phenyl-6H-chromeno[6,7-d]oxazol-6-one, and
3,9-dimethyl-5-phenyl-7H-chromeno[6,7-d]isoxazol-7-one,
or a salt or solvate thereof.

B21. A compound of the general formula (II) or a salt or solvate thereof, wherein
Y is S;
$A^1$ is selected from the group consisting of N and C—$R^8$;
$A^2$ is selected from the group consisting of N and C—$R^3$;
$A^3$ is selected from the group consisting of N and C—$R^9$;
$A^4$ and $A^5$ and $A^6$ are independently selected from the group consisting of N and C—$R^1$;
$R^1$ is selected from the group consisting of hydrogen, ($C_1$-$C_3$)alkyl, halogen, ($C_1$-$C_3$)alkoxy and ($C_1$-$C_3$)haloalkyl;
$R^2$ is selected from the group consisting of hydrogen, halogen and ($C_1$-$C_3$)alkyl;
$R^3$ is selected from the group consisting of hydrogen, ($C_1$-$C_3$)alkyl, $NR^4R^5$, ($C_1$-$C_3$)alkyl-$NR^4R^5$ and cyano;
wherein $R^4$ and $R^5$ are independently selected from the group consisting of hydrogen, ($C_3$-$C_5$)cycloalkyl, ($C_3$-$C_5$)heterocycloalkyl, ($C_1$-$C_3$)alkyl, or $R^4$ and $R^5$ together with the nitrogen atom to which they are attached form a 5- to 7-membered heterocyclic ring optionally comprising in addition to the aforementioned nitrogen atom a further heteroatom group selected from the group consisting of O and $NR^6$, wherein $R^6$ is selected from the group consisting of hydrogen, methyl, acetyl and formyl; $R^8$ is selected from the group consisting of ($C_1$-$C_4$)alkyl, ($C_3$-$C_5$)cycloalkyl and ($C_3$-$C_5$)heterocycloalkyl;
$R^9$ is selected from the group consisting of hydrogen, ($C_1$-$C_3$)alkyl and ($C_1$-$C_3$)alkoxy.

B22. A compound of the general formula (II) or a salt or solvate thereof, wherein
Y is S;
$A^1$ is selected from the group consisting of N and C—$R^8$;
$A^2$ is selected from the group consisting of N and C—$R^3$;
$A^3$ is selected from the group consisting of N and C—$R^9$;
$A^4$ and $A^5$ and $A^6$ are independently selected from the group consisting of N and C—$R^1$;
$R^1$ is selected from the group consisting of hydrogen, methyl, chloro, fluoro, methoxy, ethoxy and trifluoromethyl;
$R^2$ is selected from the group consisting of hydrogen, bromo and methyl;
$R^3$ is selected from the group consisting of hydrogen, methyl, morpholinyl, morpholinomethyl, N-methylaminomethyl, N,N-dimethylaminomethyl and cyano;
$R^8$ is selected from the group consisting of methyl, ethyl and cyclopropyl;
$R^9$ is selected from the group consisting of hydrogen, methyl and methoxy.

B23. A compound of the general formula (II) or a salt or solvate thereof, wherein
Y is S;
$A^1$ is selected from the group consisting of N and C—$CH_3$;
$A^2$ is selected from the group consisting of N and C—$R^3$;
$A^3$ is selected from the group consisting of N and C—$CH_3$;
$A^4$ and $A^5$ and $A^6$ are independently selected from the group consisting of N and C—H;
$R^2$ is selected from the group consisting of hydrogen and methyl;
$R^3$ is selected from the group consisting of hydrogen, methyl and N-methylaminomethyl.

B24. A compound selected from the group consisting of:
6,9-dimethyl-4-phenyl-2H-thieno[3,2-g]chromen-2-one, and
3,6,9-trimethyl-4-phenyl-2H-thieno[3,2-g]chromen-2-one,
or a salt or solvate thereof.

B25. A compound of the general formula (II) or a salt or solvate thereof, wherein
Y is O;
$A^1$ is selected from the group consisting of N and C—$R^8$;
$A^2$ is selected from the group consisting of N and C—$R^3$;
$A^3$ is selected from the group consisting of N and C—$R^9$;
wherein at least one of $A^1$, $A^2$ or $A^3$ is N;
$A^4$ and $A^5$ and $A^6$ are independently selected from the group consisting of N and C—$R^1$;
$R^1$ is selected from the group consisting of hydrogen, ($C_1$-$C_3$)alkyl, halogen, ($C_1$-$C_3$)alkoxy and ($C_1$-$C_3$)haloalkyl;
$R^2$ is selected from the group consisting of hydrogen, halogen and ($C_1$-$C_3$)alkyl;
$R^3$ is selected from the group consisting of hydrogen, ($C_1$-$C_3$)alkyl, $NR^4R^5$, ($C_1$-$C_3$)alkyl-$NR^4R^5$ and cyano;
wherein $R^4$ and $R^5$ are independently selected from the group consisting of hydrogen, ($C_3$-$C_5$)cycloalkyl, ($C_3$-$C_5$)heterocycloalkyl and ($C_1$-$C_3$)alkyl, or $R^4$ and $R^5$ together with the nitrogen atom to which they are attached form a 5- to 7-membered heterocyclic ring optionally comprising in addition to the aforementioned nitrogen atom a further heteroatom group selected from the group consisting of O and $NR^6$, wherein $R^6$ is selected from the group consisting of hydrogen, methyl, acetyl and formyl;
$R^8$ is selected from the group consisting of ($C_1$-$C_4$)alkyl, ($C_3$-$C_5$)cycloalkyl and ($C_3$-$C_5$)heterocycloalkyl;
$R^9$ is selected from the group consisting of hydrogen, ($C_1$-$C_3$)alkyl and ($C_1$-$C_3$)alkoxy: with the proviso that 2-methyl-8-phenyl-6H-chromeno[6,7-d]oxazol-6-one is excluded.

B26. A compound of the general formula (II) or a salt or solvate thereof, wherein
Y is O;
$A^1$ is selected from the group consisting of N and C—$R^8$;
$A^2$ is selected from the group consisting of N and C—$R^3$;
$A^3$ is selected from the group consisting of N and C—$R^9$;
wherein at least one of $A^1$, $A^2$ or $A^3$ is N;
$A^4$ and $A^5$ and $A^6$ are independently selected from the group consisting of N and C—$R^1$;
$R^1$ is selected from the group consisting of hydrogen, methyl, chloro, fluoro, methoxy, ethoxy and trifluoromethyl;
$R^2$ is selected from the group consisting of hydrogen, bromo and methyl;

R³ is selected from the group consisting of hydrogen, methyl, morpholinyl, morpholinomethyl, N-methylaminomethyl, N,N-dimethylaminomethyl and cyano;
R⁸ is selected from the group consisting of methyl, ethyl and cyclopropyl;
R⁹ is selected from the group consisting of hydrogen, methyl and methoxy; with the proviso that 2-methyl-8-phenyl-6H-chromeno[6,7-d]oxazol-6-one is excluded.

B27. A compound of the general formula (II) or a salt or solvate thereof, wherein
Y is O;
A¹ is selected from the group consisting of N and C—CH₃;
A² is selected from the group consisting of N and C—R³
A³ is selected from the group consisting of N and C—CH₃;
wherein at least one of A¹, A² or A³ is N;
A⁴ and A⁵ and A⁶ are independently selected from the group consisting of N and C—H;
R² is selected from the group consisting of hydrogen and methyl;
R³ is selected from the group consisting of hydrogen, methyl and N-methylaminomethyl;
with the proviso that 2-methyl-8-phenyl-6H-chromeno[6,7-d]oxazol-6-one is excluded.

B28. A compound selected from the group consisting of:
3-methyl-5-phenyl-7H-furo[2,3-b]pyrano[3,2-e]pyridin-7-one,
3,6-dimethyl-5-phenyl-7H-furo[2,3-b]pyrano[3,2-e]pyridin-7-one,
3,6,9-trimethyl-5-phenyl-7H-chromeno[6,7-d]isoxazol-7-one,
2,4-dimethyl-8-phenyl-6H-chromeno[6,7-d]oxazol-6-one,
4-methyl-2-((methylamino)methyl)-8-phenyl-6H-chromeno[6,7-d]oxazol-6-one,
4-methyl-8-phenyl-6H-chromeno[6,7-d]oxazol-6-one,
2,4,7-trimethyl-8-phenyl-6H-chromeno[6,7-d]oxazol-6-one, and
3,9-dimethyl-5-phenyl-7H-chromeno[6,7-d]isoxazol-7-one, or a salt or solvate thereof.

B29. A compound of the general formula (II) or a salt or solvate thereof, wherein
Y is O; A³ is N;
A¹ is selected from the group consisting of N and C—R⁸;
A² is selected from the group consisting of N and C—R³;
A⁴ and A⁵ and A⁶ are independently selected from the group consisting of N and C—R¹;
R¹ is selected from the group consisting of hydrogen, (C₁-C₃)alkyl, halogen, (C₁-C₃)alkoxy and (C₁-C₃)haloalkyl;
R² is selected from the group consisting of hydrogen, halogen and (C₁-C₃)alkyl;
R³ is selected from the group consisting of hydrogen, (C₁-C₃)alkyl, NR⁴R⁵, (C₁-C₃)alkyl-NR⁴R⁵ and cyano;
wherein R⁴ and R⁵ are independently selected from the group consisting of hydrogen, (C₃-C₅)cycloalkyl, (C₃-C₅)heterocycloalkyl, (C₁-C₃)alkyl, or R⁴ and R⁵ together with the nitrogen atom to which they are attached form a 5- to 7-membered heterocyclic ring optionally comprising in addition to the aforementioned nitrogen atom a further heteroatom group selected from the group consisting of O and NR⁶, wherein R⁶ is selected from the group consisting of hydrogen, methyl, acetyl and formyl;
R⁸ is selected from the group consisting of (C₁-C₄)alkyl, (C₃-C₅)cycloalkyl and (C₃-C₅)heterocycloalkyl.

B30. A compound of the general formula (II) or a salt or solvate thereof, wherein
Y is O; A³ is N;
A¹ is selected from the group consisting of N and C—R⁸;
A² is selected from the group consisting of N and C—R³;
A⁴ and A⁵ and A⁶ are independently selected from the group consisting of N and C—R¹;
R¹ is selected from the group consisting of hydrogen, methyl, chloro, fluoro, methoxy, ethoxy and trifluoromethyl;
R² is selected from the group consisting of hydrogen, bromo and methyl;
R³ is selected from the group consisting of hydrogen, methyl, morpholinyl, morpholinomethyl, N-methylaminomethyl, N,N-dimethylaminomethyl and cyano;
R⁸ is selected from the group consisting of methyl, ethyl and cyclopropyl.

B31. A compound of the general formula (II) or a salt or solvate thereof, wherein
Y is O; A³ is N;
A¹ is selected from the group consisting of N and C—CH₃;
A² is selected from the group consisting of N and C—R³;
A⁴ and A⁵ and A⁶ are independently selected from the group consisting of N and C—H;
R² is selected from the group consisting of hydrogen and methyl;
R³ is selected from the group consisting of hydrogen, methyl and N-methylaminomethyl.

B32. A compound selected from the group consisting of:
3-methyl-5-phenyl-7H-furo[2,3-b]pyrano[3,2-e]pyridin-7-one, and
3,6-dimethyl-5-phenyl-7H-furo[2,3-b]pyrano[3,2-e]pyridin-7-one.

B33. A compound of the general formula (II) or a salt or solvate thereof, wherein
Y is O; A¹ is N; A² is C—R³
A³ is selected from the group consisting of N and C—R⁹;
A⁴ and A⁵ and A⁶ are independently selected from the group consisting of N and C—R¹;
R¹ is selected from the group consisting of R¹ is selected from the group consisting of hydrogen, (C₁-C₃)alkyl, halogen, (C₁-C₃)alkoxy and (C₁-C₃)haloalkyl;
R² is selected from the group consisting of hydrogen, halogen and (C₁-C₃)alkyl;
R³ is selected from the group consisting of R³ is selected from the group consisting of hydrogen, (C₁-C₃)alkyl, NR⁴R⁵, (C₁-C₃)alkyl-NR⁴R⁵ and cyano;
wherein R⁴ and R⁵ are independently selected from the group consisting of hydrogen, (C₃-C₅)cycloalkyl, (C₃-C₅)heterocycloalkyl and (C₁-C₃)alkyl, or R⁴ and R⁵ together with the nitrogen atom to which they are attached form a 5- to 7-membered heterocyclic ring optionally comprising in addition to the aforementioned nitrogen atom a further heteroatom group selected from the group consisting of O and NR⁶, wherein R⁶ is selected from the group consisting of hydrogen, methyl, acetyl and formyl;
R⁹ is selected from the group consisting of hydrogen, (C₁-C₃)alkyl and (C₁-C₃)alkoxy;
with the proviso that 2-methyl-8-phenyl-6H-chromeno[6,7-d]oxazol-6-one is excluded.

B34. A compound of the general formula (II) or a salt or solvate thereof, wherein
Y is O; A¹ is N; A² is C—R³
A³ is selected from the group consisting of N and C—R⁹;

$A^4$ and $A^5$ and $A^6$ are independently selected from the group consisting of N and C—$R^1$;

$R^1$ is selected from the group consisting of hydrogen, methyl, chloro, fluoro, methoxy, ethoxy and trifluoromethyl;

$R^2$ is selected from the group consisting of hydrogen, bromo and methyl;

$R^3$ is selected from the group consisting of $R^3$ is selected from the group consisting of hydrogen, methyl, morpholinyl, morpholinomethyl, N-methylaminomethyl, N,N-dimethylaminomethyl and cyano;

$R^9$ is selected from the group consisting of hydrogen, methyl and methoxy;

with the proviso that 2-methyl-8-phenyl-6H-chromeno[6,7-d]oxazol-6-one is excluded.

B35. A compound of the general formula (II) or a salt or solvate thereof, wherein Y is O; $A^1$ is N; $A^2$ is C—$R^3$ $A^3$ is selected from the group consisting of N and C—$CH_3$;

$A^4$ and $A^5$ and $A^6$ are independently selected from the group consisting of N and C—H;

$R^2$ is selected from the group consisting of hydrogen and methyl;

$R^3$ is selected from the group consisting of $R^3$ is selected from the group consisting of hydrogen, methyl and N-methylaminomethyl.

B36. A compound of the general formula (II) or a salt or solvate thereof, wherein Y is O; $A^1$ is N; $A^2$ is C—$R^3$; $A^3$ is C—$CH_3$; $A^4$ and $A^5$ and $A^6$ are C—H;

$R^2$ is selected from the group consisting of hydrogen and methyl;

$R^3$ is selected from the group consisting of $R^3$ is selected from the group consisting of hydrogen, methyl and N-methylaminomethyl.

B37. A compound selected from the group consisting of:
2,4-dimethyl-8-phenyl-6H-chromeno[6,7-d]oxazol-6-one,
4-methyl-2-((methylamino)methyl)-8-phenyl-6H-chromeno[6,7-d]oxazol-6-one,
4-methyl-8-phenyl-6H-chromeno[6,7-d]oxazol-6-one, and
2,4,7-trimethyl-8-phenyl-6H-chromeno[6,7-d]oxazol-6-one,
or a salt or solvate thereof.

B38. A compound of the general formula (II) or a salt or solvate thereof, wherein Y is O;
$A^1$ is C—$R^8$;
$A^2$ is N;
$A^3$ is selected from the group consisting of N and C—$R^9$;
$A^4$ and $A^5$ and $A^6$ are independently selected from the group consisting of N and C—$R^1$;
$R^1$ is selected from the group consisting of hydrogen, $(C_1$-$C_3)$alkyl, halogen, $(C_1$-$C_3)$alkoxy and $(C_1$-$C_3)$haloalkyl;
$R^2$ is selected from the group consisting of hydrogen, halogen and $(C_1$-$C_3)$alkyl;
$R^8$ is selected from the group consisting of $(C_1$-$C_4)$alkyl, $(C_3$-$C_5)$cycloalkyl and $(C_3$-$C_5)$heterocycloalkyl;
$R^9$ is selected from the group consisting of hydrogen, $(C_1$-$C_3)$alkyl and $(C_1$-$C_3)$alkoxy.

B39. A compound of the general formula (II) or a salt or solvate thereof, wherein Y is O; $A^1$ is C—$R^8$; $A^2$ is N;
$A^3$ is selected from the group consisting of N and C—$R^9$;
$A^4$ and $A^5$ and $A^6$ are independently selected from the group consisting of N and C—$R^1$;

$R^1$ is selected from the group consisting of hydrogen, methyl, chloro, fluoro, methoxy, ethoxy and trifluoromethyl;

$R^2$ is selected from the group consisting of hydrogen, bromo and methyl;

$R^8$ is selected from the group consisting of methyl, ethyl and cyclopropyl;

$R^9$ is selected from the group consisting of hydrogen, methyl and methoxy.

B40. A compound of the general formula (II) or a salt or solvate thereof, wherein Y is O; $A^1$ is C—$CH_3$; $A^2$ is N;

$A^3$ is selected from the group consisting of N and C—$CH_3$;

$A^4$ and $A^5$ and $A^6$ are independently selected from the group consisting of N and C—H;

$R^2$ is selected from the group consisting of hydrogen and methyl.

B41. A compound selected from the group consisting of:
3,6,9-trimethyl-5-phenyl-7H-chromeno[6,7-d]isoxazol-7-one, and 3,9-dimethyl-5-phenyl-7H-chromeno[6,7-d]isoxazol-7-one, or a salt or solvate thereof.

In particular embodiments of the present invention $A^6$ is C—$R^1$, more particularly C—H.

In other particular embodiments of the present invention $A^6$ is N.

More particular embodiments of the present invention are the respective specific compounds of below Tables 1 and/or 2 which are encompassed by each respective of the aforementioned enumerated embodiments, even more particularly those having an $IC_{50}$ marked with "++" or "+++", yet even more particularly those having an $IC_{50}$ marked with "+++".

To keep the definitions as short as possible, the term "alkyl" is to be understood to encompass in certain embodiments alkyl, alkenyl and alkynyl. It is apparent to the skilled person that "$C_1$-alkenyl" and "$C_1$-alkynyl" are not meant to be included.

In the context of the present invention, a $(C_1$-$C_4)$alkyl group, if not stated otherwise, particularly denotes a linear or branched $(C_1$-$C_4)$alkyl, more particularly selected from the group consisting of —$CH_3$, —$C_2H_5$, —CH=$CH_2$, —C≡CH, —$C_3H_7$, —CH($CH_3)_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3)_2$, —CH($CH_3$)—$C_2H_5$, and —C($CH_3)_3$, even more particularly selected from the group consisting of —$CH_3$, —$C_2H_5$, —$(CH_2)_2CH_3$, —CH($CH_3)_2$, —$(CH_2)_3CH_3$, —$CH_2$—CH($CH_3)_2$, —CH($CH_3$)—$C_2H_5$, and —C($CH_3)_3$. The aforementioned alkyl groups may independently be substituted by one or more $(C_1$-$C_3)$alkoxy groups, particularly by one $(C_1$-$C_3)$alkoxy group, wherein particularly said $(C_1$-$C_3)$alkoxy is unsubstituted.

In the context of the present invention, a $(C_1$-$C_3)$alkyl group, if not stated otherwise, particularly denotes a linear or branched $(C_1$-$C_3)$alkyl, more particularly selected from the group consisting of —$CH_3$, —$C_2H_5$, —$(CH_2)_2CH_3$, —CH($CH_3)_2$, —$(CH_2)_3CH_3$, —$CH_2$—CH($CH_3)_2$, —CH($CH_3$)—$C_2H_5$, and —C($CH_3)_3$. The aforementioned alkyl groups may independently be substituted by one or more $(C_1$-$C_3)$alkoxy groups, particularly by one $(C_1$-$C_3)$alkoxy group, wherein particularly said $(C_1$-$C_3)$alkoxy is unsubstituted.

In context of the present invention, a $(C_3$-$C_5)$cycloalkyl group denotes a non-aromatic ring system containing three to five carbon atoms, particularly cyclopropane, cyclobutane, cyclopentane and cyclopentene. The aforementioned cycloalkyl groups may independently be substituted by one or more (C$_1$-C$_3$)alkoxy and/or (C$_1$-C$_3$)alkyl groups, particularly by one (C$_1$-C$_3$)alkoxy or (C$_1$-C$_3$)alkyl group, wherein particularly said (C$_1$-C$_3$)alkoxy and (C$_1$-C$_3$)alkyl is unsubstituted.

In context of the present invention, a (C$_3$-C$_5$)heterocycloalkyl group denotes a non-aromatic ring system containing three to five carbon atoms, wherein one or more, particularly one, of the carbon atoms in the ring are replaced by a heteroatom group selected from the group comprising O, S, SO, SO$_2$, N, and NR", particularly selected from the group comprising O, SO$_2$ and NR", wherein R" is independently selected from the group consisting of hydrogen, (C$_1$-C$_4$)alkyl, formyl, and acetyl. Particularly said (C$_3$-C$_5$) heterocycloalkyl group is selected from the group consisting of -oxetan-2-yl, -oxetan-3-yl, -tetrahydrofuran-2-yl, -tetrahydrofuran-3-yl, -aziridin-2-yl, -azetidin-2-yl, -azetidin-3-yl, -pyrrolidin-2-yl, -pyrrolidin-3-yl, 1,1-dioxidotetrahydrothiophen-3-yl, 1,1-dioxidothietan-3-yl, more particularly selected from the group consisting of -tetrahydrofuran-2-yl, -tetrahydrofuran-3-yl, -aziridin-2-yl, -pyrrolidin-2-yl, and -pyrrolidin-3-yl, wherein independently -aziridin-2-yl, -azetidin-2-yl, -azetidin-3-yl, -pyrrolidin-2-yl, -pyrrolidin-3-yl, is on their respective nitrogen atom substituted with a residue R" as detailed above. The aforementioned heterocycloalkyl groups may independently be substituted by one or more (C$_1$-C$_3$)alkoxy and/or (C$_1$-C$_3$)alkyl groups, particularly by one (C$_1$-C$_3$)alkoxy or (C$_1$-C$_3$)alkyl group, wherein particularly said (C$_1$-C$_3$)alkoxy and (C$_1$-C$_3$)alkyl is unsubstituted.

A (C$_1$-C$_3$)alkoxy group denotes an O—(C$_1$-C$_3$)alkyl group, wherein the respective alkyl part is as defined above; in particular embodiments of the present invention the (C$_1$-C$_3$)alkoxy group is selected from the group comprising methoxy, ethoxy, and isopropoxy.

A (C$_1$-C$_3$)haloalkyl group denotes a (C$_1$-C$_3$)alkyl group as defined above substituted by one or more halogen atoms, particularly substituted by one to five halogen atoms. More particularly the (C$_1$-C$_3$)haloalkyl group is selected from the group consisting of —C(R$^{10}$)$_3$, —CR$^{10}$(R$^{10'}$)$_2$, —CR$^{10}$(R$^{10'}$)R$^{10''}$, —C$_2$(R$^{10}$)$_5$, —CH$_2$—C(R$^{10}$)$_3$, —C(R$^{10}$)$_2$—CH(R$^{10'}$)$_2$, —CH$_2$—CR$^{10}$(R$^{10'}$)$_2$, —CH$_2$—CR$^{10}$(R$^{10'}$)R$^{10''}$, —C$_3$(R$^{10}$)$_7$, or —C$_2$H$_4$—C(R$^{10}$)$_3$, wherein R$^{10}$, R$^{10'}$, R$^{10''}$ independently represent F, Cl, Br or I, particularly F; more particularly, (C$_1$-C$_3$)haloalkyl is CF$_3$.

In particular embodiments of the present invention a halo or halogen group denotes fluoro, chloro, bromo, or iodo; particularly bromo, chloro or fluoro.

Constituents which are optionally substituted as stated herein may be substituted, unless otherwise noted, at any chemically possible position.

According to expert's knowledge the compounds of the invention as well as their salts may contain, e.g. when isolated in crystalline form, varying amounts of solvents. Included within the scope of the invention are therefore all solvates and in particular all hydrates of the compounds of the present invention as well as all solvates and in particular all hydrates of the salts of the compounds of the present invention. Particular solvates or hydrates are stoichiometric or substoichiometric solvates or hydrates comprising 0.5, 1 or 2 solvate or water molecules per molecule of compound of the present invention.

In the method for producing a compound according to the present invention, wherein W is

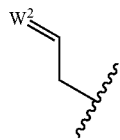

or wherein

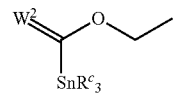

is used for transition metal mediated acylation at the position marked with an asterisk in formula II', R$^8$ is formed from the aforementioned group W$^2$ upon the transition metal mediated coupling at the position marked with an asterisk in formula II', wherein a hydrogen atom is added to the carbon atom of W$^2$ being part of the double bond, wherein the resulting R$^8$ can in this case be selected from the group consisting of methyl, ethyl, n-propyl, isopropyl, n-butyl, sec-butyl and isobutyl.

To describe a certain aspect of the method for producing a compound according to the present invention in further detail, transition metal mediated alkylation at the position marked with an asterisk in formula II' means in particular that a carbon-carbon bond is formed between the carbon atom at the position marked with an asterisk in formula II' (thus replacing the bromine atom) and the carbon atom of group W being part of the double bond (either to carbon or oxygen) and allowing for an exocyclic cyclization (resulting in the formation of a 5-membered ring).

To describe a certain aspect of the present invention in further detail, in the method for producing a compound according to the present invention wherein W is hydrogen (i.e. the group —Y—W is —Y—H), the transition metal mediated acylation at the position marked with an asterisk in formula II' as described above is accomplished first (thus replacing the bromine atom with a group —CO—R$^8$), followed by cyclization using hydroxylamine. In particular embodiments of said method wherein W is hydrogen, said cyclization using hydroxylamine is characterized by a step of converting the carbonyl group of the aforementioned group —CO—R$^8$ into an oxim using hydroxylamine, followed by a step of converting the hydroxy functionality of said oxim into a suitable leaving group (e.g. by acylation with Ac$_2$O), followed by intramolecular cyclization by heating either neat or under basic conditions (e.g. in the presence of K$_2$CO$_3$ or pyridine); a possible representation is found in Scheme 5, steps SP-5A and SP-5C.

In particular embodiments of the method for producing a compound according to the present invention, wherein W is

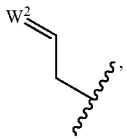

said transition metal mediated intramolecular alkylation at the position marked with an asterisk in the formula II' is accomplished by using a Palladium-based catalyst, more particularly Pd(OAc)$_2$, particularly in a polar non-protic solvent, more particularly in DMF, particularly at a temperature from 60 to 130° C., more particularly at about 80° C., even more particularly in DMF at about 80° C.

In other particular embodiments of the method for producing a compound according to the present invention, wherein W is

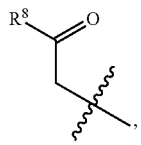

said transition metal mediated intramolecular alkylation at the position marked with an asterisk in the formula II' is accomplished by using a mixture of a Ni(II) and a Cr(II) salt, more particularly a mixture of nickel(II) chloride and chromium(II) chloride, particularly in a polar non-protic solvent, more particularly in DMF, particularly at a temperature from 100 to 150° C., more particularly at a temperature from 120 to 140° C., even more particularly in DMF at a temperature from 120 to 140° C.

In yet another particular embodiment, the method for producing a compound according to the present invention, wherein W is hydrogen, said transition metal mediated acylation at the position marked with an asterisk in the formula II' is accomplished by using a Palladium-based catalyst, more particularly PdCl$_2$(PPh$_3$)$_2$, and 1-ethoxyvinyl-tri-n-butyltin, particularly in a polar non-protic solvent, more particularly DMF, particularly at temperatures from 120 to 180° C., more particularly at about 160° C., even more particularly in DMF at about 160° C., yet even more particularly under microwave irradiation.

As used herein the terms disease, indication and medical condition are used interchangeably.

A further embodiment of the present invention is a compound of the present invention for use as a medicament. A further embodiment of the present invention is the use of a compound of the present invention for the manufacture of a medicament. A further embodiment of the present invention is a method of treatment, said method comprising administering a therapeutically effective amount of a compound of the present invention to a subject in need thereof.

It is to be understood that the embodiments of the present invention relating to a compound of the present invention, in particular for use in the treatment of disease or a medical condition, dosage form, application route, etc, as detailed herein, likewise relate to the use of a compound of the present invention for the manufacture of a medicament for use in the treatment of said diseases or medical conditions, as well as the methods of treating said diseases or medical conditions comprising administering a therapeutically effective amount of a compound of the present invention to a subject in need thereof.

In a particular embodiment, the present invention relates to a compound of the present invention for use in the treatment of a disease or medical condition in which the inhibition of the voltage-gated potassium channel Kv1.3 is beneficial, particularly for a disease or medical condition selected from the group consisting of psoriasis, psoriatric arthritis, autoimmune thyroiditis, Hashimoto's disease, Grave's disease, rheumatoid arthritis, vitiligo, Crohn's disease, ulcerative colitis, inflammatory bowel disease, ankylosing spondylitis (Morbus Bechterew), periodontal disease, diabetes type I, multiple sclerosis, systemic lupus erythematosus, anti-glomerular basement membrane glomerulonephritis, rapidly progressive glomerulonephritis, advanced chronic renal failure, chronic kidney disease, renal fibrosis, uveitis, pars planitis, asthma, pemphigus foliaceus, inclusion body myositis, dermatomyositis, scleroderma, Behcet disease, atopic dermatitis, allergic and irritant contact dermatitis, Lichen planus, Sjögren's syndrome, Graft-versus-Host-Reaction, Host-versus-Graft-Reaction, transplant rejection, end-stage renal disease, vascularized composite allotransplantation rejection, alopecia areata, inflammatory bone resorption disease, anti-neutrophil cytoplasmic autoantibody-associated vasculitis, osteoarthritis, diseases associated with intimal hyperplasia, breast cancer, leukemia, chronic lymphocytic leukemia, human lung adenocarcinoma, cutaneous T-cell lymphoma, osteosarcoma, neuroblastoma, ovarian cancer and melanoma, neuroinflammatory disorders, neurodegeneration, HIV-1-associated neurocognitive disorders (HAND), microglia-induced oxidative stress in Alzheimer's disease, obesity, and insulin resistance, restenosis/neointimal hyperplasia, atherosclerosis (arteriosclerotic vascular disease or ASVD), acute coronary syndrome, acute ischemic stroke, hypertension.

In a further particular embodiment, the present invention relates to a compound of the present invention for use in the treatment of a disease or medical condition in which the inhibition of the voltage-gated potassium channel Kv1.3 is beneficial, particularly for a disease or medical condition selected from the group consisting of psoriasis, psoriatic arthritis, autoimmune thyroiditis, Hashimoto's disease, Grave's disease, rheumatoid arthritis, vitiligo, Crohn's disease, inflammatory bowel disease, ulcerative colitis, diabetes type I, multiple sclerosis, systemic lupus erythematosus, anti-glomerular basement membrane glomerulonephritis, rapidly progressive glomerulonephritis, advanced chronic renal failure, chronic kidney disease, renal fibrosis, uveitis, pars planitis, asthma, pemphigus foliaceus, inclusion body myositis, dermatomyositis, scleroderma, allergic and irritant contact dermatitis, Sjögren's syndrome, Graft-versus-Host-Reaction, transplant rejection, end-stage renal disease, vascularized composite allotransplantation rejection, alopecia areata, inflammatory bone resorption disease, anti-neutrophil cytoplasmic autoantibody-associated vasculitis, diseases associated with intimal hyperplasia, breast cancer, leukemia, human lung adenocarcinoma, chronic lymphocytic leukemia, osteosarcoma, melanoma, neuroinflammatory disorders, neurodegeneration, HIV-1-associated neurocognitive disorders (HAND), microglia-induced oxidative stress in Alzheimer's disease, obesity, and insulin resistance, restenosis/neointimal hyperplasia, atherosclerosis (arteriosclerotic vascular disease or ASVD), acute coronary syndrome, acute ischemic stroke, hypertension.

In a further particular embodiment, the present invention relates to a compound of the present invention for use in the treatment of a disease or medical condition in which inhibition of Kv1.3 results in a (partial) immunosuppression, more particularly for an autoimmune disease or chronic inflammatory disease selected from the group consisting of psoriasis, psoriatric arthritis, autoimmune thyroiditis, Hashimoto's disease, Grave's disease, rheumatoid arthritis, vitiligo, Crohn's disease, ulcerative colitis, inflammatory bowel disease, ankylosing spondylitis, periodontal disease, diabetes type I, multiple sclerosis, systemic lupus erythematosus, anti-glomerular basement membrane glomerulonephritis, rapidly progressive glomerulonephritis, chronic kidney disease, uveitis, pars planitis, asthma, pemphigus foliaceus, inclusion body myositis, dermatomyositis, scleroderma, Behcet disease, atopic dermatitis, allergic and irritant contact dermatitis, Lichen planus, Sjögren's syndrome, Graft-versus-Host-Reaction, Host-versus-Graft-Reaction, transplant rejection, end-stage renal disease, vascularized composite allotransplantation rejection, alopecia areata, inflammatory bone resorption disease, anti-neutrophil cytoplasmic autoantibody-associated vasculitis, osteoarthritis, diseases associated with intimal hyperplasia, restenosis/neointimal hyperplasia, neuroinflammatory disorders, neurodegeneration, atherosclerosis (arteriosclerotic vascular disease or ASVD), hypertension.

In yet a further particular embodiment, the present invention relates to a compound of the present invention for use in the treatment of a disease or medical condition selected from the group consisting of psoriatric arthritis, autoimmune thyroiditis, Hashimoto's disease, Grave's disease, rheumatoid arthritis, Crohn's disease, ulcerative colitis, inflammatory bowel disease, ankylosing spondylitis, periodontal disease, diabetes type I, multiple sclerosis, systemic lupus erythematosus, anti-glomerular basement membrane glomerulonephritis, rapidly progressive glomerulonephritis, chronic kidney disease, uveitis, pars planitis, asthma, pemphigus foliaceus, inclusion body myositis, dermatomyositis, scleroderma, Behcet disease, atopic dermatitis, allergic and irritant contact dermatitis, Lichen planus, Sjögren's syndrome, Graft-versus-Host-Reaction, Host-versus-Graft-Reaction, transplant rejection, end-stage renal disease, vascularized composite allotransplantation rejection, alopecia areata, inflammatory bone resorption disease, anti-neutrophil cytoplasmic autoantibody-associated vasculitis, osteoarthritis, diseases associated with intimal hyperplasia, restenosis/neointimal hyperplasia, neuroinflammatory disorders, neurodegeneration, atherosclerosis (arteriosclerotic vascular disease or ASVD), hypertension.

In yet a further particular embodiment, the present invention relates to a compound of the present invention for use in the treatment of a disease or medical condition selected from the group consisting of psoriasis, rheumatoid arthritis, diabetes type I, multiple sclerosis, anti-glomerular basement membrane glomerulonephritis, rapidly progressive glomerulonephritis, advanced chronic renal failure, chronic kidney disease, renal fibrosis, allergic and irritant contact dermatitis, transplant rejection, asthma, end-stage renal disease, vascularized composite allotransplantation rejection, alopecia areata, inflammatory bone resorption disease, human lung adenocarcinoma, melanoma, neuroinflammatory disorders, neurodegeneration, obesity, and insulin resistance, restenosis/neointimal hyperplasia, atherosclerosis (arteriosclerotic vascular disease or ASVD), acute coronary syndrome.

In yet a further particular embodiment, the present invention relates to a compound of the present invention for use in the treatment of a disease or medical condition selected from the group consisting of rheumatoid arthritis, diabetes type I, multiple sclerosis, anti-glomerular basement membrane glomerulonephritis, rapidly progressive glomerulonephritis, advanced chronic renal failure, chronic kidney disease, renal fibrosis, allergic and irritant contact dermatitis, transplant rejection, asthma, end-stage renal disease, vascularized composite allotransplantation rejection, alopecia areata, inflammatory bone resorption disease, human lung adenocarcinoma, melanoma, neuroinflammatory disorders, neurodegeneration, obesity, and insulin resistance, restenosis/neointimal hyperplasia, atherosclerosis (arteriosclerotic vascular disease or ASVD), acute coronary syndrome.

In yet a further particular embodiment, the present invention relates to a compound of the present invention for use in the treatment of a disease or medical condition selected from the group consisting of psoriasis, atopic dermatitis, allergic and irritant contact dermatitis, rheumatoid arthritis, and uveitis, multiple sclerosis.

In yet a further particular embodiment, the present invention relates to a compound of the present invention for use in the treatment of a disease or medical condition selected from the group consisting of atopic dermatitis, allergic and irritant contact dermatitis, rheumatoid arthritis, and uveitis, multiple sclerosis.

In another particular embodiment, the present invention relates to a compound of the present invention for use in the treatment of a disease or medical condition in which inhibition of Kv1.3 results in an antiproliferative response, in particular a disease or medical condition selected from the group consisting of breast cancer, ovarian cancer, leukemia, chronic lymphocytic leukemia, osteosarcoma, neuroblastoma, human lung adenocarcinoma, melanoma, restenosis, neointimal hyperplasia.

In another particular embodiment, the present invention relates to a compound of the present invention for use in the treatment of a disease or medical condition in which inhibition of Kv1.3 results in a neuroprotective response, in particular for the treatment of neurodegeneration.

In another particular embodiment, the present invention relates to a compound of the present invention for use in the treatment of a disease or medical condition in which inhibition of Kv1.3 results in a modulation of cellular metabolism, in particular a disease or medical condition selected from the group consisting of obesity and insulin resistance.

In another particular embodiment, the present invention relates to a compound of the present invention for use in the treatment of a disease or medical condition treatable by inhibition of Kv1.3$^{high}$ phenotype cells, particularly Kv1.3$^{high}$ phenotype immune system cells, more particularly class-switched memory B-cells and/or effector memory T-cells of the Kv1.3$^{high}$ phenotype, even more particularly T-cell driven autoimmune disorders and chronic inflammation conditions, in particular selected from the group consisting of psoriatic arthritis, Type 1 diabetes, rheumatoid arthritis, multiple sclerosis, psoriasis, asthma, anti-glomerular basement membrane glomerulonephritis, acute coronary syndrome. In this context, Kv1.3$^{high}$ phenotype cells are cells wherein Kv1.3 expression numbers range from 750 to 2900, particularly 950 to 2900 Kv1.3 channels per cell, which can be determined either by immunohistochemical staining or patch-clamp analysis well known to the skilled person, and for example described in Wulff et al., *J. Clin. Invest.* 2003, 111, 1703; Rus et al., *PNAS* 2005, 102, 11094.

In the context of the present invention, whether the Kv1.3 expression in cells of a subject is high as defined herein, can particularly be determined by
1) obtaining a sample from said subject,
2) optionally isolating cells wherein Kv1.3 expression is to be determined from said sample,
3) optionally culturing said cells in a suitable medium,
4) determining the Kv1.3 expression in said cells,
wherein in particular cases
   said sample is a fluid sample, particularly a synovial or cerebrospinal fluid sample, leukapheresis sample, or peripheral blood sample, e.g. from a subject suspected of suffering from rheumatoid arthritis, or a tissue sample, particularly a sample from the affected tissue, such as a psoriatic lesion, synovial tissue or brain infiltrate, from said subject;

said cells wherein Kv1.3 expression is to be determined are particularly lymphocytes, B-cells, or T-cells, such as $T_{EM}$ cells; CD4$^+$ T-cells or CD8$^+$ T-cells;

said cells wherein Kv1.3 expression is to be determined are isolated by techniques known in the art, particularly density gradient centrifugation and FACS (fluorescence activated cell sorting), wherein in particular such isolation is used in the case of fluid samples;

said suitable medium is known in the art, e.g. Dulbecco's media, such as Iscove's modified Dulbecco's medium, which may be supplemented with the necessary additives, such as antibiotics;

in the case of tissue samples, the isolation and culturing may in certain cases be replaced by a step of sample preparation, e.g. paraffin preparation;

the Kv1.3 expression in said cells is determined via art-known techniques, particularly by patch-clamp, such as the patch-clamp techniques referenced herein, or by subjecting said cells to immunohistochemical staining and determining Kv1.3 expression by fluorescence microscopy, such as described in the literature references included herein, wherein the corresponding Kv1.3 expression in said cells may be calculated from the results obtained by the aforementioned techniques via art-known methods, such as described in the literature references included herein;

examples of such methods are described in e.g. PNAS 2006, 103, 17414; J. Clin. Invest. 2003, 111, 1703; J. Invest. Dermatol. 2011, 131, 118; PNAS 2005, 102, 11094.

The present invention further relates to pharmaceutical compositions, kits and kits-of-parts comprising a compound of the present invention.

The present invention further relates to the use of a compound of the present invention for the production of pharmaceutical compositions, and to pharmaceutical compositions comprising a compound of the present invention, which in further particular embodiments are employed for the treatment and/or prophylaxis of the diseases and/or medical conditions as disclosed herein.

In particular, the pharmaceutical compositions as described herein comprise a compound of the present invention and a pharmaceutically acceptable carrier or diluent.

Additionally, the invention relates to an article of manufacture, which comprises packaging material and a pharmaceutical agent contained within said packaging material, wherein the pharmaceutical agent is therapeutically effective against the medical conditions as described herein, and wherein the packaging material comprises a label or package insert which indicates that the pharmaceutical agent is useful for preventing or treating the medical conditions disclosed herein, and wherein said pharmaceutical agent comprises one or more compounds of the present invention. The packaging material, label and package insert otherwise parallel or resemble what is generally regarded as standard packaging material, labels and package inserts for pharmaceuticals having related utilities.

The pharmaceutical compositions of the present invention are prepared by processes which are known per se and familiar to the person skilled in the art. As pharmaceuticals, the compounds of the present invention can be either employed as such, or particularly in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content for example being from 0.1-99% or from 0.1-95% and where, by the appropriate choice of the auxiliaries and/or excipients, a pharmaceutical administration form (e.g. a delayed release form or an enteric form) suited to the active compound and/or to the desired onset of action to be achieved.

In particular embodiments, administration routes are selected from the group consisting of intravenous, oral, intramuscular, intraocular, topical, and enteral.

A customary dose of the compounds of the present invention in the case of systemic therapy (p.o.) is usually between 0.3 and 30 mg/kg per day, or between 0.3 and 100 mg/kg per day, (i.v.) is usually between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used in the pharmaceutical compositions of the present invention.

Depending upon the particular disease and/or medical condition to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known by the skilled person as appropriate for the disease being treated.

In a further aspect of the present invention, the compounds of the present invention, may be combined with standard therapeutic agents which are commonly used for the treatment of the medical conditions as described herein, more particularly selected from the group comprising, but not limited to methotrexate, corticosteroids like prednisone, prednisolone, methylprednisolone, dexamethasone, betamethasone, cortisone and the like; mycophenolate mofetil, tacrolimus, leflunomide or teriflunomide, cyclosporine A, cyclophosphamide, mitoxanthrone, fingolimod, azathioprine, glatiramer acetate, dimethyl fumarate, an IK-1 inhibitor like TRAM-34, a JAK-inhibitor like Tofacitinib or braticinip, a SYK-inhibitor like Fostamatinib, interferon-beta (IFN-β).

The person skilled in the art is aware on the base of his/her expert knowledge of the total daily dosage(s) and administration form(s) of the additional therapeutic agent(s) coadministered. Said total daily dosage(s) can vary within a wide range. In practicing the present invention and depending on the details, characteristics or purposes of their uses mentioned above, the compounds according to the present invention may be administered in combination therapy separately, sequentially, simultaneously or chronologically staggered (e.g. as combined unit dosage forms, as separate unit dosage forms or a adjacent discrete unit dosage forms, as fixed or nonfixed combinations, as kit-of-parts or as admixtures) with one or more standard therapeutics. In certain embodiments these standard therapeutics comprise art-known chemotherapeutic or target specific anti-cancer agents.

Thus, a further aspect of the present invention is a combination or pharmaceutical composition comprising a first active ingredient, which is a compound of the present invention or a salt or hydrate thereof, a second active ingredient, which is an art-known standard therapeutic for the medical conditions as described herein, and optionally a pharmacologically acceptable carrier, diluent and/or excipient for sequential, separate, simultaneous or chronologically staggered use in therapy in any order, e.g. to treat, prevent or ameliorate the diseases and/or medical conditions as described herein.

In this context, the present invention further relates to a combination comprising a first active ingredient, which is at least one compound according to the present invention, and a second active ingredient, which is at least one art-known standard therapeutic for the medical conditions as described herein, for separate, sequential, simultaneous or chronologically staggered use in therapy, such as e.g. in therapy of those diseases mentioned herein.

The term "combination" according to the present invention may be present as a fixed combination, a non-fixed combination or a kit-of-parts. A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The first and second active ingredient of a combination or kit-of-parts according to the present invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to the present invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to the present invention may together be a therapeutically effective amount for the treatment, prophylaxis or amelioration of a medical condition as described herein.

A further aspect of the present invention is a method for treating cotherapeutically the medical conditions as described herein, in a patient in need of such treatment comprising administering separately, sequentially, simultaneously, fixed or non-fixed a pharmacologically active and therapeutically effective and tolerable amount of one or more of the compounds according to the present invention and a pharmacologically active and therapeutically effective and tolerable amount of one or more art-known therapeutic agents for the medical conditions as described herein, to said patient.

For the production of the pharmaceutical compositions, the compounds of the present invention are suitably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions. The pharmaceutical compositions according to the invention are prepared by processes known per se.

As used herein, the term "room temperature" or "r.t." usually refers to about 25° C.

Analytical Devices Used

Analytical LC/ESI-MS: Waters 2700 Autosampler. Waters 1525 Multisolvent Delivery System. 5 µL sample loop. Column, Phenomenex Onyx Monolythic C18 50×2 mm, with stainless steel 2 µm prefilter. Eluent A, $H_2O$+0.1% HCOOH; eluent B, MeCN. Gradient, 5% B to 100% B within 3.80 min, then isocratic for 0.20 min, then back to 5% B within 0.07 min, then isocratic for 0.23 min; flow, 0.6 ml/min and 1.2 ml/min.

Waters Micromass ZQ 4000 single quadrupol mass spectrometer with electrospray source. MS method, MS4_15minPM-80-800-35V; positive/negative ion mode scanning, m/z 80-800 in 0.5 s; capillary voltage, 3.50 kV; cone voltage, 50 V; multiplier voltage, 650 V; source block and desolvation gas temperature, 120° C. and 300° C., respectively. Waters 2487 Dual λ Absorbance Detector, set to 254 nm. Software, Waters Masslynx V 4.0.

Waters Micromass LCZ Platform 4000 single quadrupol mass spectrometer with electrospray source. MS method, MS4_15minPM-80-800-35V; positive/negative ion mode scanning, m/z 80-800 in 1 s; capillary voltage, 4.0 kV; cone voltage, 30 V; multiplier voltage, 900 V; source block and desolvation gas temperature, 120° C. and 300° C., respectively. Waters 996 Photodiode Array Detector, set 200 to 400 nm. Software, Waters Masslynx V4.0.

Values for $[M+H]^+$ given in the examples are those found within the corresponding LC/MS chromatogram for the respective compound. These values were all found within tolerable margins of +/−0.3 units compared to calculated exact mass upon protonation of the compound.

Preparative thinlayer chromatography (preparative TLC): Merck PLC plates, silica gel 60 $F_{254}$, 0.5 mm, 1.0 mm or 2.0 mm.

Column chromatography: Acros silica gel 60A, 0.035-0.070 mm.

Preparative HPLC-MS: Waters 2767 Autosampler, Waters 600 Multisolvent Delivery System with analytical pump heads (100 µL); Waters 600 Controller; Waters 2525 Binary Gradient Modul with preparative pump heads (500 µL). At-Column-Dilution: solvent1, MeCN:$H_2O$ 70:30 (v/v), solvent2, MeCN:MeOH:DMF 80:15:5 (v/v/v); flow rate, 5 mL/min. Autosampler 2767 with 10 mL syringe and 10 mL Sample loop. Column 6-position valve Flom 401 with Waters X-Terra RP18, 5 µm, 19×150 mm with X-Terra RP18 guard cartridge 5 µm, 19×10 mm, used at flow rate 20 mL/min; Waters SunFire Prep OBD 5 µm, 30×50 mm with SunFire RP18 guard cartridge 5 µm, 19×10 mm, used at flow rate 25 mL/min; Waters Atlantis Prep T3 OBD 5 µm, 30×50 mm with Atlantis guard cartridge, used at flow rate 50 mL/min; Waters X-Bridge Prep OBD 5 µm, 19×150 mm with X-Bridge RP18 guard cartridge 5 µm, 19×10 mm used at flow rate 20 mL/min; Waters Atlantis Prep T3 OBD 5 µm, 19×50 mm with Atlantis guard cartridge, used at flow rate 25 mL/min and YMC-Actus Hydrosphere C18 5 μm, 20×50 mm with Actus guard cartridge, used at flow rate 20 mL/min. Eluent A, H$_2$O containing 0.1% (v/v) HCO$_2$H or H$_2$O containing 0.1% (v/v) NEt$_3$; eluent B, MeCN. Different linear gradients, individually adapted to sample. Injection volume, 9 mL, depending on sample. Make-up solvent, MeOH-MeCN—H$_2$O—HCO$_2$H 80:15:4.95:0.05 (v/v/v/v). Make-up pump, Waters Reagent Manager, flow rate 0.5 mL/min. Waters ZQ single quadrupole mass spectrometer with electrospray source. Positive or negative ion mode scanning m/z 105-950 in 1 s; capillary, 3.6 kV; cone voltage, 45 V; multiplier voltage, 700 V; probe and desolvation gas temperature, 120° C. and 250° C., respectively. Waters Fraction Collector 2767 with mass or UV-triggered fraction collection. Waters 2487 Dual λ Absorbance Detector, set to 254 nm. Software, Waters Masslynx V 4.0 SP4.

$^1$H NMR spectra were recorded at room temperature on a Bruker Supraleitendes Fourier NMR Spektrometer, Avance™ 300 MHz. Chemical shifts δ are reported in ppm. Multiplicity of a certain signal (singlet, doublet, triplet, quartet, multiplet) is indicated by the respective abbreviation (s, d, t, q, m respectively). "br s" indicates a broad singlet, "m$_C$" a centered multiplet. The solvent residual signals were used as internal standards: δ(CDCl$_3$)=7.26, δ(d6-DMSO)=2.50, δ(CD$_3$OD)=3.31, δ(d6-acetone)=2.05. Eluents for Preparative TLC or Column Chromatography (CC) on Silica Gel:

Eluent1: petroleum ether/CH$_2$Cl$_2$/MeOH; Eluent2: CH$_2$Cl$_2$/MeOH; Eluent3: petroleum ether/ethyl acetate; for each eluent, the aforementioned solvents were used in different ratios, depending on the respective compound Standard Protocols and Syntheses of Building Blocks:

If not commercially available, required β-ketoesters b1 (Scheme 1) were synthesized via Claisen condenzation from appropriately substituted benzoic acid esters and respective alpha-substituted acetic acid esters according to Taber et al., *J. Org. Chem.* 1995, 60, 1093 and Muiller et al., *Helvetica Chim. Acta* 1998, 81, 317, the synthetis protocols of which are incorporated herein by reference. The desired building blocks were obtained in the β-ketoester tautomeric form as the sole or major component, accompanied in most cases by their tautomeric form alkyl 3-hydroxy-3-aryl-2-propenoate: ethyl 3-(2-fluorophenyl)-2-methyl-3-oxopropanoate, ethyl 3-(2-ethoxyphenyl)-2-methyl-3-oxopropanoate, ethyl 3-(2-methoxyphenyl)-2-methyl-3-oxopropanoate, ethyl 3-(3-methoxyphenyl)-2-methyl-3-oxopropanoate, ethyl 2-methyl-3-oxo-3-phenylpropanoate, methyl 3-(2-chlorophenyl)-2-methyl-3-oxopropanoate, ethyl 2-methyl-3-oxo-3-(pyridin-3-yl)propanoate, methyl 3-(2-methoxypyridin-3-yl)-2-methyl-3-oxopropanoate, methyl 3-(4-methoxypyridin-3-yl)-2-methyl-3-oxopropanoate, methyl 2-methyl-3-(o-tolyl)-3-oxopropanoate.

Exemplarily given is the NMR for ethyl 2-methyl-3-oxo-3-phenylpropanoate, which was obtained only within the β-ketoester form: $^1$H NMR (300 MHz, CDCl$_3$): δ=1.16 (3H, t, OEt), 1.49 (3H, d, Me), 4.15 (2H, q, OEt), 4.37 (1H, q, CH), 7.47 (2H, tt, Ar—H), 7.58 (1H, tt, Ar—H), 7.98 (2H, dt, Ar—H). Likewise exemplarily given is the NMR for methyl 3-(2-chlorophenyl)-2-methyl-3-oxopropanoate, which was obtained as a 3:2 mixture with its tautomer: $^1$H NMR (300 MHz, CDCl$_3$): δ=1.48 (3H, d, Me, keto), 1.59 (3H, s, Me, enol), 3.68 (3H, s, OMe, keto), 3.85 (3H, s, OMe, enol), 4.35 (1H, q, CH, keto), 7.30-7.49 (4H keto+4H enol, m, Ar—H), 12.57 (1H, s, OH, enol).

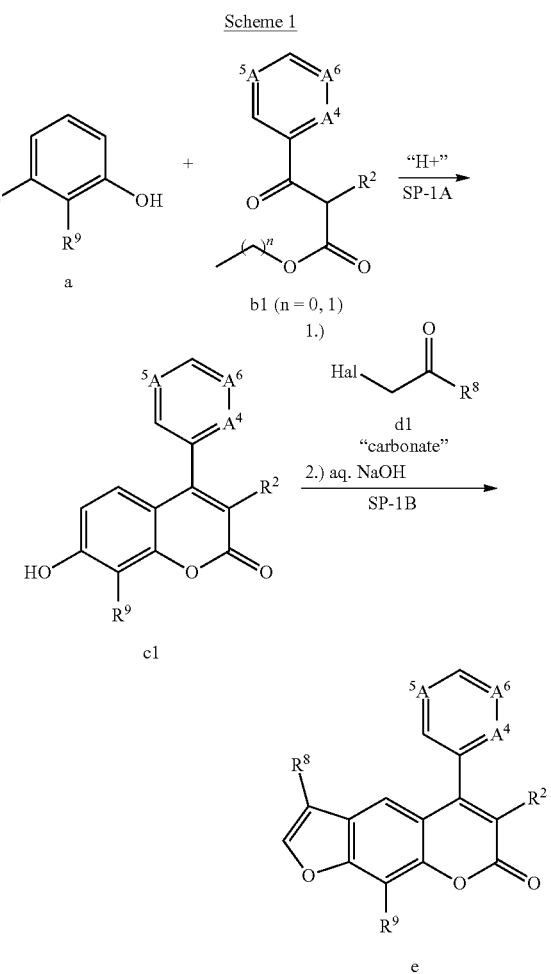

Scheme 1

Standard Procedure 1 (SP-1): Synthesis of Furocoumarins (Cf. Scheme 1)

SP-1A (adapted from *J. Org. Chem.* 1962, 27, 3703): The respective resorcinol a (0.36 to 4.0 mmol, 1.0 eq.) was treated with the respective β-ketoester b1 (1.0 eq.) and trifluoroacetic acid (1-2 mL/mmol) under reflux overnight. The reaction was quenched by addition of iced water. The mixture was extracted thrice with ethyl acetate, combined organic phases were washed once with aq. NaHCO$_3$ (5%) and dried over MgSO$_4$ to give crude coumarin c1.

SP-1B (adapted from *Heterocyclic Commun.* 1997, 3, 339; *Chem. Nat. Comp.* 2000, 36, 478; *Chem. Nat. Comp.* 2002, 38, 539): Equivalents (eq.) are referred to with respect to the amount of resorcinol used in SP-1A.

1$^{st}$ Step:

The crude coumarin c1 was dissolved in acetone (10 mL/mmol; for larger scale, 5 mL/mmol were used), K$_2$CO$_3$ (2.0 e.q), NaI (0.3 eq.) and the respective alpha-halo-ketone d1 (1.6 eq.) were added, and the mixture stirred under reflux overnight. Salts were filtered off, the cake was washed with acetone and the filtrate was concentrated to dryness.

2$^{nd}$ Step:

The crude mixture was taken up in iPrOH (3-10 mL/mmol) and treated with 1.0 N aq. NaOH (3-10 mL/mmol) at 80° C. for 5 h. The mixture was cooled to room temperature and acidified with 5% aq. HCl (to pH 1-2). Further H$_2$O was added and the resulting suspension was stored at about 4° C. overnight. Depending on the outcome, either a precipitate was filtered off and washed with 5% aq. NaHCO$_3$, deionized water and finally with Et$_2$O (SP-1B-1) or in the case of a cloudy mixture, said mixture was extracted with ethyl acetate or CH$_2$Cl$_2$, the combined organic phases were washed with saturated aq. NaHCO$_3$, dried over MgSO$_4$ and purified by preparative TLC or column chromatography on silica gel for larger scale syntheses (SP-1B-2) to give furocoumarins e.

Bromination of 3,9-dimethyl-5-phenyl-7H-furo[3,2-g]chromen-7-one (e1)

(e1) (3.4 mmol) was dissolved in CH$_2$Cl$_2$ and AcOH (each 4.5 mL/mmol). N-Bromosuccinimide (1.2 eq., in CH$_2$Cl$_2$, 2 mL/mmol) was added, and the mixture was stirred at r.t. for 1 h, and then diluted with CH$_2$Cl$_2$ and washed with 5% aq. NaHCO$_3$. The organic phase was dried over MgSO$_4$, filtered and concentrated in vacuo. If necessary, the residue was

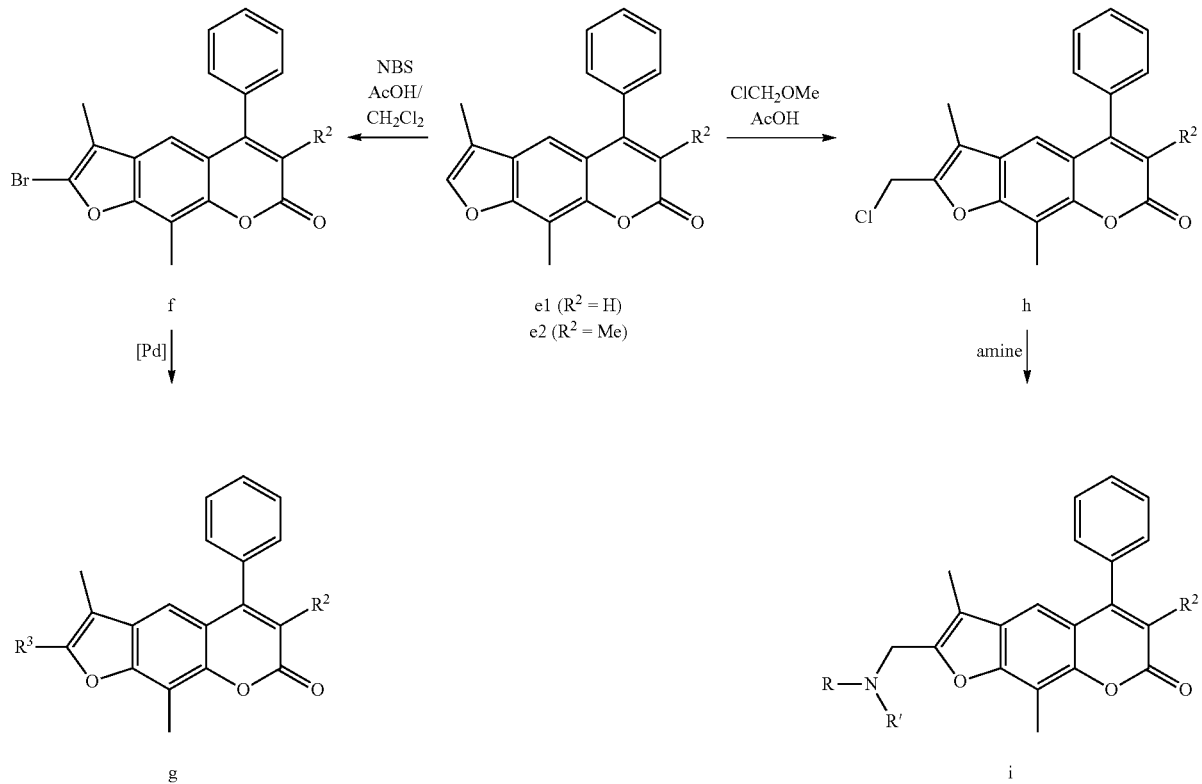

Scheme 2 purified by preparative TLC (CH$_2$Cl$_2$ 100%); 84-96% yield. 2-bromo-3,9-dimethyl-5-phenyl-7H-furo[3,2-g]chromen-7-one (f): LC/MS [M+H]$^+$: 368.90; H NMR (300 MHz, CDCl$_3$): =2.11 (3H, d, Me), 2.63 (3H, s, Me), 6.33 (1H, s, Ar—H), 7.29 (1H, s, Ar—H), 7.45-7.51 (2H, m, Ar—H), 7.53-7.61 (3H, m, Ar—H).

Chloromethylation of 3,9-dimethyl-5-phenyl-7H-furo[3,2-g]chromen-7-one (e1)

Chloromethyl methyl ether (25 eq.) was added to a solution of (e1) (3.4 mmol) in HOAc (22 mL/mmol), and stirred at r.t. overnight. Additional chloromethyl methyl ether (25 eq.) was added and the mixture stirred at r.t. for further 24 h, then poured onto an ice/water mixture, and the resulting precipitate was filtered off, washed with water and dried. Crude product was purified by silica gel column chromatography (eluent3—4:1); 11% yield. 2-(chloromethyl)-3,9-dimethyl-5-phenyl-7H-furo[3,2-g]chromen-7-one (h): LC/MS [M+H]$^+$: 338.86; 1H NMR (300 MHz, CDCl$_3$): δ=2.19 (3H, d, Me), 2.65 (3H, s, Me), 4.72 (2H, s, CH$_2$), 6.33 (1H, s, Ar—H), 7.35 (1H, s, Ar—H), 7.39-7.51 (2H, m, Ar—H), 7.52-7.58 (3H, m, Ar—H).

3,9-dimethyl-5-phenyl-7H-furo[3,2-g]chromen-7-one (e1) was synthesized according to SP-1A using 2-methylresorcinol and ethyl benzoylacetate; 53% yield (30 mmol; the product precipitated upon cooling the reaction mixture to r.t., was filtered off and washed with water and MeOH, or the reaction mixture was diluted with water and extracted with ethyl acetate) and SP-1B-1 (using chloroacetone d2; final purification by silica gel column chromatography, from 100% petroleum ether to eluent3-6:4, and re-crystallization from MeOH).

7-hydroxy-8-methyl-4-phenyl-2H-chromen-2-one (c1, Scheme 1): $^1$H NMR (300 MHz, d$_6$-DMSO): δ=2.21 (3H, d, Me), 6.12 (1H, s, Ar—H), 6.84 (1H, d, Ar—H), 7.11 (1H, d, Ar—H), 7.45-7.59 (5H, m, Ar—H), 10.49 (1H, s, OH).

3,9-dimethyl-5-phenyl-7H-furo[3,2-g]chromen-7-one (e1): LC/MS [M+H]$^+$: 290.93; $^1$H NMR (300 MHz, CDCl$_3$): δ=2.16 (3H, d, Me), 2.63 (3H, s, Me), 6.31 (1H, s, Ar—H), 7.37 (1H, s, Ar—H), 7.45 (1H, m, Ar—H), 7.47-7.51 (2H, m, Ar—H), 7.52-7.58 (3H, m, Ar—H). $^1$H NMR (300 MHz, d$_6$-DMSO): δ=2.12 (3H, d, Me), 2.53 (3H, s, Me), 6.34 (1H, s, Ar—H), 7.37 (1H, s, Ar—H), 7.56-7.62 (5H, m, Ar—H), 7.88 (1H, m, Ar—H).

Scheme 3

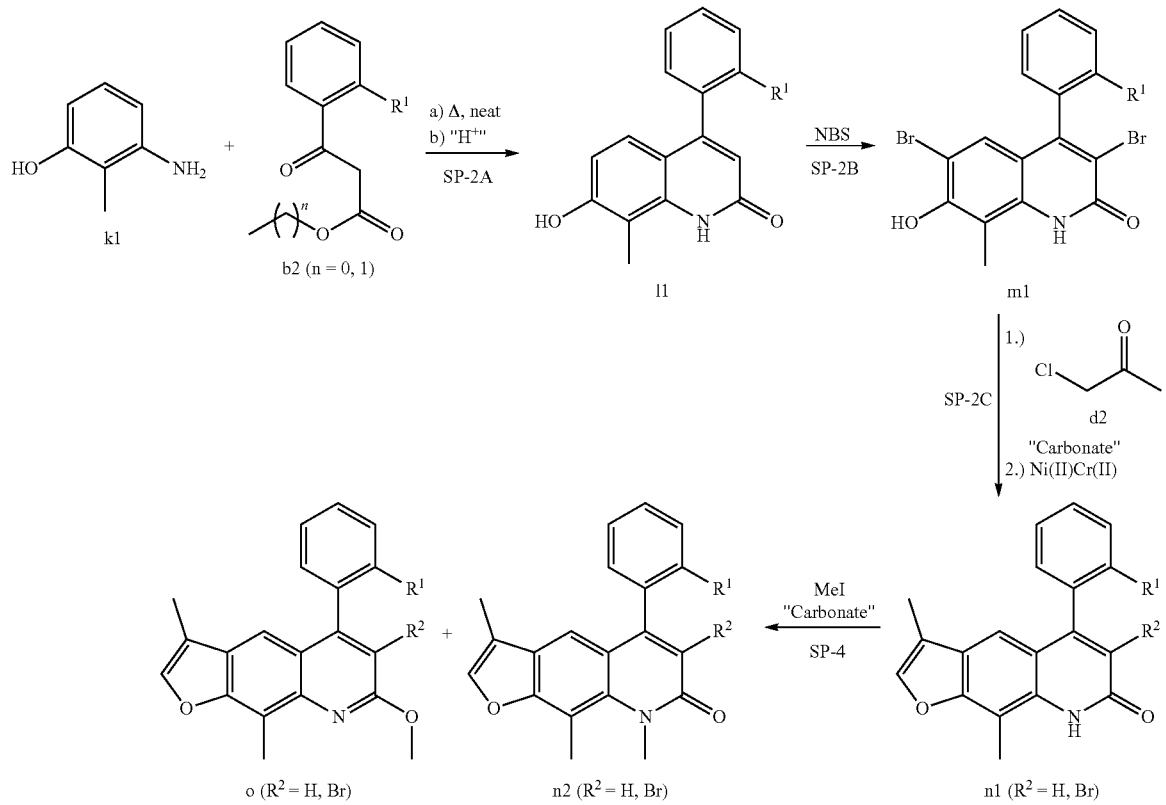

Standard Procedure 2 (SP-2): Synthesis of Furoquinolones (Cf. Scheme 3)

SP-2A

3-Amino-o-cresol (k1) (1.0 eq.) and the respective methyl/ethyl 3-aryl-3-oxo-propanoate b2 (1.0 eq.) were mixed and heated at 145° C. for 5 h to give predominantly N-(3-hydroxy-2-methylphenyl)-3-oxo-3-arylpropanamide, which was then cyclized by treatment of the slurry with TFA (2.5 mL/mmol) for 1-3 h at 72° C. Addition of an ice/water mixture resulted in precipitation, which was filtered off and washed with water to give crude 7-hydroxy-8-methyl-4-arylquinolin-2(1H)-one l1 (SP-2A-1). In an alternative workup (SP-2A-2), the mixture was partitioned between water and ethyl acetate, combined organic phases were washed with brine and dried over $MgSO_4$, and the crude product was purified by column chromatography (eluent3, 1:1).

SP-2B 7-hydroxy-8-methyl-4-arylquinolin-2(1H)-one l1 (1.0 eq.) was suspended in $CH_2Cl_2$ (5 mL/mmol) and DMSO (0.75 mL/mmol) and cooled to −10° C. Diisopropylamine (0.5 eq.) was added, followed by a dropwise addition of N-bromosuccinimide [NBS; 1.0 eq., dissolved in $CH_2Cl_2$ (2.5 mL/mmol) and DMSO (0.38 mL/mmol)]. This solution was stirred at −10° C. for 1 h, before NBS was added slowly again [0.5 eq., dissolved in $CH_2Cl_2$ (2.5 mL/mmol) and DMSO (0.38 mL/mmol)]. The latter step was repeated once more, before the mixture was partitioned between $CH_2Cl_2$ and 0.5 M aq. HCl. Combined organic phases were washed with saturated aq. $NaHCO_3$ and dried over $MgSO_4$. Chromatography on silica gel gave 3,6-dibromo-7-hydroxy-8-methyl-4-arylquinolin-2(1H)-one m1.

SP-2C ($1^{st}$ step adapted from *J. Med. Chem.* 2004, 47, 6392 and *Chem. Pharm. Bull.* 1983, 852)

$1^{st}$ Step:

3,6-dibromo-7-hydroxy-8-methyl-4-arylquinolin-2(1H)-one m1 (1.0 eq.) was dissolved in iPrOH (5 mL/mmol) and 1,8-diazabicyclo[5.4.0]undec-7-ene (1.5 eq.) and treated with chloroacetone (d2) (1.2 eq.) at 80° C. for 2.5 h. In case of incomplete conversion, the aforementioned quantities of DBU and chloroacetone (d2) were added again and stirring was continued at 80° C. for 1.5 h. The mixture was partitioned between $CH_2Cl_2$ or ethyl acetate and water. Combined organic phases were washed with citric acid (5%, aq.) and brine and dried over $MgSO_4$. Isolation of 3,6-dibromo-8-methyl-7-(2-oxopropoxy)-4-arylquinolin-2(1H)-one was achieved by chromatography on silica gel.

$2^{nd}$ Step:

3,6-dibromo-8-methyl-7-(2-oxopropoxy)-4-arylquinolin-2(1H)-one (1.0 eq.) was dissolved in DMF (30 mL/mmol) in an argon atmosphere. Nickel(II) chloride (0.33 eq.) and chromium(II) chloride (10 eq.) were added and the mixture was stirred at 125° C. for 1-2 h. Salts were removed by filtration, the filter cake was washed with DMF. The filtrate was partitioned between $CH_2Cl_2$ or ethyl acetate and 1.0 M aq. HCl. Combined organic phases were washed with brine and dried over $MgSO_4$. Purification was achieved by preparative TLC (eluent1—4:6:1) to usually give 3,9-dimethyl-5-arylfuro[3,2-g]quinolin-7(8H)-one n1 ($R^2$=H) as the major product and 6-bromo-3,9-dimethyl-5-arylfuro[3,2-g]quinolin-7(8H)-one n1 ($R^2$=Br) as a minor by-product.

Scheme 4

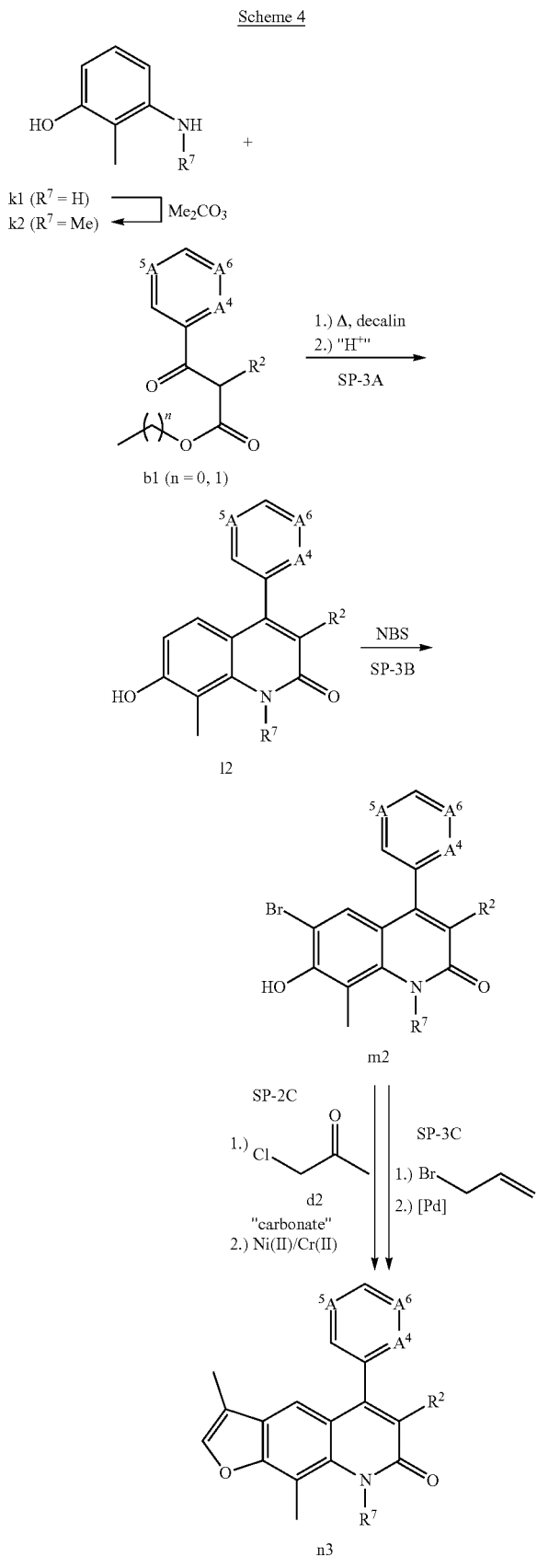

Standard Procedure 3 (SP-3): Synthesis of Furoquinolones (Cf. Scheme 4)

SP-3A

1st Step:

The respective methyl/ethyl 3-aryl-2-methyl-3-oxopropanoate or methyl/ethyl 3-aryl-3-oxopropanoate b1 (1.1 eq.) was dissolved in trans-decahydronaphthalene (1 mL/mmol; =trans-decalin). The respective 3-amino-o-cresol k1 or k2 (1.0 eq.) was added, and the resulting mixture was stirred for 5-10 h at 170° C. Upon cooling to room temperature, the solvent was decanted, and the residue was washed with petroleum ether. The resulting 3-aryl-N-(3-hydroxy-2-methylphenyl)-3-oxopropanamide was dried in vacuo.

2nd Step:

3-aryl-N-(3-hydroxy-2-methylphenyl)-3-oxopropanamide was cyclized in TFA (3 mL/mmol) for 2 h at 72° C. TFA was removed under reduced pressure, and the residue was partitioned between water and ethyl acetate. Combined organic layers were washed with saturated aq. $NaHCO_3$ and brine, dried over $Na_2SO_4$ and concentrated in vacuo. The respective intermediate 4-aryl-7-hydroxy-8-methylquinolin-2(1H)-one 12 was purified by chromatography on silica gel.

SP-3B 4-aryl-7-hydroxy-8-methylquinolin-2(1H)-ones 12 with various substituents in position 3 were dissolved in $CH_2Cl_2$/DMSO (2:1; 5 mL/mmol) and cooled to 0° C. A solution of NBS (1.4 eq.) in DMSO (0.35 mL/mmol NBS) was added, and the resulting mixture was stirred for 1 h at 0° C. If a reaction control by TLC indicated incomplete conversion, additional NBS (1.4 eq.) was added as solid in one portion, and stirring was continued for 1 h at 0° C. The reaction mixture was quenched with saturated aq. $Na_2SO_3$, diluted with water and extracted with EtOAc. Combined organic layers were washed with 1 N aq. HCl and brine, dried over $Na_2SO_4$ and concentrated in vacuo to afford the respective crude 3-substituted-6-bromo-4-aryl-7-hydroxy-8-methylquinolin-2(1H)-ones m2.

SP-3C

1st Step:

Differently 3-substituted-6-bromo-4-aryl-7-hydroxy-8-methylquinolin-2(1H)-ones m2 (1.0 eq.) were suspended in iPrOH (6.0 mL/mmol). DBU (1.8 eq.) and allyl bromide (1.7 eq.) were added, and the resulting mixture was heated to 80° C. for 2 h. The reaction mixture was diluted with water and the resulting precipitate was filtered off, washed with water and dried in vacuo to give the respective crude O-allylated compound. If insufficient precipitation occurred, the mixture (or alternatively supernatant and rinsing solutions from precipitation) was partitioned between $H_2O$ and $CH_2Cl_2$.

2nd Step:

The respective crude 7-(allyloxy)-6-bromo-8-methyl-4-phenylquinolin-2(1H)-one derivate (1.0 eq.), tetrabutylammonium chloride hydrate (1.1 eq.), sodium formiate (1.0 eq.), $Na_2CO_3$ (2.5 eq.) and $Pd(OAc)_2$ (0.2 eq.) were placed in a screw cap vial. DMF (20 mL/mmol) was added, and the resulting mixture was degassed by bubbling argon through the solution. The mixture was then stirred at 90° C. under an argon atmosphere for 1-16 h. The mixture was diluted with water and extracted with EtOAc. The combined organic layers were washed with 1 N aq. NaOH and brine, dried over $Na_2SO_4$ and concentrated in vacuo. The respective product n3 was purified by chromatography on silica gel.

SP-4 (Cf. Scheme 3): N/O-Methylation of Furoquinolones

The respective 3,9-dimethyl-5-phenylfuro[3,2-g]quinolin-7(8H)-one (bearing different 6-substituents) n1 (1.0 eq.) was dissolved in DMF (1 mL/0.1 mmol). $K_2CO_3$ (3.0 eq.) and iodomethane (2.5 eq.) were added, and the mixture was heated to 90° C. for 2 h. The suspension was filtered, the filter cake was washed with ethyl acetate, and the filtrate was extracted with citric acid (5%, aq.) and brine. The organic phase was dried over MgSO₄ and product isolation (n2 and o) was achieved by preparative TLC (eluent1—10:6:1).

with saturated NaHCO₃, dried over Na₂SO₄ and concentrated in vacuo. Crude product (potentially further substituted 7-acetoxy-8-methyl-4-aryl-2H-chromen-2-one or 7-acetoxy-8-methyl-4-arylquinolin-2(1H)-one) was directly used for the subsequent Fries rearrangement Scheme 5

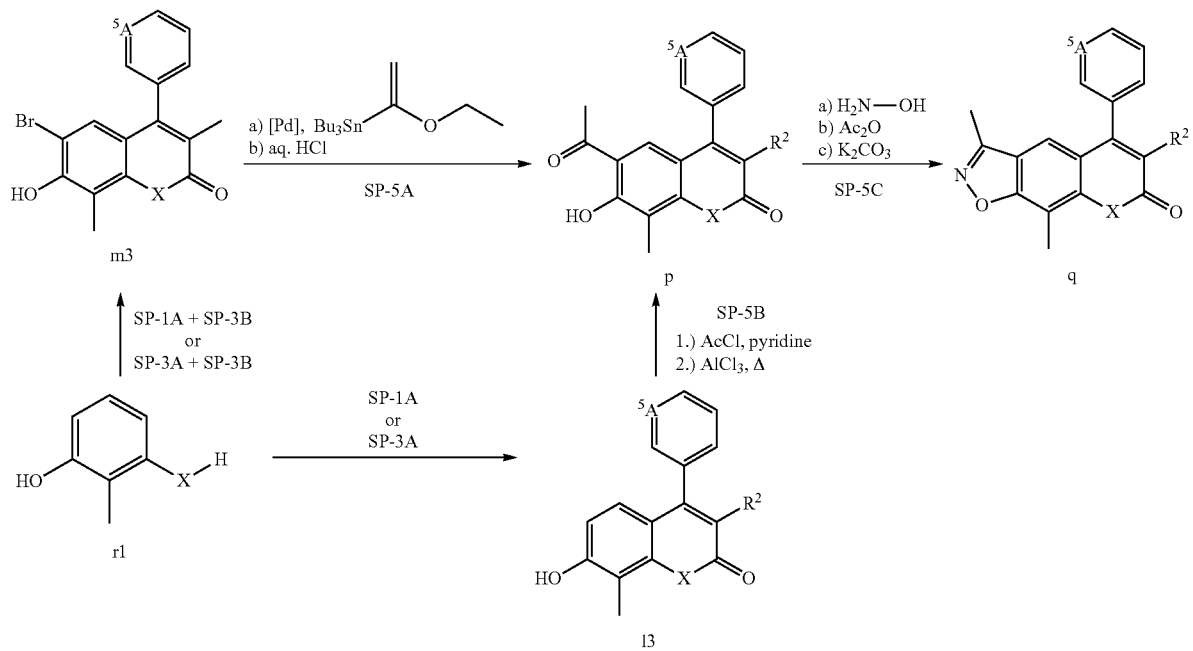

SP5: Synthesis of Isoxazolocoumarins and Isoxazoloquinolones (Cf. Scheme 5)

SP-5A:
6-bromo-7-hydroxy-3,8-dimethyl-4-aryl-2H-chromen-2-one or differently N-substituted 6-bromo-7-hydroxy-3,8-dimethyl-4-arylquinolin-2(1H)-one m3 (1.0 eq.) and PdCl₂(PPh₃)₂ (0.15 eq.) were placed in a microwave vial. DMF (4.0 mL/mmol) and 1-ethoxyvinyl-tri-n-butyltin (1.1 eq.) were added, and the resulting mixture was heated in the microwave to 160° C. for 15 min. Additional PdCl₂(PPh₃)₂(0.05 eq.) and 1-ethoxyvinyl-tri-n-butyltin (0.5 eq.) were added, and the mixture was again heated in the microwave to 160° C. for 15 min. 1 N aq. HCl was added, and the mixture was stirred at rt. for 30 min. After dilution with water, the mixture was extracted with EtOAc. Combined organic layers were washed with water and brine, dried over Na₂SO₄ and concentrated in vacuo. The residue was purified by chromatography on silica gel to give the respective 6-acetyl derivative p.

SP-5B: (Alternative to SP-5A: Fries Rearrangement)
1$^{st}$ Step:
The respective and potentially further substituted 7-hydroxy-8-methyl-4-aryl-2H-chromen-2-one or 7-hydroxy-8-methyl-4-arylquinolin-2(1H)-one 13 (1.0 eq.) was dissolved in pyridine (3 mL/mmol). Acetyl chloride (2.0 eq.) was added, and the resulting mixture was stirred at rt. for 18 h. If a reaction control by TLC showed incomplete conversion, additional acetyl chloride (2.0 eq.) was added, and stirring was continued at rt. for 17 h. In case of poor solubility of the starting material, NMP might be added. The reaction mixture was diluted with water and extracted with CH₂Cl₂ or ethyl acetate. The combined organic layers were washed 2$^{nd}$ Step (in Analogy to *J. Ind. Chem. Soc.* 1969, 46, 1014 and *ARKIVOC* 2000, 6, 931):
The respective and potentially further substituted 7-acetoxy-8-methyl-4-aryl-2H-chromen-2-one or 7-acetoxy-8-methyl-4-arylquinolin-2(1H)-one (1.0 eq.) and AlCl₃ (5.0 eq.) were heated neat to 170° C. (the mixture became liquid/oily at approximately 145° C.) and stirred at this temperature for 2.5 h. The reaction mixture was cooled to room temperature and treated with 1 N aq. HCl (sonication). The resulting suspension was diluted with water and extracted with CH₂Cl₂ or ethyl acetate. The combined organic layers were dried over Na₂SO₄ and concentrated in vacuo. The residue was purified by preparative TLC (eluent2) to give the respective, optionally further substituted 6-acetyl-7-hydroxy-8-methyl-4-aryl-2H-chromen-2-one or 6-acetyl-7-hydroxy-8-methyl-4-arylquinolin-2(1H)-one derivative p.

SP-5C:
The respective, optionally further substituted 6-acetyl-7-hydroxy-8-methyl-4-aryl-2H-chromen-2-one or 6-acetyl-7-hydroxy-8-methyl-4-arylquinolin-2(1H)-one derivative p (1.0 eq.), H₂NOH.HCl (5.0 eq.) and NaAc (5.0 eq.) were suspended in MeOH (7 mL/mmol) and heated under reflux for 3 h, then concentrated, and the residue was partitioned between water and EtOAc. The aqueous layer was extracted with EtOAc. Combined organic layers were washed with water and brine, dried over Na₂SO₄ and concentrated in vacuo. The resulting crude product was suspended in acetic anhydride (7.0 mL/mmol), and CH₂Cl₂, dioxane, DMF or NMP was added to improve solubility. The mixture was stirred at rt. for 24 h. The reaction mixture was diluted with water and stirred for 15 min. If a precipitate was formed, it was filtered off, washed with water and taken up in $CH_2Cl_2$. This organic phase was dried over $Na_2SO_4$. If no or insufficient precipitation occurred, the mixture was extracted with ethyl acetate, the combined organic layers were washed with saturated aq. $NaHCO_3$ and brine and dried over $Na_2SO_4$. In either of the aforementioned cases, the solvent was removed in vacuo and the resulting intermediate was cyclized by treatment with $K_2CO_3$ (2.2 eq.) in a toluene suspension (7 mL/mmol) at 110° C. for 2 h. Toluene was removed in vacuo. The residue was suspended in $CH_2Cl_2$ and filtered. The filtrate was concentrated, and the residue was purified by silica gel chromatography to yield the desired product q.

Scheme 6

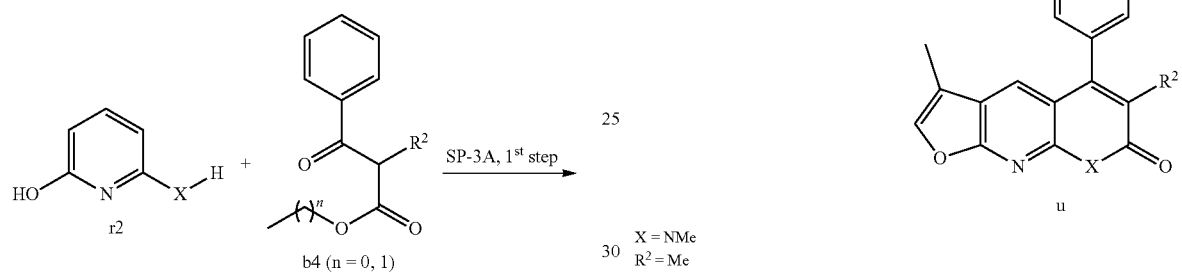

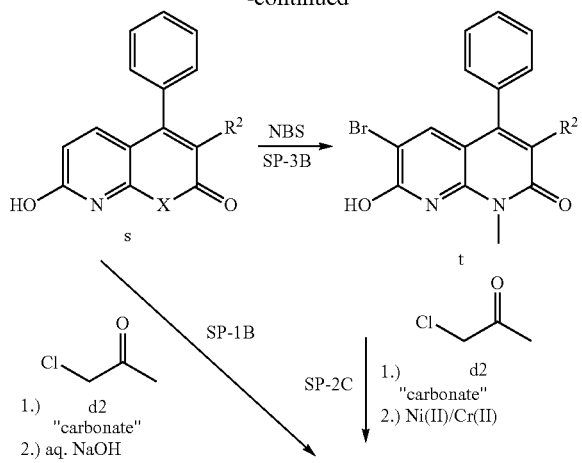

Scheme 7

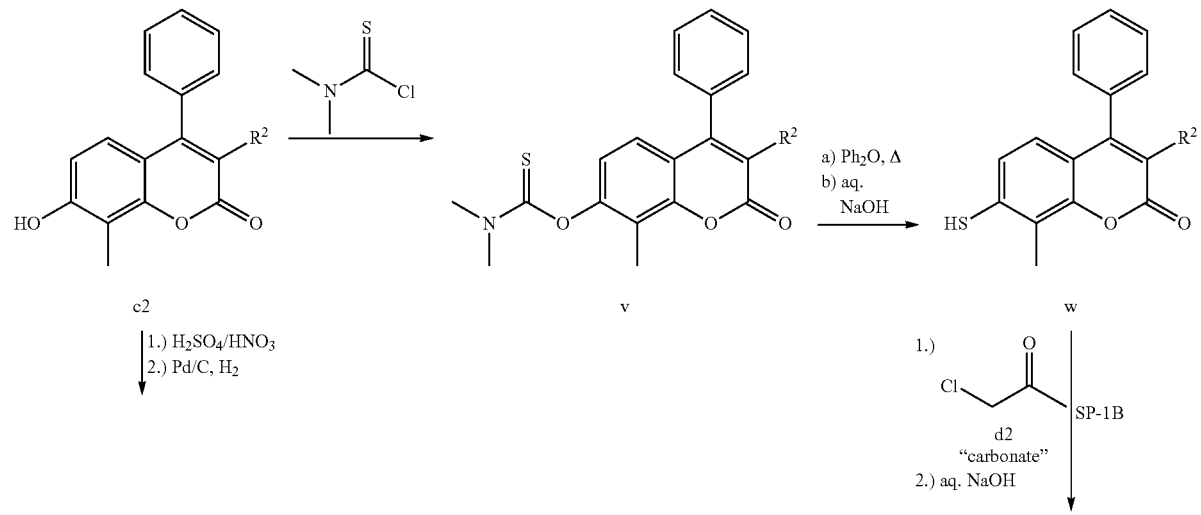

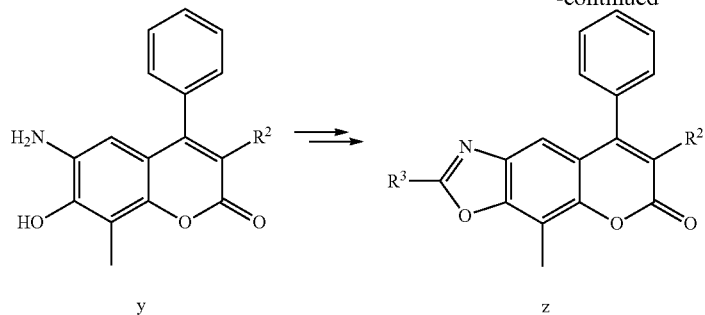

y    z

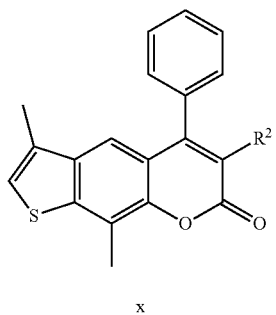

x

EXAMPLES OF COMPOUNDS OF THE PRESENT INVENTION

Most synthetic procedures are referring to the above Standard Procedures (SP). Where applicable, deviations from the SP are detailed in parentheses, whereas unmentioned steps have been performed in accordance with the SP protocol and are thus not named explicitly again.

Note that examples 26-34, 36, 40, 49, 51, 52, 54-56, 59-61 and 64 are not part of the present invention and serve as illustrative examples.

Example 1: 5-(2-methoxyphenyl)-3,9-dimethyl-7H-furo[3,2-g]chromen-7-one

Synthesized from ethyl (2-methoxybenzoyl)acetate and 2-methylresorcinol according to SP-1A (0.36 mmol), followed by SP-1B-2 using chloroacetone (d2) (preparative TLC, eluent1—4:6:1; or CC, eluent3—4:1); 23% yield. $^1$H NMR (300 MHz, CDCl$_3$): δ=2.13 (3H, d, Me), 2.63 (3H, s, Me), 3.75 (3H, s, OMe), 6.30 (1H, s, Ar—H), 7.08 (1H, dd, Ar—H), 7.09 (1H, s, Ar—H), 7.12 (1H, td, Ar—H), 7.27 (1H, dd, Ar—H), 7.43 (1H, m, Ar—H), 7.51 (1H, td, Ar—H); [M+H]$^+$ (HPLC/MS): 321.08.

Example 2: 5-(3-methoxyphenyl)-3,9-dimethyl-7H-furo[3,2-g]chromen-7-one

Synthesized from ethyl (3-methoxybenzoyl)acetate and 2-methylresorcinol in 11% yield according to SP-1A (0.36 mmol), followed by SP-1B-2 using chloroacetone (d2) (preparative TLC, eluent1—4:6:1). $^1$H NMR (300 MHz, CDCl$_3$): δ=2.17 (3H, d, Me), 2.64 (3H, s, Me), 3.88 (3H, s, OMe), 6.32 (1H, s, Ar—H), 7.01 (1H, m, Ar—H), 7.05-7.10 (2H, m, Ar—H), 7.40 (1H, s, Ar—H), 7.45 (1H, t, Ar—H), 7.46 (1H, m, Ar—H); [M+H]$^+$ (HPLC/MS): 321.05.

Example 3: 5-(2-chlorophenyl)-3,9-dimethyl-7H-furo[3,2-g]chromen-7-one

Synthesized from ethyl (2-chlorobenzoyl)acetate and 2-methylresorcinol in 25% yield according to SP-1A (0.64 mmol), followed by SP-1B-2 using chloroacetone (d2) (preparative TLC, eluent3—3:1). $^1$H NMR (300 MHz, CDCl$_3$): δ=2.13 (3H, d, Me), 2.64 (3H, s, Me), 6.30 (1H, s, Ar—H), 6.97 (1H, s, Ar—H), 7.35 (1H, dd, Ar—H), 7.44 (1H, td, Ar—H), 7.45 (1H, m, Ar—H), 7.49 (1H, td, Ar—H), 7.58 (1H, dd, Ar—H); [M+H]$^+$ (HPLC/MS): 325.07.

Example 4: 3,9-dimethyl-5-(3-(trifluoromethyl)phenyl)-7H-furo[3,2-g]chromen-7-one Synthesized from ethyl (3-trifluoromethylbenzoyl)acetate and 2-methylresorcinol according to SP-1A (0.81 mmol), followed by SP-1B-1 (using chloroacetone d2) and preparative TLC (eluent1—4:6:1) for the filtrate; 36% yield. $^1$H NMR (300 MHz, CDCl$_3$): δ=2.16 (3H, d, Me), 2.64 (3H, s, Me), 6.33 (1H, s, Ar—H), 7.23 (1H, s, Ar—H), 7.48 (1H, m, Ar—H), 7.67-7.73 (2H, m, Ar—H), 7.76 (1H, s, Ar—H), 7.80-7.85 (1H, m, Ar—H); [M+H]$^+$ (HPLC/MS): 359.03.

Example 5: 5-(2-fluorophenyl)-3,6,9-trimethyl-7H-furo[3,2-g]chromen-7-one

Synthesized from ethyl 3-(2-fluorophenyl)-2-methyl-3-oxopropanoate and 2-methylresorcinol in 23% yield according to SP-1A (4.0 mmol; reaction time was 5.5 h, coumarin c1 was purified by preparative TLC, eluent3 7:3), followed by SP-1B-2 (2.6 eq. chloroacetone d2; preparative TLC, CH$_2$Cl$_2$). $^1$H NMR (300 MHz, CDCl$_3$): δ=2.00 (3H, s, Me), 2.10 (3H, d, Me), 2.63 (3H, s, Me), 6.86 (1H, s, Ar—H), 7.22-7.32 (2H, m, Ar—H), 7.35 (1H, td, Ar—H), 7.42 (1H, m, Ar—H), 7.49-7.58 (1H, m, Ar—H); [M+H]$^+$ (HPLC/MS): 322.89.

Example 6: 5-(3-methoxyphenyl)-3,6,9-trimethyl-7H-furo[3,2-g]chromen-7-one

Synthesized from ethyl 3-(3-methoxyphenyl)-2-methyl-3-oxopropanoate and 2-methylresorcinol in 17% yield according to SP-1A (1.0 mmol), followed by SP-1B-2 (2.6 eq. chloroacetone d2; preparative TLC, eluent1—4:6:1). $^1$H NMR (300 MHz, CDCl$_3$): δ=2.21 (3H, d, Me), 2.42 (3H, s, Me), 2.67 (3H, s, Me), 3.82 (3H, s, OMe), 7.03-7.12 (2H, m, Ar—H), 7.39 (1H, m, Ar—H), 7.33-7.45 (2H, m, Ar—H); [M+H]$^+$ (HPLC/MS): 334.88.

Example 7: 5-(2-methoxyphenyl)-3,6,9-trimethyl-7H-furo[3,2-g]chromen-7-one

Synthesized from ethyl 3-(2-methoxyphenyl)-2-methyl-3-oxopropanoate and 2-methylresorcinol in 29% yield according to SP-1A (2.0 mmol), followed by SP-1B-2 (2.6 eq. chloroacetone d2; intermediate was dissolved in CH$_2$Cl$_2$ and filtered through silica gel, final product was purified by preparative TLC, CH$_2$Cl$_2$). $^1$H NMR (300 MHz, CDCl$_3$): δ=1.94 (3H, s, Me), 2.09 (3H, d, Me), 2.63 (3H, s, Me), 3.74 (3H, s, OMe), 6.86 (1H, s, Ar—H), 7.07-7.16 (3H, m, Ar—H), 7.40 (1H, m, Ar—H), 7.45-7.54 (1H, m, Ar—H); [M+H]$^+$ (HPLC/MS): 334.86.

Example 8: 5-(2-fluorophenyl)-3,9-dimethyl-7H-furo[3,2-g]chromen-7-one

Synthesized from ethyl (2-fluorobenzoyl)acetate and 2-methylresorcinol according to SP-1A (4.0 mmol), followed by SP-1B-1 (using chloroacetone d2) and final purification by column chromatography (eluent2—9:1); 31% yield. $^1$H NMR (300 MHz, d6-DMSO): δ=2.11 (3H, d, Me), 2.55 (3H, s, Me), 6.46 (1H, s, Ar—H), 7.16 (1H, d, Ar—H), 7.41-7.50 (2H, m, Ar—H), 7.56 (1H, td, Ar—H), 7.62-7.70 (1H, m, Ar—H), 7.89 (1H, m, Ar—H); [M+H]$^+$ (HPLC/MS): 309.12.

Example 9: 3,6,9-trimethyl-5-phenyl-7H-furo[3,2-g]chromen-7-one

Synthesized from ethyl 2-methyl-3-oxo-3-phenyl-propanoate and 2-methylresorcinol in 52% yield according to SP-1A (4.0 mmol), followed by SP-1B-1 (2.6 eq. chloroacetone d2; intermediate was dissolved in CH$_2$Cl$_2$ and filtered through silica gel), final purification by further silica gel filtration (CH$_2$Cl$_2$) and re-crystallization from EtOH. $^1$H NMR (300 MHz, CDCl$_3$): δ=1.98 (3H, s, Me), 2.09 (3H, d, Me), 2.64 (3H, s, Me), 6.88 (1H, s, Ar—H), 7.27 (1H, dd, Ar—H), 7.42 (1H, m, Ar—H), 7.47-7.61 (3H, m, Ar—H); [M+H]$^+$ (HPLC/MS): 305.16.

Example 10: 5-(2-ethoxyphenyl)-3,6,9-trimethyl-7H-furo[3,2-g]chromen-7-one

Synthesized from ethyl 3-(2-ethoxyphenyl)-2-methyl-3-oxopropanoate and 2-methylresorcinol in 5% yield according to SP-1A (2.0 mmol), followed by SP-1B-2 (2.6 eq. chloroacetone d2; preparative TLC, CH$_2$Cl$_2$). $^1$H NMR (300 MHz, CDCl$_3$): δ=1.18 (3H, t, OEt), 1.96 (3H, s, Me), 2.09 (3H, d, Me), 2.63 (3H, s, Me), 4.01 (2H, qd, OEt), 6.88 (1H, s, Ar—H), 7.05-7.14 (3H, m, Ar—H), 7.40 (1H, m, Ar—H), 7.42-7.50 (1H, m, Ar—H); [M+H]$^+$ (HPLC/MS): 348.87.

Example 11: 5-(2-chlorophenyl)-3,6,9-trimethyl-7H-furo[3,2-g]chromen-7-one

Synthesized from methyl 3-(2-chlorophenyl)-2-methyl-3-oxopropanoate and 2-methylresorcinol according to SP-1A (0.48 mmol), followed by SP-1B-2 (2.6 eq. chloroacetone d2; preparative TLC, eluent3—9:1); 4% yield. $^1$H NMR (300 MHz, CDCl$_3$): δ=1.96 (3H, s, Me), 2.10 (3H, d, Me), 2.64 (3H, s, Me), 6.73 (1H, s, Ar—H), 7.21-7.26 (1H, m, Ar—H), 7.42 (1H, m, Ar—H), 7.43-7.52 (1H, m, Ar—H), 7.58-7.63 (1H, m, Ar—H); [M+H]$^+$ (HPLC/MS): 339.14.

Example 12: 3,9-dimethyl-2-morpholino-5-phenyl-7H-furo[3,2-g]chromen-7-one (cf. Scheme 2, g)

In a sealed tube in an argon atmosphere, 70 mg of 2-bromo-3,9-dimethyl-5-phenyl-7H-furo[3,2-g]chromen-7-one (f1) (0.19 mmol), tris(dibenzylideneacetone)dipalladium(0) (Pd$_2$dba$_3$, 0.05 eq.), 2-(di-t-butylphosphino)biphenyl (0.2 eq.) and sodium tert-pentoxide (1.4 eq.) were mixed in toluene (2 mL/mmol). After addition of morpholine (1.2 eq.), the mixture was stirred at 110° C. overnight. The mixture was filtrated through cotton wool, the filtrate was concentrated, and the residue was purified twice via preparative TLC (eluent3—2:1; followed by a second chromatography with petroleum ether/ethyl acetate/MeOH—6:3:1) to give the title compound in 13% yield. $^1$H NMR (300 MHz, CDCl$_3$): δ=2.07 (3H, s, Me), 2.59 (3H, s, Me), 3.31 (4H, t, morpholinyl), 3.85 (4H, t, morpholinyl), 6.28 (1H, s, Ar—H), 7.14 (1H, s, Ar—H), 7.46-7.56 (5H, m, Ar—H); [M+H]$^+$ (HPLC/MS): 375.94.

Example 13: 3,9-dimethyl-7-oxo-5-phenyl-7H-furo[3,2-g]chromene-2-carbonitrile (cf. Scheme 2, g)

2-bromo-3,9-dimethyl-5-phenyl-7H-furo[3,2-g]chromen-7-one (f1) (0.3 mmol), CuCN (4.0 eq.), Pd$_2$dba$_3$ (0.2 eq.) and 1,1'-bis(diphenylphosphino)ferrocene (1.6 eq.) were suspended in dioxane (5 mL), and the mixture was stirred at 100° C. for 5 h. The reaction mixture was diluted with ethyl acetate and filtrated over Celite®. The filtrate was washed with 5% aq. NaHCO$_3$, brine and H$_2$O. The organic layer was dried over MgSO$_4$ and concentrated. The residue was purified via preparative TLC (eluent3—2:1) to give the title compound in 10% yield. $^1$H NMR (300 MHz, CDCl$_3$): δ=2.38 (3H, s, Me), 2.65 (3H, s, Me), 6.37 (1H, s, Ar—H), 7.45-7.48 (3H, m, Ar—H), 7.55-7.59 (3H, m, Ar—H); [M+H]$^+$ (HPLC/MS): 315.93.

Example 14: 3,9-dimethyl-2-(morpholinomethyl)-5-phenyl-7H-furo[3,2-g]chromen-7-one (cf. Scheme 2, i)

A mixture of 2-(chloromethyl)-3,9-dimethyl-5-phenyl-7H-furo[3,2-g]chromen-7-one (h1) (0.07 mmol), morpholine (2.0 eq.) and K$_2$CO$_3$ (3.0 eq.) in acetonitrile (14 mL/mmol) was stirred at reflux for 16 h, followed by cooling to rt., filtration, washing with acetonitrile, and concentrating in vacuo. Excess morpholine was removed by coevaporation with toluene. The residue was purified by preparative TLC (eluent2—95:5); yield: 27%. $^1$H NMR (300 MHz, CDCl$_3$): δ=2.29 (3H, s, Me), 2.64 (3H, s, Me), 3.12 (4H, br s, morpholinyl), 4.05 (4H, br s, morpholinyl), 4.25 (2H, br s, CH$_2$), 6.34 (1H, s, Ar—H), 7.40 (1H, s, Ar—H), 7.44-7.50 (2H, m, Ar—H), 7.53-7.58 (3H, m, Ar—H); [M+H]$^+$ (HPLC/MS): 389.94.

Example 15: 2-((dimethylamino)methyl)-3,9-dimethyl-5-phenyl-7H-furo[3,2-g]chromen-7-one (cf. Scheme 2, i)

In a closed vial, 2-(chloromethyl)-3,9-dimethyl-5-phenyl-7H-furo[3,2-g]chromen-7-one (h1) (0.12 mmol) and KI (0.1 eq.) in THF (1.5 mL/mmol) were treated with dimethylamine (2 M in THF, 10 eq.) at 65° C. for 90 min, then partitioned between EtOAc and 2 M aq. NaOH. The organic phase was dried over MgSO$_4$ and concentrated in vacuo. Crude product was purified via preparative TLC (eluent2—95:5); yield: 61%. $^1$H NMR (300 MHz, CDCl$_3$): δ=2.14 (3H, s, Me), 2.32 (6H, s, NMe$_2$), 2.63 (3H, s, Me), 3.59 (2H, s, CH$_2$), 6.29 (1H, s, Ar—H), 7.31 (1H, s, Ar—H), 7.46-7.57 (5H, m, Ar—H); [M+H]$^+$ (HPLC/MS): 347.94.

Example 16: 3-ethyl-6,9-dimethyl-5-phenyl-7H-furo[3,2-g]chromen-7-one

Synthesized from ethyl 2-methyl-3-oxo-3-phenyl-propanoate and 2-methylresorcinol in 21% yield according to SP-1A (4.0 mmol), followed by SP-1B-1 using 1-bromo-2-butanone (2.6 eq.; the product precipitated and was filtered off, taken up in CH$_2$Cl$_2$ and filtered through a pad of silica gel with CH$_2$Cl$_2$ as eluent). $^1$H NMR (300 MHz, CDCl$_3$): δ=1.20 (3H, t, Et), 1.98 (3H, s, Me), 2.52 (2H, qd, Et), 2.63 (3H, s, Me), 6.90 (1H, s, Ar—H), 7.23-7.28 (2H, m, Ar—H), 7.41 (1H, t, Ar—H), 7.47-7.59 (3H, m, Ar—H); [M+H]$^+$ (HPLC/MS): 318.89.

Example 17: 3-methyl-5-(o-tolyl)-7H-furo[3,2-g]chromen-7-one

This compound was synthesized from ethyl 3-oxo-3-o-tolylpropanoate and resorcinol in 10% yield according to SP-1A (0.7 mmol), followed by SP-1B-2 using chloroacetone (d2) (2.6 eq.; preparative TLC, eluent3—3:1; followed by a second chromatography with eluent1—70:60:15). $^1$H NMR (300 MHz, CDCl$_3$): δ=2.12 (3H, d, Me), 2.19 (3H, s, Me), 6.26 (1H, s, Ar—H), 7.11 (1H, s, Ar—H), 7.23 (1H, d, Ar—H), 7.36 (1H, t, Ar—H), 7.38 (1H, d, Ar—H), 7.43 (1H, m, Ar—H), 7.44 (1H, td, Ar—H), 7.49 (1H, s, Ar—H); [M+H]$^+$ (HPLC/MS): 291.13.

Example 18: 3-methyl-5-(m-tolyl)-7H-furo[3,2-g]chromen-7-one

This compound was synthesized from ethyl 3-oxo-3-m-tolylpropanoate and resorcinol in 40% yield according to SP-1A (0.72 mmol), followed by SP-1B-1 using chloroacetone (d2). 1H NMR (300 MHz, CDCl$_3$): δ=2.17 (3H, d, Me), 2.47 (3H, s, Me), 6.31 (1H, s, Ar—H), 7.29 (1H, d, Ar—H), 7.30 (1H, m, Ar—H), 7.36 (1H, d, Ar—H), 7.44 (1H, t, Ar—H), 7.45 (1H, m, Ar—H), 7.49 (1H, s, Ar—H), 7.54 (1H, s, Ar—H); [M+H]$^+$ (HPLC/MS): 291.13.

Example 19: 5-(2-methoxyphenyl)-3-methyl-7H-furo[3,2-g]chromen-7-one

This compound was synthesized from ethyl (2-methoxybenzoyl)acetate and resorcinol in 18% yield according to SP-1A (0.72 mmol), followed by SP-1B-1 using chloroacetone (d2) (2.6 eq.). $^1$H NMR (300 MHz, CDCl$_3$): δ=2.11 (3H, d, Me), 3.73 (3H, s, OMe), 6.28 (1H, s, Ar—H), 7.06 (1H, d, Ar—H), 7.10 (1H, td, Ar—H), 7.22 (1H, s, Ar—H), 7.25 (1H, dd, Ar—H), 7.40 (1H, m, Ar—H), 7.43 (1H, s, Ar—H), 7.49 (1H, td, Ar—H); [M+H]$^+$ (HPLC/MS): 307.07.

Example 20: 5-(3-methoxyphenyl)-3-methyl-7H-furo[3,2-g]chromen-7-one

This compound was synthesized from ethyl (3-methoxybenzoyl)acetate and resorcinol in 29% yield according to SP-1A (0.70 mmol), followed by SP-1B-1 using chloroacetone (d2). 1H NMR (300 MHz, CDCl$_3$): δ=2.18 (3H, d, Me), 3.88 (3H, s, OMe), 6.33 (1H, s, Ar—H), 7.02 (1H, s, Ar—H), 7.05-7.13 (2H, m, Ar—H), 7.45 (1H, m, Ar—H), 7.45-7.52 (2H, m, Ar—H), 7.56 (1H, s, Ar—H); [M+H]$^+$ (HPLC/MS): 307.10.

Example 21: 5-(2-chlorophenyl)-3-methyl-7H-furo[3,2-g]chromen-7-one

Synthesized from ethyl (2-chlorobenzoyl)acetate and resorcinol in 52% yield according to SP-1A (0.66 mmol), followed by SP-1B-2 using chloroacetone (d2) (preparative TLC, eluent1—70:60:15). $^1$H NMR (300 MHz, CDCl$_3$): δ=2.14 (3H, d, Me), 6.31 (1H, s, Ar—H), 7.12 (1H, s, Ar—H), 7.36 (1H, dd, Ar—H), 7.44 (1H, m, Ar—H), 7.45 (1H, td, Ar—H), 7.49 (1H, s, Ar—H), 7.50 (1H, td, Ar—H), 7.59 (1H, dd, Ar—H); [M+H]$^+$ (HPLC/MS): 311.03.

Example 22: 5-(3-chlorophenyl)-3-methyl-7H-furo[3,2-g]chromen-7-one

This compound was synthesized from ethyl (3-chlorobenzoyl)acetate and resorcinol in 43% yield according to SP-1A (0.68 mmol), followed by SP-1B-1 using chloroacetone (d2). 1H NMR (300 MHz, CDCl$_3$): δ=2.19 (3H, d, Me), 6.31 (1H, s, Ar—H), 7.38 (1H, d, Ar—H), 7.42-7.58 (6H, m, Ar—H); [M+H]$^+$ (HPLC/MS): 311.09.

Example 23: 9-methoxy-3-methyl-5-phenyl-7H-furo[3,2-g]chromen-7-one

This compound was synthesized from ethyl benzoylacetate and 2-methoxyresorcinol in 17% yield according to SP-1A (0.57 mmol), followed by SP-1B-2 using chloroacetone (d2) (preparative TLC, eluent1—10:6:1). $^1$H NMR (300 MHz, CDCl$_3$): δ=2.15 (3H, d, Me), 4.32 (3H, s, OMe), 6.32 (1H, s, Ar—H), 7.19 (1H, s, Ar—H), 7.45 (1H, m, Ar—H), 7.47-7.58 (5H, m, Ar—H); [M+H]$^+$ (HPLC/MS): 307.07.

Example 24: 3-methyl-5-phenyl-7H-furo[2,3-b]pyrano[3,2-e]pyridin-7-one (cf. Scheme 6)

The reaction was performed according to SP-3A (1$^{st}$ step) using ethyl benzoylacetate (b4) and pyridine-2,6-diol hydrochloride (r2) (6.78 mmol). In addition, NEt$_3$ (1.2 eq.) was added. As this reaction step directly yielded the cyclized intermediate, the treatment with TFA was omitted (SP-3A, 2$^{nd}$ step). The solvent was decanted from the precipitated product, which was washed with petroleum ether and purified by preparative TLC (eluent2—9:1) to give 7-hydroxy-4-phenyl-2H-pyrano[2,3-b]pyridin-2-one (s). This intermediate was converted into 7-(2-oxopropoxy)-4-phenyl-2H-pyrano[2,3-b]pyridin-2-one according to SP-1B-2 to give the title compound in an overall yield of 2%: 1$^{st}$ step, using 2.6 eq. chloroacetone (d2) (reaction time: 3 h). The filtrate upon removal of the salts was purified by preparative TLC (eluent2—95:5), followed by preparative TLC (CH$_2$Cl$_2$/MeOH/NEt$_3$—96:2:2).

Intermediate 7-(2-oxopropoxy)-4-phenyl-2H-pyrano[2,3-b]pyridin-2-one: $^1$H NMR (300 MHz, CDCl$_3$): δ=2.27 (3H, s, Me), 5.05 (2H, s, CH$_2$), 6.29 (1H, s, Ar—H), 6.81 (1H, d, Ar—H), 7.39-7.43 (2H, m, Ar—H), 7.50-7.55 (3H, m, Ar—H), 7.80 (1H, d, Ar—H).

Title Compound: $^1$H NMR (300 MHz, CDCl$_3$): δ=2.20 (3H, d, Me), 6.40 (1H, s, Ar—H), 7.46-7.50 (2H, m, Ar—H), 7.52 (1H, m, Ar—H), 7.56-7.61 (3H, m, Ar—H), 7.95 (1H, s, Ar—H); [M+H]$^+$ (HPLC/MS): 277.91.

Example 25: 3,6-dimethyl-5-phenyl-7H-furo[2,3-b]pyrano[3,2-e]pyridin-7-one (cf Scheme 6)

This compound was synthesized in analogy to Example 24, using the appropriate β-ketoester ethyl 2-methyl-3-oxo-3-phenyl-propanoate (b4) and pyridine-2,6-diol hydrochloride (r2) in the first reaction step (heating was extended to 12 h). Overall yield: 3%.

Intermediate 3-methyl-7-(2-oxopropoxy)-4-phenyl-2H-pyrano[2,3-b]pyridin-2-one: $^1$H NMR (300 MHz, CDCl$_3$): δ=1.96 (3H, s, Me), 2.25 (3H, s, Me), 5.02 (2H, s, CH$_2$), 6.71 (1H, d, Ar—H), 7.18-7.22 (2H, m, Ar—H), 7.32 (1H, d, Ar—H), 7.45-7.57 (3H, m, Ar—H).

Title compound: $^1$H NMR (300 MHz, CDCl$_3$): δ=2.01 (3H, s, Me), 2.13 (3H, d, Me), 7.26-7.30 (2H, m, Ar—H), 7.46-7.48 (2H, m, Ar—H), 7.52-7.63 (3H, m, Ar—H); [M+H]$^+$ (HPLC/MS): 291.83.

Example 26: 6-bromo-3,9-dimethyl-5-phenylfuro[3,2-g]quinolin-7(8H)-one

Synthesized from ethyl 3-oxo-3-phenylpropanoate and 3-amino-ortho-cresol according to SP-2 (3.0 mmol; SP-2A-

1; workup SP-2B by column chromatography, eluent2—95:5; workup SP-2C, $1^{st}$ step by preparative TLC, eluent1—4:10:1) in 4% overall yield, along with 3,9-dimethyl-5-phenylfuro[3,2-g]quinolin-7(8H)-one in 8% overall yield.

Intermediate 7-hydroxy-8-methyl-4-phenyl-1,2-dihydroquinolin-2-one (11, Scheme 3): $^1$H NMR (300 MHz, CDCl$_3$/CD$_3$OD; calibrated for residual signals of CD$_3$OD): δ=2.32 (3H, s, Me), 6.38 (1H, s, Ar—H), 6.71 (1H, d, Ar—H), 7.21 (1H, d, Ar—H), 7.35-7.40 (2H, m, Ar—H), 7.42-7.49 (3H, m, Ar—H); $^1$H NMR (300 MHz, d$_6$-acetone): δ=2.42 (3H, s, Me), 6.26 (1H, s, Ar—H), 6.79 (1H, d, Ar—H), 7.16 (1H, d, Ar—H), 7.42-7.47 (2H, m, Ar—H), 7.48-7.56 (3H, m, Ar—H).

Intermediate 3,6-dibromo-7-hydroxy-8-methyl-4-phenyl-1,2-dihydroquinolin-2-one (m1, Scheme 3): $^1$H NMR (300 MHz, CDCl$_3$): δ=2.46 (3H, s, Me), 6.08 (1H, br s, OH), 7.09 (1H, s, Ar—H), 7.22-7.26 (2H, m, Ar—H), 7.49-7.59 (3H, m, Ar—H), 9.53 (1H, br s, NH).

By-product 3,9-dimethyl-5-phenylfuro[3,2-g]quinolin-7(8H)-one (n1, $R^2$=H, Scheme 3): 1H NMR (300 MHz, CDCl$_3$/CD$_3$OD 10:1; calibrated for residual signal of CDCl$_3$): δ=2.14 (3H, d, Me), 2.67 (3H, s, Me), 6.62 (1H, s, Ar—H), 7.26 (1H, s, Ar—H), 7.44-7.54 (6H, m, Ar—H).

Title compound (n1, $R^2$=Br, Scheme 3): $^1$H NMR (300 MHz, CDCl$_3$): δ=2.09 (3H, d, Me), 2.62 (3H, s, Me), 7.05 (1H, s, Ar—H), 7.28-7.33 (2H, m, Ar—H), 7.41 (1H, m, Ar—H), 7.51-7.62 (3H, m, Ar—H), 9.10 (1H, br s, NH); [M+H]$^+$ (HPLC/MS): 367.92.

Alternatively, the title compound was synthesized from ethyl 3-oxo-3-phenylpropanoate and 3-amino-ortho-cresol according to SP-3 (16.0 mmol; workup SP-3A, $2^{nd}$ step by washing the resulting crude solid with CH$_2$Cl$_2$; SP-3B performed to yield double-bromination; workup SP-3C, $2^{nd}$ step by preparative TLC, petroleum ether/CH$_2$Cl2/ethyl acetate—2:5:3) in 2% overall yield (cf. Scheme 4).

Example 27: 6-bromo-5-(2-fluorophenyl)-3,9-dimethylfuro[3,2-g]quinolin-7(8H)-one The title compound was synthesized from ethyl (2-fluorobenzoyl)acetate and 3-amino-ortho-cresol according to SP-2 (2.0 mmol; SP-2A-2; workup SP-2B by preparative TLC, eluent1—4:6:1; workup SP-2C, $1^{st}$ step by preparative TLC, eluent3—1:1) in 0.5% overall yield along with 5-(2-fluorophenyl)-3,9-dimethylfuro[3,2-g]quinolin-7(8H)-one in 1% overall yield.

Intermediate 4-(2-fluorophenyl)-7-hydroxy-8-methyl-1,2-dihydroquinolin-2-one (11, Scheme 3): $^1$H NMR (300 MHz, CD$_3$OD): δ=2.34 (3H, s, Me), 6.34 (1H, s, Ar—H), 6.73 (1H, d, Ar—H), 6.97 (1H, dd, Ar—H), 7.22-7.40 (3H, m, Ar—H), 7.49-7.56 (1H, m, Ar—H).

Intermediate 3,6-dibromo-4-(2-fluorophenyl)-7-hydroxy-8-methyl-1,2-dihydroquinolin-2-one (m1, Scheme 3): $^1$H NMR (300 MHz, CDCl$_3$): δ=2.43 (3H, s, Me), 7.07 (1H, s, Ar—H), 7.19-7.40 (4H, m, Ar—H and OH), 7.50-7.58 (1H, m, Ar—H), 9.19 (1H, br s, NH).

Intermediate 3,6-dibromo-4-(2-fluorophenyl)-8-methyl-7-(2-oxopropoxy)-1,2-dihydroquinolin-2-one: $^1$H NMR (300 MHz, CDCl$_3$): δ=2.38 (3H, s, Me), 2.56 (3H, s, Me), 4.51 (2H, s, CH$_2$), 7.17 (1H, s, Ar—H), 7.20-7.39 (3H, m, Ar—H), 7.52-7.60 (1H, m, Ar—H), 10.16 (1H, br s, NH).

By-product 5-(2-fluorophenyl)-3,9-dimethylfuro[3,2-g]quinolin-7(8H)-one (n1, $R^2$=H, Scheme 3): Result of LC/MS [M+H]$^+$: 307.92

Title Compound (n1, $R^2$=Br, Scheme 3): $^1$H NMR (300 MHz, CDCl$_3$): δ=2.11 (3H, d, Me), 2.61 (3H, s, Me), 7.03 (1H, s, Ar—H), 7.27-7.33 (2H, m, Ar—H), 7.37 (1H, td, Ar—H), 7.43 (1H, m, Ar—H), 7.55 (1H, m, Ar—H), 8.98 (1H, br s, NH); [M+H]$^+$ (HPLC/MS): 385.72.

Example 28: 6-bromo-3,9-dimethyl-5-(o-tolyl)furo[3,2-g]quinolin-7(8H)-one

Example 29: 3,9-dimethyl-5-(o-tolyl)furo[3,2-g]quinolin-7(8H)-one

The title compounds (Examples 28 and 29) were synthesized from ethyl 3-oxo-3-o-tolylpropanoate and 3-amino-ortho-cresol according to SP-2 (2.0 mmol; SP-2A-2; workup SP-2B by preparative TLC, eluent1—4:6:1; workup SP-2C, $1^{st}$ step by preparative TLC, eluent3—1:1) in 1% overall yield for 6-bromo-3,9-dimethyl-5-(o-tolyl)furo[3,2-g]quinolin-7(8H)-one along with 3,9-dimethyl-5-(o-tolyl)furo[3,2-g]quinolin-7(8H)-one in 0.5% overall yield.

Intermediate 7-hydroxy-8-methyl-4-(2-methylphenyl)-1,2-dihydroquinolin-2-one (11, Scheme 3): $^1$H NMR (300 MHz, CD$_3$OD): δ=2.08 (3H, s, Me), 2.34 (3H, s, Me), 6.23 (1H, s, Ar—H), 6.68 (1H, d, Ar—H), 6.79 (1H, d, Ar—H), 7.15 (1H, d, Ar—H), 7.26-7.40 (3H, m, Ar—H).

Intermediate 3,6-dibromo-7-hydroxy-8-methyl-4-(2-methylphenyl)-1,2-dihydroquinolin-2-one (m1, Scheme 3): $^1$H NMR (300 MHz, CDCl$_3$): δ=2.07 (3H, s, Me), 2.44 (3H, s, Me), 6.96 (1H, s, Ar—H), 7.06 (1H, d, Ar—H), 7.31-7.46 (4H, m, Ar—H and OH), 9.24 (1H, br s, NH).

Intermediate 3,6-dibromo-8-methyl-4-(2-methylphenyl)-7-(2-oxopropoxy)-1,2-dihydroquinolin-2-one: $^1$H NMR (300 MHz, CDCl$_3$): δ=2.07 (3H, s, Me), 2.38 (3H, s, Me), 2.56 (3H, s, Me), 4.50 (2H, s, CH$_2$), 7.05 (1H, s, Ar—H), 7.06 (1H, d, Ar—H), 7.33-7.47 (3H, m, Ar—H), 10.07 (1H, br s, NH).

Title Compound, Example 28: $^1$H NMR (300 MHz, CDCl$_3$): δ=2.08 (3H, d, Me), 2.09 (3H, s, Me), 2.62 (3H, s, Me), 6.93 (1H, s, Ar—H), 7.12 (1H, d, Ar—H), 7.35-7.48 (4H, m, Ar—H), 9.08 (1H, br s, NH); [M+H]$^+$ (HPLC/MS): 381.75.

Title Compound, Example 29: 1H NMR (300 MHz, CDCl$_3$): δ=2.11 (3H, d, Me), 2.14 (3H, s, Me), 2.61 (3H, s, Me), 6.49 (1H, s, Ar—H), 7.05 (1H, s, Ar—H), 7.26-7.45 (5H, m, Ar—H), 8.99 (1H, br s, NH); [M+H]$^+$ (HPLC/MS): 303.92.

Example 30: 5-(2-fluorophenyl)-3,6,9-trimethylfuro[3,2-g]quinolin-7(8H)-one

The title compound was synthesized from ethyl 3-(2-fluorophenyl)-2-methyl-3-oxopropanoate and 3-amino-o-cresol (8.0 mmol) according to SP-3A (column chromatography, eluent2—95:5), SP-3B and SP-2C (purification by preparative TLC, eluent2—95:5, followed by preparative TLC, eluent2—95:5 followed by preparative HPLC) in an overall yield of 4%. $^1$H NMR (300 MHz, d6-DMSO): δ=1.86 (3H, s, Me), 2.02 (3H, d, Me), 2.60 (3H, s, Me), 6.84 (1H, s, Ar—H), 7.37 (1H, td, Ar—H), 7.41-7.49 (2H, m, Ar—H), 7.62 (1H, m, Ar—H), 7.75 (1H, m, Ar—H), 11.13 (1H, br s, NH); [M+H]$^+$ (HPLC/MS): 322.05.

Example 31: 3,6,9-trimethyl-5-phenylfuro[3,2-g]quinolin-7(8H)-one

The title compound was synthesized from 3-amino-o-cresol (6.5 mmol) and ethyl 2-methyl-3-oxo-3-phenyl-propanoate according to SP-3 (SP-3A: column chromatography, eluent2—95:5; SP-3C, $2^{nd}$ step: preparative TLC, eluent2—95:5) in an overall yield of 10%.

Intermediate 7-hydroxy-3,8-dimethyl-4-phenyl-1,2-dihydroquinolin-2-one (12, Scheme 4): $^1$H NMR (300 MHz, d6-DMSO): δ=1.78 (3H, s, Me), 2.25 (3H, s, Me), 6.56 (1H, d, Ar—H), 6.62 (1H, d, Ar—H), 7.19-7.23 (2H, m, Ar—H), 7.43-7.56 (3H, m, Ar—H), 9.82 (1H, br s, NH or OH), 10.68 (1H, br s, OH or NH).

Title Compound: $^1$H NMR (300 MHz, d6-DMSO): δ=1.83 (3H, s, Me), 2.00 (3H, d, Me), 2.59 (3H, s, Me), 6.84 (1H, s, Ar—H), 7.29 (2H, m, Ar—H), 7.49-7.62 (3H, m, Ar—H), 7.73 (1H, m, Ar—H), 11.03 (1H, br s, NH); [M+H]$^+$ (HPLC/MS): 304.18.

Alternatively, 6-bromo-7-hydroxy-3,8-dimethyl-4-phenyl-1,2-dihydroquinolin-2-one resulting from step SP-3B can be converted into the title compound according to SP-2C (product was repeatedly crystallized from MeOH, mother liquor was purified by preparative TLC, eluent3—9:1) in an overall yield of 6% based on 3-amino-o-cresol (cf. Scheme 4).

Example 32: 3,8,9-trimethyl-5-phenylfuro[3,2-g]quinolin-7(8H)-one

The title compound was synthesized from 3,9-dimethyl-5-phenylfuro[3,2-g]quinolin-7(8H)-one (by-product of the synthesis of Example 26; 0.1 mmol) according to SP-4 in 11% yield along with 45% by-product 7-methoxy-3,9-dimethyl-5-phenylfuro[3,2-g]quinoline.

Title Compound (n2, R$^2$=H, Scheme 3): $^1$H NMR (300 MHz, CDCl$_3$): δ=2.13 (3H, d, Me), 2.85 (3H, s, Me), 3.92 (3H, s, NMe), 6.57 (1H, s, Ar—H), 7.42-7.53 (7H, m, Ar—H); [M+H]$^+$ (HPLC/MS): 304.16.

Lactim ether by-product 7-methoxy-3,9-dimethyl-5-phenylfuro[3,2-g]quinoline (o, R$^2$=H, Scheme 3): $^1$H NMR (300 MHz, CDCl$_3$): δ=2.20 (3H, d, Me), 2.90 (3H, s, Me), 4.15 (3H, s, OMe), 6.81 (1H, s, Ar—H), 7.46-7.55 (6H, m, Ar—H), 7.66 (1H, m, Ar—H).

Example 33: 6-bromo-3,8,9-trimethyl-5-phenylfuro[3,2-g]quinolin-7(8H)-one

The title compound was synthesized from Example 26 (0.1 mmol) according to SP-4 in 3% yield with 33% by-product 6-bromo-7-methoxy-3,9-dimethyl-5-phenylfuro[3,2-g]quinoline.

Title Compound (n2, R$^2$=Br, Scheme 3): $^1$H NMR (300 MHz, CDCl$_3$): δ=2.08 (3H, d, Me), 2.84 (3H, s, Me), 4.00 (3H, s, NMe), 7.05 (1H, s, Ar—H), 7.26-7.31 (2H, m, Ar—H), 7.41 (1H, m, Ar—H), 7.51-7.60 (3H, m, Ar—H); [M+H]$^+$ (HPLC/MS): 381.80.

Lactim ether by-product 6-bromo-7-methoxy-3,9-dimethyl-5-phenylfuro[3,2-g]quinoline (o, R$^2$=Br, Scheme 3): $^1$H NMR (300 MHz, CDCl$_3$): δ=2.13 (3H, d, Me), 2.89 (3H, s, Me), 4.23 (3H, s, OMe), 7.20 (1H, s, Ar—H), 7.29-7.34 (2H, m, Ar—H), 7.47 (1H, m, Ar—H), 7.50-7.60 (3H, m, Ar—H).

Example 34: 3,6,8,9-tetramethyl-5-phenylfuro[3,2-g]quinolin-7(8H)-one

Synthesis of 2-methyl-3-(methylamino)phenol according to US2004/0127747, example 3 (cf. Scheme 4, conversion of k1 into k2): 3-amino-o-cresol (4.1 mmol, 1.0 eq.) and sodium Y Zeolite (125 mg/mmol; from Sigma Aldrich, order no. 334448) were suspended in dimethyl carbonate (5 mL/mmol). The resulting mixture was stirred at 90° C. for 48 h. The reaction mixture was cooled to room temperature, filtered and concentrated in vacuo. Crude product was used for further transformation without purification.

The title compound was synthesized from 2-methyl-3-(methylamino)phenol (6.5 mmol) and ethyl 2-methyl-3-oxo-3-phenyl-propanoate according to SP-3 (SP-3A: column chromatography, eluent2—95:5; SP-3C, 1$^{st}$ step: reaction time 1 h, preparative TLC, eluent3—1:1; SP-3C, 2$^{nd}$ step: purification by preparative TLC, eluent3—1:1), overall yield 4%.

Intermediate 6-bromo-1,3,8-trimethyl-4-phenyl-7-(prop-2-en-1-yloxy)-1,2-dihydroquinolin-2-one: $^1$H NMR (300 MHz, CDCl$_3$): δ=1.96 (3H, s, Me), 2.59 (3H, s, Me), 3.79 (3H, s, NMe), 4.50 (2H, dt, CH$_2$), 5.30 (1H, dq, alkenyl-CH$_2$), 5.45 (1H, dq, alkenyl-CH$_2$), 6.16 (1H, ddt, alkenyl-CH), 7.09 (1H, s, Ar—H), 7.14-7.19 (2H, m, Ar—H), 7.42-7.54 (3H, m, Ar—H).

Title Compound: $^1$H NMR (300 MHz, CDCl$_3$): δ=1.98 (3H, s, Me), 2.07 (3H, d, Me), 2.83 (3H, s, Me), 3.95 (3H, s, NMe), 6.98 (1H, s, Ar—H), 7.21-7.25 (2H, m, Ar—H), 7.38 (1H, m, Ar—H), 7.44-7.55 (3H, m, Ar—H); [M+H]$^+$ (HPLC/MS): 318.10.

Example 35: 3,6,9-trimethyl-5-phenyl-7H-chromeno[6,7-d]isoxazol-7-one

Starting material 7-hydroxy-3,8-dimethyl-4-phenyl-2H-chromen-2-one was synthesized as described above (intermediate in the synthesis of Example 9), 79% yield following SP-1A (4.0 to 8.0 mmol; crude product was filtered through silica gel pad, CH$_2$Cl$_2$ to eluent2—95:5).

7-hydroxy-3,8-dimethyl-4-phenyl-2H-chromen-2-one (1.88 mmol) was brominated according to SP-3B to give 6-bromo-7-hydroxy-3,8-dimethyl-4-phenyl-2H-chromen-2-one in 64% yield (upon purification by preparative TLC, eluent CH$_2$Cl$_2$). $^1$H NMR (300 MHz, CDCl$_3$): δ=1.95 (3H, s, Me), 2.43 (3H, s, Me), 5.87 (1H, br s, OH), 6.94 (1H, s, Ar—H), 7.17-7.22 (2H, m, Ar—H), 7.46-7.57 (3H, m, Ar—H).

The title compound was synthesized from 6-bromo-7-hydroxy-3,8-dimethyl-4-phenyl-2H-chromen-2-one (1.0 mmol) according to SP-5A and SP-5C (purification each by preparative TLC, eluent CH$_2$Cl$_2$) in an overall yield of 16% (cf. Scheme 5). $^1$H NMR (300 MHz, CDCl$_3$): δ=1.99 (3H, s, Me), 2.44 (3H, s, Me), 2.67 (3H, s, Me), 7.01 (1H, s, Ar—H), 7.24-7.28 (2H, m, Ar—H), 7.50-7.61 (3H, m, Ar—H); [M+H]$^+$ (HPLC/MS): 306.09.

Example 36: 3,6,9-trimethyl-5-phenylisoxazolo[4,5-g]quinolin-7(8H)-one

The synthesis of 6-bromo-7-hydroxy-3,8-dimethyl-4-phenylquinolin-2(1H)-one is described as an intermediate in the synthesis of Example 31, resulting from reaction SP-3A (20-70 mmol) and SP-3B (0.4-14 mmol) in 33% yield.

The title compound was synthesized from 6-bromo-7-hydroxy-3,8-dimethyl-4-phenylquinolin-2(1H)-one (0.9 mmol) according to SP-5A and SP-5C (purification each by preparative TLC, eluent2—95:5) in an overall yield of 8%. $^1$H NMR (300 MHz, d6-DMSO): δ=1.84 (3H, s, Me), 2.37 (3H, s, Me), 2.61 (3H, s, Me), 7.06 (1H, s, Ar—H), 7.28-7.33 (2H, m, Ar—H), 7.51-7.64 (3H, m, Ar—H), 11.24 (1H, br s, NH); [M+H]$^+$ (HPLC/MS): 305.05.

Example 37: 6,9-dimethyl-4-phenyl-2H-thieno[3,2-g]chromen-2-one (cf. Scheme 7)

The synthesis of the starting material 7-hydroxy-8-methyl-4-phenyl-2H-chromen-2-one is described above as an intermediate in the synthesis of compound e1 in Scheme 2, 3,9-dimethyl-5-phenyl-7H-furo[3,2-g]chromen-7-one, which was obtained in 75% yield from ethyl benzoylacetate and 2-methylresorcinol following SP-1A (50 mmol).

7-hydroxy-8-methyl-4-phenyl-2H-chromen-2-one (c2) (2.0 mmol) was dissolved in dioxane (5 mL/mmol), 4-dimethylaminopyridine (0.1 eq.), dimethylthiocarbamoyl chloride (1.2 eq.) and triethylamine (2.0 eq.) were added, and the mixture was stirred at 100° C. overnight. The reaction mixture was cooled to room temperature and filtered. The filter cake was washed with dioxane and the filtrate was concentrated in vacuo. $^1$H NMR (300 MHz, CDCl$_3$): δ=2.34 (3H, s, Me), 3.40 and 3.48 (each 3H, s, NMe$_2$), 6.35 (1H, s, Ar—H), 6.93 (1H, d, Ar—H), 7.34 (1H, d, Ar—H), 7.45-7.47 (2H, m, Ar—H), 7.50-7.53 (3H, m, Ar—H).

The resulting O-(8-methyl-2-oxo-4-phenyl-2H-chromen-7-yl) dimethylcarbamothioate (v) was dissolved in diphenyl ether (5 mL/mmol) and stirred at 250° C. under microwave irradiation for 2 h. The reaction mixture was directly loaded onto a flash chromatography column (petroleum ether to eluent3, 2:1) to give S-(8-methyl-2-oxo-4-phenyl-2H-chromen-7-yl) dimethylcarbamothioate in 83% yield over two steps. $^1$H NMR (300 MHz, CDCl$_3$): δ=2.60 (3H, s, Me), 3.09 (6H, br s, NMe$_2$), 6.39 (1H, s, Ar—H), 7.30 (1H, d, Ar—H), 7.38 (1H, d, Ar—H), 7.41-7.45 (2H, m, Ar—H), 7.49-7.53 (3H, m, Ar—H).

S-(8-methyl-2-oxo-4-phenyl-2H-chromen-7-yl) dimethylcarbamothioate was dissolved in MeOH (20 mL/mmol). 2 M aq. NaOH (6 eq.) was added, and the mixture was stirred under reflux overnight, followed by partitioning between water and CH$_2$Cl$_2$. The aqueous phase was then acidified with HCl. Extraction with Et$_2$O, drying of the organic phase over MgSO$_4$ and removal of solvent gave crude 7-mercapto-8-methyl-4-phenyl-2H-chromen-2-one (w).

7-mercapto-8-methyl-4-phenyl-2H-chromen-2-one (w) was converted into the title compound with chloroacetone (d2) (2.6 eq.) according to SP-1B-1. The product precipitated, was filtered off, taken up in CH$_2$Cl$_2$ and filtered through a silica gel pad, eluent CH$_2$Cl$_2$. Yield over 3 steps (referring to S-(8-methyl-2-oxo-4-phenyl-2H-chromen-7-yl) dimethylcarbamothioate): 8%.

$^1$H NMR (300 MHz, CDCl$_3$): δ=2.32 (3H, d, Me), 2.70 (3H, s, Me), 6.37 (1H, s, Ar—H), 7.06 (1H, m, Ar—H), 7.52-7.58 (5H, m, Ar—H), 7.60 (1H, s, Ar—H); [M+H]$^+$ (HPLC/MS): 306.85.

Example 38: 2,4-dimethyl-8-phenyl-6H-chromeno[6,7-d]oxazol-6-one (cf. Scheme 7)

The synthesis of the starting material 7-hydroxy-8-methyl-4-phenyl-2H-chromen-2-one is described above as an intermediate in the synthesis compound e1 in Scheme 2, 3,9-dimethyl-5-phenyl-7H-furo[3,2-g]chromen-7-one, which was obtained in 75% yield from ethyl benzoylacetate and 2-methylresorcinol following SP-1A (50 mmol). 7-hydroxy-8-methyl-4-phenyl-2H-chromen-2-one (c2) (4.8 mmol; 1.0 eq.) was dissolved in concentrated sulfuric acid (1.9 mL/mmol). Upon cooling to −20° C., a 1:3 (v/v) mixture of concentrated nitric acid and concentrated sulfuric acid (0.3 mL/mmol) was added slowly over a period of 30 min. Stirring was continued at −20° C. for 10 min. The mixture was poured onto ice. The resulting suspension (upon thawing of the ice) was extracted with CH$_2$Cl$_2$, combined organic layers were dried over MgSO$_4$, and the crude product was purified by preparative TLC (eluent3—2:1) to give 7-hydroxy-8-methyl-6-nitro-4-phenyl-2H-chromen-2-one in 33% yield. $^1$H NMR (300 MHz, CDCl$_3$): δ=2.45 (3H, s, Me), 6.34 (1H, s, Ar—H), 7.41-7.45 (2H, m, Ar—H), 7.56-7.59 (3H, m, Ar—H), 8.18 (1H, s, Ar—H), 11.20 (1H, s, OH).

Reduction of the nitro group was achieved in an autoclave: 7-hydroxy-8-methyl-6-nitro-4-phenyl-2H-chromen-2-one (1.5 mmol, 1.0 eq.) was dissolved in MeOH (7.5 mL/mmol). Pd/C (10% on carbon; 0.05 eq. Pd) was added and the mixture was stirred under an atmosphere of hydrogen (4 bar) at room temperature for 90 min. The suspension was filtrated through a PTFE-syringe filter (pore size: 0.45 μm), and the filtrate was concentrated and dried in high vacuum to give crude 6-amino-7-hydroxy-8-methyl-4-phenyl-2H-chromen-2-one (y) in 88% yield. $^1$H NMR (300 MHz, CDCl$_3$): δ=2.29 (3H, s, Me), 4.42 (3H, br s, OH/NH$_2$), 6.09 (1H, s, Ar—H), 6.60 (1H, s, Ar—H), 7.31-7.36 (2H, m, Ar—H), 7.39-7.43 (3H, m, Ar—H).

Crude 6-amino-7-hydroxy-8-methyl-4-phenyl-2H-chromen-2-one (y) (1.2 mmol, 1.0 eq.) was dissolved in DMF (2.5 mL/mmol), and pyridinium p-toluenesulfonate (0.15 eq.) and 1,1,1-trimethoxyethane (1.7 eq.) were added. The mixture was stirred at 60° C. for 90 min. Volatiles were removed under reduced pressure and the residue was dried in high vacuum. The title compound 2,4-dimethyl-8-phenyl-6H-chromeno[6,7-d]oxazol-6-one (z) was obtained in 15% upon purified via preparative TLC (eluent3—4:1). $^1$H NMR (300 MHz, CDCl$_3$): δ=2.64 (3H, s, Me), 2.66 (3H, s, Me), 6.36 (1H, s, Ar—H), 7.44-7.47 (2H, m, Ar—H), 7.51-7.54 (3H, m, Ar—H), 7.57 (1H, s, Ar—H); [M+H]$^+$ (HPLC/MS): 291.83.

Example 39: 4-methyl-2-((methylamino)methyl)-8-phenyl-6H-chromeno[6,7-d]oxazol-6-one Crude 6-amino-7-hydroxy-8-methyl-4-phenyl-2H-chromen-2-one was synthesized as described in Example 38. Cyclization to give 2-(bromomethyl)-4-methyl-8-phenyl-6H-chromeno[6,7-d]oxazol-6-one was performed in analogy to *Tetrahedron* 2010, 66, 8189: To a mixture of 6-amino-7-hydroxy-8-methyl-4-phenyl-2H-chromen-2-one (1.0 mmol, 1.0 eq.) in polyphosphoric acid (40 eq.) was added bromoacetic acid (1.15 eq.). The mixture was stirred at 130° C. overnight. Upon addition of water (40 ml), the slurry was stirred at 60° C. for 30 min and cooled to room temperature again. The mixture was extracted with CH$_2$Cl$_2$, combined organic layers were washed with water and dried over MgSO$_4$, filtered and concentrated in vacuo to give crude 2-(bromomethyl)-4-methyl-8-phenyl-6H-chromeno[6,7-d]oxazol-6-one in 50% yield. $^1$H NMR (300 MHz, CDCl$_3$): δ=2.67 (3H, s, Me), 4.58 (2H, s, CH$_2$), 6.39 (1H, s, Ar—H), 7.43-7.47 (2H, m, Ar—H), 7.50-7.55 (3H, m, Ar—H), 7.66 (1H, s, Ar—H). 2-(bromomethyl)-4-methyl-8-phenyl-6H-chromeno[6,7-d]oxazol-6-one (0.3 mmol, 1.0 eq.) and potassium iodide (0.1 eq.) were suspended in THF (2 mL/mmol). Upon addition of methylamine (2 M in THF; 1.2 eq.), the mixture was stirred at 65° C. for 90 min. Upon cooling, the mixture was partitioned between EtOAc and 2 N aq. NaOH. Combined organic phases were washed with water, dried over MgSO$_4$ and concentrated in vacuo. The crude product was purified by repeated preparative TLC (first, eluent2—95:5; second, eluent3—1:2) to give the title compound in 4% yield. $^1$H NMR (300 MHz, CDCl$_3$): δ=2.65 (3H, s, NMe), 2.67 (3H, s, Me), 4.20 (2H, s, CH$_2$), 6.38 (1H, s, Ar—H), 7.43-7.47 (2H, m, Ar—H), 7.51-7.54 (3H, m, Ar—H), 7.64 (1H, s, Ar—H); [M+H]$^+$ (HPLC/MS): 321.17.

Example 40: 5-(2-chlorophenyl)-3,6,9-trimethylfuro[3,2-g]quinolin-7(8H)-one

The title compound was synthesized from methyl 3-(2-chlorophenyl)-2-methyl-3-oxopropanoate and 3-amino-o-cresol (8.1 mmol) according to SP-3A (column chromatography, eluent2—95:5), SP-3B and SP-2C (purification by preparative TLC, 1$^{st}$ step: eluent2—95:5; 2$^{nd}$ step: eluent2—95:5 followed by prep. HPLC) in an overall yield of 4%. $^1$H NMR (300 MHz, d6-DMSO): δ=1.80 (3H, s, Me), 2.01 (3H, d, Me), 2.60 (3H, s, Me), 6.70 (1H, s, Ar—H), 7.37 (1H, m, Ar—H), 7.57 (2H, m, Ar—H), 7.69-7.73 (1H, m, Ar—H), 7.74 (1H, m, Ar—H), 11.12 (1H, br s, NH); [M+H]$^+$ (HPLC/MS): 338.02.

Example 41: 3-cyclopropyl-9-methyl-5-phenyl-7H-furo[3,2-g]chromen-7-one

The synthesis of the starting material 7-hydroxy-8-methyl-4-phenyl-2H-chromen-2-one is described above as an intermediate in the synthesis of compound e1 in Scheme 2, which was obtained in 75% yield from ethyl benzoylacetate and 2-methylresorcinol following SP-1A (50 mmol).

Starting with 7-hydroxy-8-methyl-4-phenyl-2H-chromen-2-one (0.4 mmol), the title compound was synthesized in 34% yield following SP-1B-2 using 2.6 eq. 2-bromo-1-cyclopropylethanone (reaction time: 3 h) (upon extraction the final product was crystallized from methanol). $^1$H NMR (300 MHz, CDCl$_3$): δ=0.60 (2H, m, CH$_2$), 0.87 (2H, m, CH$_2$), 1.71 (1H, me, CH), 2.61 (3H, s, Me), 6.31 (1H, s, Ar—H), 7.35 (1H, s, Ar—H), 7.48-7.57 (6H, m, Ar—H); [M+H]$^+$ (HPLC/MS): 317.05.

Example 42: 3-cyclopropyl-6,9-dimethyl-5-phenyl-7H-furo[3,2-g]chromen-7-one

This compound was synthesized from ethyl 2-methyl-3-oxo-3-phenyl-propanoate and 2-methylresorcinol in 12% yield according to SP-1A (4.2 mmol; crude product was filtered through a pad of silica gel, CH$_2$Cl$_2$ to eluent2—95:5), followed by SP-1B-2 using 2-bromo-1-cyclopropylethanone (2.6 eq.; reaction time step 1=75 min; reaction time step 2=45 min) (preparative TLC, eluent1—7:3:0.1). $^1$H NMR (300 MHz, CDCl$_3$): δ=0.54 (2H, m, CH$_2$), 0.81 (2H, m, CH$_2$), 1.63 (1H, me, CH), 1.99 (3H, s, Me), 2.61 (3H, s, Me), 7.01 (1H, s, Ar—H), 7.26-7.31 (3H, m, Ar—H), 7.48-7.60 (3H, m, Ar—H); [M+H]$^+$ (HPLC/MS): 331.03.

Example 43: 3,6,9-trimethyl-4-phenyl-2H-thieno[3,2-g]chromen-2-one

Starting material 7-hydroxy-3,8-dimethyl-4-phenyl-2H-chromen-2-one was synthesized as described above (intermediate in synthesis of Example 9) with a yield of 79% following SP-1A (4.0 to 8.0 mmol; crude product was filtered through a silica gel pad, CH$_2$Cl$_2$ to eluent2—95:5). $^1$H NMR (300 MHz, CDCl$_3$): δ=1.95 (3H, s, Me), 2.37 (3H, s, Me), 6.67 (1H, d, Ar—H), 6.73 (1H, d, Ar—H), 7.18-7.23 (2H, m, Ar—H), 7.42-7.55 (3H, m, Ar—H).

Further transformations to give the title compound in analogy to Example 37, starting with 4.0 mmol 7-hydroxy-3,8-dimethyl-4-phenyl-2H-chromen-2-one (c2, cf. Scheme 7):

step 1: additional preparative TLC (eluent2—95:5), O-(3,8-dimethyl-2-oxo-4-phenyl-2H-chromen-7-yl) dimethylcarbamothioate (v) in 63% yield; $^1$H NMR (300 MHz, CDCl$_3$): δ=2.02 (3H, s, Me), 2.37 (3H, s, Me), 3.43 and 3.49 (each 3H, s, NMe$_2$), 6.87 (1H, d, Ar—H), 6.91 (1H, d, Ar—H), 7.24-7.29 (2H, m, Ar—H), 7.47-7.58 (3H, m, Ar—H).

step 2: S-(3,8-dimethyl-2-oxo-4-phenyl-2H-chromen-7-yl) dimethylcarbamothioate in 85% yield; $^1$H NMR (300 MHz, CDCl$_3$): δ=2.00 (3H, s, Me), 2.59 (3H, s, Me), 3.08 (6H, br s, NMe$_2$), 6.83 (1H, d, Ar—H), 7.19-7.29 (3H, m, Ar—H), 7.47-7.55 (3H, m, Ar—H).

step 3: additional preparative TLC (eluent2—98:2), 7-mercapto-3,8-dimethyl-4-phenyl-2H-chromen-2-one (w) in 42% yield.

step 4: Conversion of 7-mercapto-3,8-dimethyl-4-phenyl-2H-chromen-2-one into the title compound was achieved using chloroacetone (d2) (2.6 eq.) according to SP-1B-1. Product precipitated, was filtered off, purified by preparative TLC (eluent1—4:6:0.1). Yield: 10%.

Intermediate 3,8-dimethyl-7-[(2-oxopropyl)sulfanyl]-4-phenyl-2H-chromen-2-one: $^1$H NMR (300 MHz, CDCl$_3$): δ=1.95 (3H, s, Me), 2.25 (3H, s, Me), 2.51 (3H, s, Me), 3.69 (2H, s, CH$_2$), 6.76 (1H, d, Ar—H), 6.96 (1H, d, Ar—H), 7.16-7.20 (2H, m, Ar—H), 7.42-7.53 (3H, m, Ar—H).

Title Compound: $^1$H NMR (300 MHz, CDCl$_3$): δ=2.01 (3H, s, Me), 2.23 (3H, d, Me), 2.68 (3H, s, Me), 7.01 (1H, m, Ar—H), 7.11 (1H, s, Ar—H), 7.26-7.30 (2H, m, Ar—H), 7.49-7.60 (3H, m, Ar—H); [M+H]$^+$ (HPLC/MS): 321.06.

Example 44: 3,9-dimethyl-5-(pyridin-3-yl)-7H-furo[3,2-g]chromen-7-one

This compound was synthesized from methyl 3-oxo-3-(pyridin-3-yl)propanoate and 2-methylresorcinol in 16% yield according to SP-1A (0.64 mmol), followed by SP-1B-2 using chloroacetone (d2) (preparative TLC, eluent1—10:6:1). $^1$H NMR (300 MHz, CDCl$_3$): δ=2.15 (3H, d, Me), 2.61 (3H, s, Me), 6.30 (1H, s, Ar—H), 7.24 (1H, s, Ar—H), 7.46 (1H, m, Ar—H), 7.52 (1H, ddd, Ar—H), 7.83 (1H, dt, Ar—H), 8.76 (1H, d, Ar—H), 8.80 (1H, dd, Ar—H); [M+H]$^+$ (HPLC/MS): 292.04.

Example 45: 3,9-dimethyl-7-oxo-5-phenyl-7H-furo[3,2-g]chromene-2-carbonitrile 3,6,9-trimethyl-5-phenyl-7H-furo[3,2-g]chromen-7-one (Example 9, 8.0 mmol) was 2-brominated according to the bromination protocol described for Scheme 2 (conversion of e2 into f2), yielding 98% of 2-bromo-3,6,9-trimethyl-5-phenyl-7H-furo[3,2-g]chromen-7-one after purification by preparative TLC (eluent2—99:1). The latter (0.39 mmol) was converted into the title compound according to the procedure described for Example 13 (purification by subsequent preparative TLCs, eluent 2-98:2, then eluent3—9:1) in 6% yield. $^1$H NMR (300 MHz, CDCl$_3$): δ=1.99 (3H, s, Me), 2.30 (3H, s, Me), 2.63 (3H, s, Me), 6.98 (1H, s, Ar—H), 7.23-7.27 (2H, m, Ar—H), 7.51-7.60 (3H, m, Ar—H); [M+H]$^+$ (HPLC/MS): 330.05.

Example 46: 2-((dimethylamino)methyl)-3,6,9-trimethyl-5-phenyl-7H-furo[3,2-g]chromen-7-one 3,6,9-trimethyl-5-phenyl-7H-furo[3,2-g]chromen-7-one (Example 9, 2.3 mmol) was 2-chloromethylated according to the chloromethylation protocol described for Scheme 2 (conversion of e2 into h2), yielding 73% of 2-(chloromethyl)-3,6,9-trimethyl-5-phenyl-7H-furo[3,2-g]chromen-7-one after recrystallization of the precipitate from methanol. The latter (0.39 mmol) was converted into the title compound according to the procedure described for Example 15 (purification by repeated preparative TLC, eluent 2-95:5, then eluent3—9:1) in 18% yield. $^1$H NMR (300 MHz, CDCl$_3$): δ=1.97 (3H, s, Me), 2.07 (3H, s, Me), 2.30 (6H, s, NMe$_2$), 2.62 (3H, s, Me), 3.57 (2H, s, CH$_2$), 6.82 (1H, s, Ar—H), 7.23-7.28 (2H, m, Ar—H), 7.47-7.58 (3H, m, Ar—H); [M+H]$^+$ (HPLC/MS): 361.97.

Example 47: 4-methyl-8-phenyl-6H-chromeno[6,7-d]oxazol-6-one 6-amino-7-hydroxy-8-methyl-4-phenyl-2H-chromen-2-one was synthesized as described for Example 38 (cf. Scheme 7). Cyclization to give the title compound was achieved in 33% yield: 6-amino-7-hydroxy-8-methyl-4-phenyl-2H-chromen-2-one (y) (0.58 mmol; 1.0 eq.) was dissolved in DMF (1.5 mL) and pyridinium p-toluenesulfonate (0.15 eq.) and trimethyl orthoformate (1.7 e.) were added. The mixture was stirred at 60° C. for 90 min. Volatiles were evaporated under reduced pressure, the residue was dried in vacuo and purified via consecutive preparative TLCs (first: eluent2—95:5; second: eluent1—10:9:1). $^1$H NMR (300 MHz, CDCl$_3$): δ=2.66 (3H, s, Me), 6.36 (1H, s, Ar—H), 7.42-7.48 (2H, m, Ar—H), 7.50-7.55 (3H, m, Ar—H), 7.71 (1H, s, Ar—H), 8.12 (1H, s, Ar—H); [M+H]$^+$ (HPLC/MS): 278.05.

Example 48: 2,4,7-trimethyl-8-phenyl-6H-chromeno[6,7-d]oxazol-6-one

The synthesis of the starting material 7-hydroxy-3,8-dimethyl-4-phenyl-2H-chromen-2-one is described above as an intermediate in the synthesis of Example 9, which was obtained in 79% yield following SP-1A (4.0 to 8.0 mmol; crude product was filtered through a pad of silica gel, CH$_2$Cl$_2$ to eluent2—95:5). Further steps were performed in analogy to the synthetic procedure described for Example 38 (cf. Scheme 7):
a) 7-hydroxy-3,8-dimethyl-4-phenyl-2H-chromen-2-one (c2) (4.5 mmol) was nitrosilated to give 7-hydroxy-3,8-dimethyl-6-nitro-4-phenyl-2H-chromen-2-one in 24% yield;
b) The 6-nitro group was reduced to give 6-amino-7-hydroxy-3,8-dimethyl-4-phenyl-2H-chromen-2-one (y) using 0.1 eq. [Pd], reaction time 16 h. Crude product was purified by preparative TLC (eluent2—95:5); yield: 33%;
c) Cyclization with 1,1,1-trimethoxyethane gave the title compound in 23% yield. $^1$H NMR (300 MHz, CDCl$_3$): δ=1.99 (3H, s, Me), 2.61 (3H, s, Me), 2.62 (3H, s, Me), 7.06 (1H, s, Ar—H), 7.19-7.24 (2H, m, Ar—H), 7.44-7.55 (3H, m, Ar—H); [M+H]$^+$ (HPLC/MS): 306.06.

Example 49: 3,6,8-trimethyl-5-phenylfuro[2,3-b][1,8]naphthyridin-7(8H)-one

To a solution of 2-methoxy-6-methylaminopyridine (20 mmol, 1.0 eq.) in tetrahydrofuran (0.75 ml/mmol), N,N-diisopropylethylamine (1.5 eq.) was added at 0° C. To the reaction mixture a solution of propionyl chloride (1.5 eq.) in tetrahydrofuran (0.75 ml/mmol) was added dropwise over 20 minutes. The mixture was stirred at r.t. for 1 h. The suspension was filtered and the solid was washed with tetrahydrofuran. The filtrate was concentrated under reduced pressure. The crude residue was partitioned between CH$_2$Cl$_2$ and saturated aq. NaHCO$_3$ solution, the aqueous phase was extracted several times with CH$_2$Cl$_2$. The combined organic phases were dried over MgSO$_4$ and concentrated in vacuo. The crude residue was purified by Kugelrohr ("ball tube") vacuum distillation (boiling point: 180° C. at 5 mbar) to give N-(6-methoxypyridin-2-yl)-N-methylpropanamide as a yellow oil in 88% yield; $^1$H NMR (300 MHz, d6-DMSO): δ=0.99 (3H, t, CH$_3$), 2.33 (2H, q, CH$_2$), 3.24 (3H, s, NMe), 3.83 (3H, s, OMe), 6.71 (1H, d, Ar—H), 7.04 (1H, d, Ar—H), 7.77 (1H, t, Ar—H).

Lithiumdiisopropylamide solution (1.2 eq., 1.6 M in THF) in dry THF (1.5 mL/mmol) was cooled to −15° C., N-(6-methoxypyridin-2-yl)-N-methylpropanamide (15 mmol, 1.0 eq.) was dissolved in dry THF (2 mL/mmol) and added dropwise within 3 minutes under vigorous stirring in an inert atmosphere. The reaction mixture was stirred for additional 60 minutes at −15° C. Ethylbenzoate (1.2 eq.) was dissolved in THF (1.5 mL/mmol) and added dropwise within 15 minutes at −15° C. The mixture was allowed to warm to r.t. within 3 h and stirred at r.t. for additional 15 h, afterwards it was extracted with saturated aq. NH$_4$Cl and brine, dried over Na$_2$SO$_4$ and concentrated in vacuo. The resulting red-orange oil was crystallized from CH$_2$Cl$_2$/petroleum ether to give N-(6-methoxypyridin-2-yl)-N,2-dimethyl-3-oxo-3-phenylpropanamide as a pale yellow solid in 36% yield; $^1$H NMR (300 MHz, CDCl$_3$): δ=1.45 (3H, d, Me), 3.33 (3H, s, NMe), 3.88 (3H, s, OMe), 4.63 (1H, q, CH), 6.62 (1H, d, Ar—H), 6.78 (1H, d, Ar—H), 7.39 (2H, tt, Ar—H), 7.51 (1H, tt, Ar—H), 7.58 (1H, t, Ar—H), 7.86 (2H, dt, Ar—H).

N-(6-methoxypyridin-2-yl)-N,2-dimethyl-3-oxo-3-phenylpropanamide (5.2 mmol) was cyclized in 86% to 7-methoxy-1,3-dimethyl-4-phenyl-1,2-dihydro-1,8-naphthyridin-2-one according to SP-3A, 2$^{nd}$ step: reaction time 7 h; the reaction was quenched by dropwise addition of the mixture onto iced water. The resulting precipitated was filtered off, washed with aq. NaHCO$_3$ (5%), taken up in CH$_2$Cl$_2$/MeOH 95:5 and filtered again. The filtrate was dried over Na$_2$SO$_4$ and concentrated in vacuo; $^1$H NMR (300 MHz, CDCl$_3$): δ=2.01 (3H, s, Me), 3.90 (3H, s, NMe), 4.04 (3H, s, OMe), 6.47 (1H, d, Ar—H), 7.20 (2H, dt, Ar—H), 7.29 (1H, d, Ar—H), 7.40-7.54 (3H, m, Ar—H). 7-methoxy-1,3-dimethyl-4-phenyl-1,2-dihydro-1,8-naphthyridin-2-one (4.3 mmol, 1.0 eq.) was suspended in aq. HBr (37%; 5 mL/mmol) and cooled to 0° C. Bromine (1.1 eq.) was added dropwise. The reaction mixture was stirred 30 min at 0° C. and 2 h at 100° C., then cooled to r.t. The resulting precipitate was filtered off and washed with small quantities of MeOH to give 6-bromo-7-hydroxy-1,3-dimethyl-4-phenyl-1,8-naphthyridin-2(1H)-one as a pale orange solid in 93% yield; $^1$H NMR (300 MHz, d6-DMSO): δ=1.85 (3H, s, Me), 3.70 (3H, s, NMe), 7.28 (1H, s, Ar—H), 7.29 (2H, dt, Ar—H), 7.49-7.62 (3H, m, Ar—H). 6-bromo-7-hydroxy-1,3-dimethyl-4-phenyl-1,8-naphthyridin-2(1H)-one was converted into the title compound following SP-2C (3.5 mmol; 2$^{nd}$ step: reaction time 2 h, final purification by column chromatography, CH$_2$Cl$_2$/ethyl acetate—7:3) in 51% yield. $^1$H NMR (300 MHz, CDCl$_3$): δ=2.04 (3H, s, Me), 2.12 (3H, m, Me), 3.97 (3H, s, NMe), 7.24-7.28 (2H, m, Ar—H), 7.41 (1H, m, Ar—H), 7.49 (1H, s, Ar—H), 7.48-7.59 (3H, m, Ar—H); [M+H]$^+$ (HPLC/MS): 305.05.

Example 50: 3,9-dimethyl-5-phenyl-7H-chromeno[6,7-d]isoxazol-7-one

Starting material 7-hydroxy-8-methyl-4-phenyl-2H-chromen-2-one was synthesized as described above (intermediate in the synthesis of compound e1, Scheme 2), obtained in 75% yield from ethyl benzoylacetate and 2-methylresorcinol following SP-1A (50 mmol).

Further transformation of 7-hydroxy-8-methyl-4-phenyl-2H-chromen-2-one into the title compound was achieved in 16% yield according to SP-5B (2.0 mmol; preparative TLC, eluent2—100:1) and SP-5C (preparative TLC, eluent2—95:5). $^1$H NMR (300 MHz, CDCl$_3$): δ=2.51 (3H, s, Me), 2.67 (3H, s, Me), 6.35 (1H, s, Ar—H), 7.45-7.49 (2H, m, Ar—H), 7.51 (1H, s, Ar—H), 7.54-7.59 (3H, m, Ar—H); [M+H]$^+$ (HPLC/MS): 292.01.

Example 51: 3,9-dimethyl-5-phenylisoxazolo[4,5-g]quinolin-7(8H)-one

The synthesis of the starting material 7-hydroxy-8-methyl-4-phenylquinolin-2(1H)-one was achieved in 57% yield according SP-3A (16.2 mmol; final purification by washing the solid with CH$_2$Cl$_2$) starting from 3-amino-o-cresol and ethyl 2-methyl-3-oxo-3-phenyl-propanoate.

Further transformation of 7-hydroxy-8-methyl-4-phenylquinolin-2(1H)-one into the title compound was achieved in 14% yield according to SP-5B (1.6 mmol; preparative TLC, eluent2—95:5) and SP-5C (preparative TLC, eluent2—95:5). $^1$H NMR (300 MHz, CDCl$_3$): δ=2.51 (3H, s, Me), 2.72 (3H, s, Me), 6.64 (1H, s, Ar—H), 7.45-7.49 (2H, m, Ar—H), 7.53-7.60 (3H, m, Ar—H), 7.64 (1H, s, Ar—H), 10.01 (1H, br s, NH); [M+H]$^+$ (HPLC/MS): 291.06.

Example 52: 3,6,8,9-tetramethyl-5-phenylisoxazolo[4,5-g]quinolin-7(8H)-one

Starting material 7-hydroxy-1,3,8-trimethyl-4-phenylquinolin-2(1H)-one was synthesized as described above (intermediate in Example 34), 37% yield following SP-3A (4.37 mmol).

Further transformation of 7-hydroxy-1,3,8-trimethyl-4-phenylquinolin-2(1H)-one into the title compound according to SP-5B, yield 25% (0.9 mmol; preparative TLC 1$^{st}$ step eluent2—95:5; 2$^{nd}$ step eluent3—1:1) and SP-5C (prep. HPLC). $^1$H NMR (300 MHz, CDCl$_3$): δ=1.97 (3H, s, Me), 2.42 (3H, s, Me), 2.87 (3H, s, Me), 3.94 (3H, s, NMe), 7.10 (1H, s, Ar—H), 7.19-7.24 (2H, m, Ar—H), 7.47-7.58 (3H, m, Ar—H); [M+H]$^+$ (HPLC/MS): 318.94.

Example 53: 3,6,9-trimethyl-5-(pyridin-3-yl)-7H-furo[3,2-g]chromen-7-one

This compound was synthesized from ethyl 2-methyl-3-oxo-3-(pyridin-3-yl)propanoate and 2-methylresorcinol in 43% yield according to SP-1A (8.1 mmol; compound precipitated upon concentration of organic phases from extraction), followed by SP-1B-2 using 2.6 eq. chloroacetone (d2) (reaction time step 1=2 h, step 2=1 h; preparative TLC, eluent2—95:5, recrystallization from EtOH). $^1$H NMR (300 MHz, CDCl$_3$): δ=2.00 (3H, s, Me), 2.10 (3H, d, Me), 2.63 (3H, s, Me), 6.79 (1H, s, Ar—H), 7.43 (1H, m, Ar—H), 7.54 (1H, ddd, Ar—H), 7.66 (1H, dt, Ar—H), 8.58 (1H, dd, Ar—H), 8.80 (1H, dd, Ar—H); [M+H]$^+$ (HPLC/MS): 306.00.

Example 54: 3,6,9-trimethyl-5-(pyridin-3-yl)furo[3,2-g]quinolin-7(8H)-one

The building block 7-hydroxy-3,8-dimethyl-4-(pyridin-3-yl)quinolin-2(1H)-one was synthesized from ethyl 2-methyl-3-oxo-3-(pyridin-3-yl)propanoate and 3-amino-o-cresol in 95% yield according to SP-3A (8.1 mmol); heating in trans-decalin resulted already in nearly complete cyclization of the lactam unit. To achieve complete conversion, heating in TFA was applied according to SP-3A, 2$^{nd}$ step; upon removal of TFA, the oily residue was taken up in CH$_2$Cl$_2$ and crushed out by addition of diethyl ether.

Bromination of 7-hydroxy-3,8-dimethyl-4-(pyridin-3-yl)quinolin-2(1H)-one was achieved according to SP-3B in 65% yield (2.8 mmol): upon quenching and diluting with water, 6-bromo-7-hydroxy-3,8-dimethyl-4-(pyridin-3-yl)quinolin-2(1H)-one precipitated and was used as such after washing with small amounts of MeOH and drying in vacuo.

6-bromo-7-hydroxy-3,8-dimethyl-4-(pyridin-3-yl)quinolin-2(1H)-one was converted into the title compound in 11% yield via SP-3C (0.72 mmol; 2$^{nd}$ step: preparative TLC purification, eluent2—95:5). $^1$H NMR (300 MHz, CDCl$_3$): δ=2.02 (3H, s, Me), 2.09 (3H, d, Me), 2.62 (3H, s, Me), 6.89 (1H, s, Ar—H), 7.40 (1H, m, Ar—H), 7.53 (1H, ddd, Ar—H), 7.65 (1H, dt, Ar—H), 8.57 (1H, d, Ar—H), 8.79 (1H, dd, Ar—H), 9.20 (1H, br s, NH); [M+H]$^+$ (HPLC/MS): 305.00.

Example 55: 3,6,8,9-tetramethyl-5-(pyridin-3-yl)furo[3,2-g]quinolin-7(8H)-one

For the synthesis of building block 2-methyl-3-(methylamino)phenol, cf. Example 34.

The building block 7-hydroxy-1,3,8-trimethyl-4-(pyridin-3-yl)quinolin-2(1H)-one was synthesized from ethyl 2-methyl-3-oxo-3-(pyridin-3-yl)propanoate and 2-methyl-3-(methylamino)phenol in 55% yield according to SP-3A (4.0 mmol); heating in trans-decalin resulted already in (nearly) complete cyclization of the lactam unit. If small quantities of N-(3-hydroxy-2-methylphenyl)-N,2-dimethyl-3-oxo-3-(pyridin-3-yl)propanamide were still present, these were converted into the desired product by heating in TFA according to SP-3A, 2$^{nd}$ step; upon removal of TFA, the oily residue was taken up in CH$_2$Cl$_2$/MeOH 95:5 and crushed out by addition of diethyl ether.

Bromination of 7-hydroxy-1,3,8-trimethyl-4-(pyridin-3-yl)quinolin-2(1H)-one was achieved according to SP-3B in 76% yield (1.7 mmol): upon quenching and diluting with water, 6-bromo-7-hydroxy-1,3,8-trimethyl-4-(pyridin-3-yl)quinolin-2(1H)-one was extracted with ethyl acetate. This product was used as such without further purification steps. 6-bromo-7-hydroxy-1,3,8-trimethyl-4-(pyridin-3-yl)quinolin-2(1H)-one was converted into the title compound in 6% yield following SP-2C (0.70 mmol; purification after 1$^{st}$ step by preparative TLC, eluent2—95:5; final purification by preparative TLC, eluent2—95:5). 1H NMR (300 MHz, CDCl$_3$): δ=1.99 (3H, s, Me), 2.08 (3H, d, Me), 2.84 (3H, s, Me), 3.95 (3H, s, NMe), 6.85 (1H, s, Ar—H), 7.40 (1H, m, Ar—H), 7.55 (1H, ddd, Ar—H), 7.66 (1H, dt, Ar—H), 8.54 (1H, dd, Ar—H), 8.78 (1H, dd, Ar—H); [M+H]$^+$ (HPLC/MS): 319.11.

Example 56: 3,6,8,9-tetramethyl-5-(pyridin-3-yl)isoxazolo[4,5-g]quinolin-7(8H)-one The synthesis of building block 6-bromo-7-hydroxy-1,3,8-trimethyl-4-(pyridin-3-yl)quinolin-2(1H)-one is described for Example 55. 6-bromo-7-hydroxy-1,3,8-trimethyl-4-(pyridin-3-yl)quinolin-2(1H)-one was converted into the title compound in 8% yield following SP-5A (0.70 mmol; preparative TLC purification, eluent2—95:5) and SP-5C (preparative HPLC purification). $^1$H NMR (300 MHz, CDCl$_3$): δ=1.99 (3H, s, Me), 2.44 (3H, s, Me), 2.88 (3H, s, Me), 3.95 (3H, s, NMe), 6.97 (1H, s, Ar—H), 7.59 (1H, dd, Ar—H), 7.68 (1H, dt, Ar—H), 8.55 (1H, s, Ar—H), 8.81 (1H, d, Ar—H); [M+H]⁺ (HPLC/MS): 320.01.

Example 57: 3,9-dimethyl-5-(pyridin-2-yl)-7H-furo[3,2-g]chromen-7-one

This compound was synthesized from methyl 3-oxo-3-(pyridin-2-yl)propanoate and 2-methylresorcinol in 41% yield according to SP-1A (0.41 mmol), followed by SP-1B-1 using chloroacetone (d2). ¹H NMR (300 MHz, CDCl₃): δ=2.15 (3H, d, Me), 2.61 (3H, s, Me), 6.43 (1H, s, Ar—H), 7.44 (1H, m, Ar—H), 7.50 (1H, ddd, Ar—H), 7.53 (1H, s, Ar—H), 7.61 (1H, d, Ar—H), 7.94 (1H, td, Ar—H), 8.82 (1H, d, Ar—H).; [M+H]⁺ (HPLC/MS): 292.06.

Example 58: 3,9-dimethyl-5-(o-tolyl)-7H-furo[3,2-g]chromen-7-one

This compound was synthesized from ethyl 3-oxo-3-(o-tolyl)propanoate and 2-methylresorcinol in 7% yield according to SP-1A (4.0 mmol; preparative TLC, eluent2—95:5), followed by SP-1B-2 using 2.6 eq. chloroacetone (d2) (reaction time step 1=1 h, step 2=1 h; preparative TLC, eluent2—95:5). ¹H NMR (300 MHz, d6-DMSO): δ=2.06 (3H, d, Me), 2.13 (3H, s, Me), 2.55 (3H, s, Me), 6.30 (1H, s, Ar—H), 6.93 (1H, s, Ar—H), 7.29 (1H, dd, Ar—H), 7.38 (1H, td, Ar—H), 7.42 (1H, dd, Ar—H), 7.45 (1H, td, Ar—H), 7.88 (1H, d, Ar—H); [M+H]⁺ (HPLC/MS): 305.3.

Example 59: 3,6,8,9-tetramethyl-5-(o-tolyl)furo[3,2-g]quinolin-7(8H)-one

For the synthesis of building block 2-methyl-3-(methylamino)phenol, cf. Example 34.
The title compound was synthesized from 2-methyl-3-(methylamino)phenol (0.5 mmol) and methyl 2-methyl-3-(o-tolyl)-3-oxopropanoate according to SP-3 (SP-3A, 1ˢᵗ step: heating to 170° C. for 2.5 h under microwave irradiation; SP-3A, 2ⁿᵈ step: heating to 150° C. for 1 h under microwave irradiation; preparative TLC, eluent2—95:5; SP-3C, 1ˢᵗ step: heating to 100° C. for 1 h under microwave irradiation, partitioning between H₂O and CH₂Cl₂; SP-3C, 2ⁿᵈ step: reaction time 1 h, purification by preparative TLC, eluent2—95:5), overall yield 4%. ¹H NMR (300 MHz, CDCl₃): δ=1.92 (3H, s, Me), 2.02 (3H, s, Me), 2.06 (3H, d, Me), 2.85 (3H, s, Me), 3.97 (3H, s, NMe), 6.87 (1H, s, Ar—H), 7.07 (1H, d, Ar—H), 7.29-7.42 (4H, m, Ar—H); [M+H]⁺ (HPLC/MS): 332.3.

Example 60: 5-(2-chlorophenyl)-3,6,8,9-tetramethylfuro[3,2-g]quinolin-7(8H)-one

For the synthesis of building block 2-methyl-3-(methylamino)phenol, cf. Example 34.
The title compound was synthesized from 2-methyl-3-(methylamino)phenol (3.3 mmol) and methyl 3-(2-chlorophenyl)-2-methyl-3-oxopropanoate according to SP-3 (SP-3A: preparative TLC, eluent2—95:5; SP-3C, 1ˢᵗ step: reaction time 2 h, partitioning between H₂O and CH₂Cl₂; SP-3C, 2ⁿᵈ step: reaction time 1 h, purification by consecutive preparative TLC, eluent3—3:2 then eluent2—98:2), overall yield 1%. ¹H NMR (300 MHz, d6-DMSO): δ=1.80 (3H, s, Me), 2.01 (3H, d, Me), 2.83 (3H, s, Me), 3.87 (3H, s, NMe), 6.75 (1H, s, Ar—H), 7.35 (1H, m, Ar—H), 7.52-7.61 (2H, m, Ar—H), 7.71 (1H, m, Ar—H), 7.79 (1H, d, Ar—H); [M+H]⁺ (HPLC/MS): 352.3.

Example 61: 5-(2-fluorophenyl)-3,6,8,9-tetramethylfuro[3,2-g]quinolin-7(8H)-one

For the synthesis of building block 2-methyl-3-(methylamino)phenol, cf. Example 34.
The title compound was synthesized from 2-methyl-3-(methylamino)phenol (3.3 mmol) and ethyl 3-(2-fluorophenyl)-2-methyl-3-oxopropanoate according to SP-3 (SP-3A: preparative TLC, eluent2—95:5; SP-3C, 1ˢᵗ step: reaction time 2 h, partitioning between H₂O and CH₂Cl₂; SP-3C, 2ⁿᵈ step: reaction time 1 h, purification by consecutive preparative TLC, eluent3—3:2 then eluent2—98:2), overall yield 1%. ¹H NMR (300 MHz, d6-DMSO): δ=1.85 (3H, s, Me), 2.02 (3H, d, Me), 2.82 (3H, s, Me), 3.86 (3H, s, NMe), 6.89 (1H, s, Ar—H), 7.35 (1H, td, Ar—H), 7.40-7.48 (2H, m, Ar—H), 7.62 (1H, m_C, Ar—H), 7.79 (1H, d, Ar—H); [M+H]⁺ (HPLC/MS): 336.3.

Example 62: 5-(2-methoxypyridin-3-yl)-3,6,9-trimethyl-7H-furo[3,2-g]chromen-7-one This compound was synthesized from methyl 3-(2-methoxypyridin-3-yl)-2-methyl-3-oxopropanoate and 2-methylresorcinol in 5% yield according to SP-1A (4.0 mmol; preparative TLC, eluent2—95:5), followed by SP-1B-2 using 2.6 eq. chloroacetone (d2) (reaction time step 1=1 h, step 2=1 h; preparative TLC, eluent2—95:5). ¹H NMR (300 MHz, d6-DMSO): δ=1.83 (3H, s, Me), 2.07 (3H, d, Me), 2.54 (3H, s, Me), 3.83 (3H, s, OMe), 6.84 (1H, s, Ar—H), 7.25 (1H, dd, Ar—H), 7.73 (1H, dd, Ar—H), 7.85 (1H, d, Ar—H), 8.41 (1H, dd, Ar—H); [M+H]⁺ (HPLC/MS): 336.3.

Example 63: 5-(4-methoxypyridin-3-yl)-3,6,9-trimethyl-7H-furo[3,2-g]chromen-7-one This compound was synthesized from methyl 3-(4-methoxypyridin-3-yl)-2-methyl-3-oxopropanoate and 2-methylresorcinol in 2% yield according to SP-1A (2.0 mmol; preparative TLC, eluent2—95:5), followed by SP-1B-2 using 2.6 eq. chloroacetone (d2) (reaction time step 1=2 h, consecutive preparative TLC, eluent3—3:2 then eluent2—95:5; step 2=1 h; preparative TLC, eluent2—95:5). ¹H NMR (300 MHz, d6-DMSO): δ=1.84 (3H, s, Me), 2.07 (3H, d, Me), 2.54 (3H, s, Me), 3.82 (3H, s, OMe), 6.84 (1H, s, Ar—H), 7.34 (1H, d, Ar—H), 7.85 (1H, d, Ar—H), 8.31 (1H, s, Ar—H), 8.67 (1H, d, Ar—H); [M+H]⁺ (HPLC/MS): 336.2.

Example 64: 5-(2-methoxypyridin-3-yl)-3,6,8,9-tetramethylfuro[3,2-g]quinolin-7(8H)-one For the synthesis of building block 2-methyl-3-(methylamino)phenol, cf. Example 34.
The title compound was synthesized from 2-methyl-3-(methylamino)phenol (3.6 mmol) and methyl 3-(2-methoxypyridin-3-yl)-2-methyl-3-oxopropanoate according to SP-3 (SP-3A: preparative TLC, eluent2—95:5; SP-3C, 1ˢᵗ step: reaction time 2 h, partitioning between H₂O and CH₂Cl₂; SP-3C, 2ⁿᵈ step: reaction time 1 h, purification by preparative TLC, eluent3—3:2), overall yield 1%. ¹H NMR (300 MHz, d6-DMSO): δ=1.80 (3H, s, Me), 2.03 (3H, d, Me), 2.82 (3H, s, Me), 3.78 (3H, s, OMe), 3.85 (3H, s, NMe), 6.84 (1H, s, Ar—H), 7.21 (1H, dd, Ar—H), 7.64 (1H, dd, Ar—H), 7.78 (1H, d, Ar—H), 8.37 (1H, dd, Ar—H); [M+H]⁺ (HPLC/MS): 349.3.

Patch-Clamp Assay for Inhibitory Activity on Kv1.3

For a description of a Kv1.3 patch-clamp assay, see Grissmer et al., *Mol. Pharmacol.* 1994, 45, 1227; whole cell patch-clamp recording was performed with n≥2 individual experiments at each compound concentration using different cells. Three or more different concentrations were determined per dose response curve. $IC_{50}$ as calculated therefrom is shown in Table 1.

TABLE 1

Activity range of specific compounds of the invention on Kv1.3

| Ex | Structure | $IC_{50}$ |
|---|---|---|
| 1 | 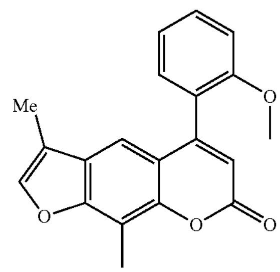 [SMILES: COc1ccccc1-c1cc(=O)oc2c(C)c3occ(C)c3cc12] | +++ |
| 2 | 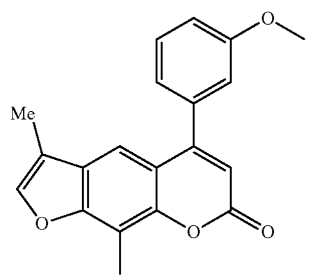 [SMILES: COc1cccc(-c2cc(=O)oc3c(C)c4occ(C)c4cc23)c1] | + |
| 3 | 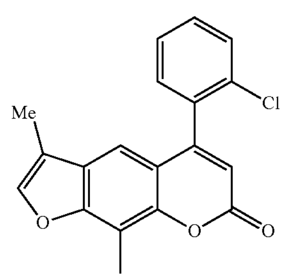 [SMILES: Cc1coc2c(C)c3oc(=O)cc(-c4ccccc4Cl)c3cc12] | + |
| 4 | 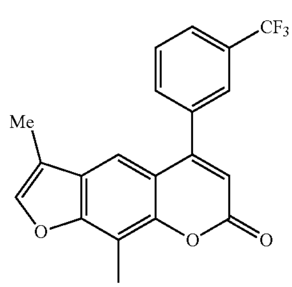 [SMILES: Cc1coc2c(C)c3oc(=O)cc(-c4cccc(C(F)(F)F)c4)c3cc12] | + |
| 5 | 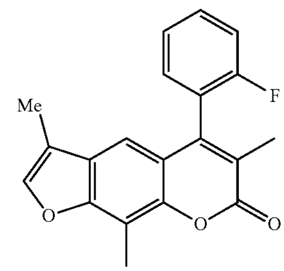 [SMILES: Cc1c(-c2ccccc2F)c2cc3c(C)coc3c(C)c2oc1=O] | +++ |
| 6 | 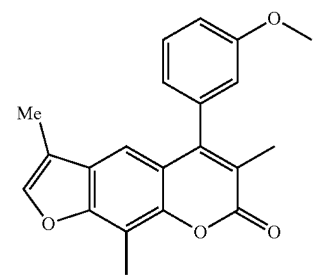 [SMILES: COc1cccc(-c2c(C)c(=O)oc3c(C)c4occ(C)c4cc23)c1] | ++ |
| 7 | 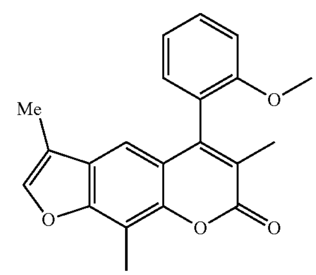 [SMILES: COc1ccccc1-c1c(C)c(=O)oc2c(C)c3occ(C)c3cc12] | +++ |
| 8 | 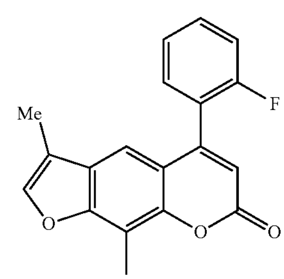 [SMILES: Cc1coc2c(C)c3oc(=O)cc(-c4ccccc4F)c3cc12] | +++ |
| 9 | 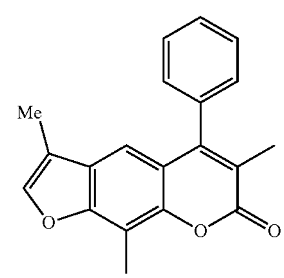 [SMILES: Cc1c(-c2ccccc2)c2cc3c(C)coc3c(C)c2oc1=O] | +++ |

TABLE 1-continued

Activity range of specific compounds of the invention on Kv1.3

| Ex | Structure | IC$_{50}$ |
|---|---|---|
| 10 | | +++ |
| 11 | | +++ |
| 12 | | + |
| 13 | | + |
| 14 | | + |
| 15 | 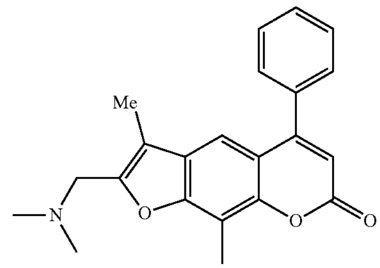 [SMILES: Cc1c(CN(C)C)oc2c(C)c3oc(=O)cc(-c4ccccc4)c3cc12] | + |
| 16 | 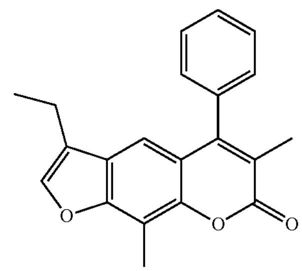 [SMILES: CCc1coc2c(C)c3oc(=O)c(C)c(-c4ccccc4)c3cc12] | +++ |
| 17 | 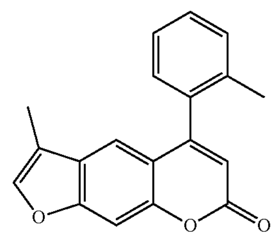 [SMILES: Cc1ccccc1-c1cc(=O)oc2cc3occ(C)c3cc12] | ++ |
| 18 | 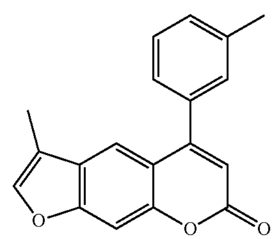 [SMILES: Cc1cccc(-c2cc(=O)oc3cc4occ(C)c4cc23)c1] | ++ |
| 19 | 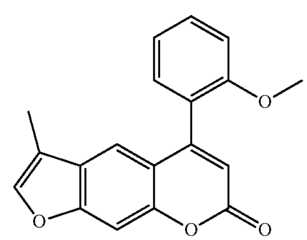 [SMILES: COc1ccccc1-c1cc(=O)oc2cc3occ(C)c3cc12] | ++ |
| 20 | 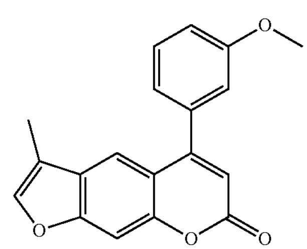 [SMILES: COc1cccc(-c2cc(=O)oc3cc4occ(C)c4cc23)c1] | ++ |

TABLE 1-continued

Activity range of specific compounds of the invention on Kv1.3

| Ex | Structure | IC$_{50}$ |
|---|---|---|
| 21 | 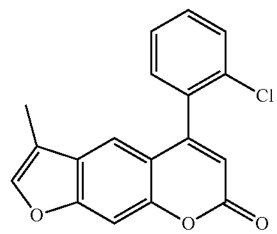 [SMILES: Cc1coc2cc3oc(=O)cc(-c4ccccc4Cl)c3cc12] | ++ |
| 22 | 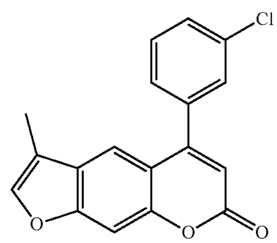 [SMILES: Cc1coc2cc3oc(=O)cc(-c4cccc(Cl)c4)c3cc12] | ++ |
| 23 | 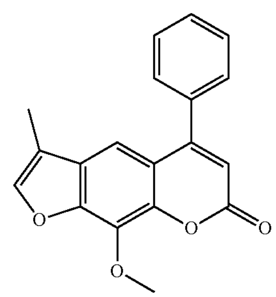 [SMILES: COc1c2occ(C)c2cc2c(-c3ccccc3)cc(=O)oc12] | + |
| 24 | 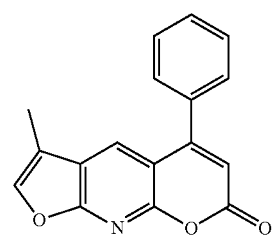 [SMILES: Cc1coc2nc3oc(=O)cc(-c4ccccc4)c3cc12] | ++ |
| 25 | 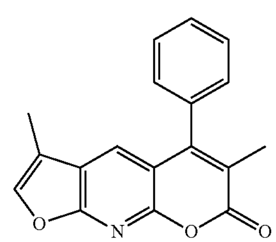 [SMILES: Cc1c(-c2ccccc2)c2cc3c(C)coc3nc2oc1=O] | +++ |
| 26 | 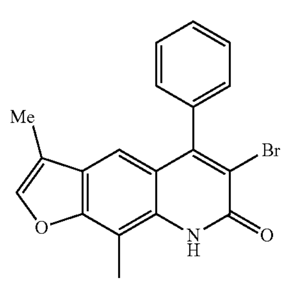 [SMILES: Cc1coc2c(C)c3[nH]c(=O)c(Br)c(-c4ccccc4)c3cc12] | +++ |
| 27 | | ++ |
| 28 | | ++ |
| 29 | | + |
| 59 | | ++ |
| 61 | | +++ |

TABLE 1-continued

Activity range of specific compounds of the invention on Kv1.3

| Ex | Structure | IC$_{50}$ |
|---|---|---|
| 63 | 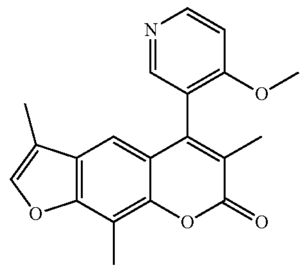 [SMILES: COc1ccncc1-c1c(C)c(=O)oc2c(C)c3occ(C)c3cc12] | + |
| 30 | 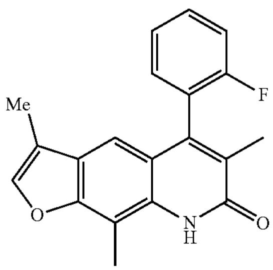 [SMILES: Cc1c(-c2ccccc2F)c2cc3c(C)coc3c(C)c2[nH]c1=O] | +++ |
| 31 | 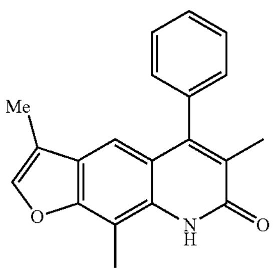 [SMILES: Cc1c(-c2ccccc2)c2cc3c(C)coc3c(C)c2[nH]c1=O] | +++ |
| 32 | 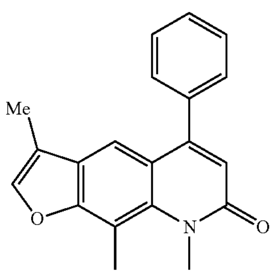 [SMILES: Cc1coc2c(C)c3c(cc12)c(-c1ccccc1)cc(=O)n3C] | + |
| 33 | 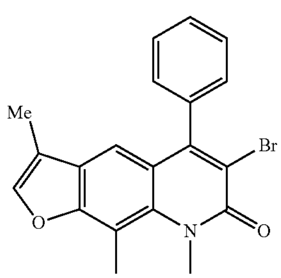 [SMILES: Cc1coc2c(C)c3c(cc12)c(-c1ccccc1)c(Br)c(=O)n3C] | +++ |

TABLE 1-continued

Activity range of specific compounds of the invention on Kv1.3

| Ex | Structure | IC$_{50}$ |
|---|---|---|
| 34 | 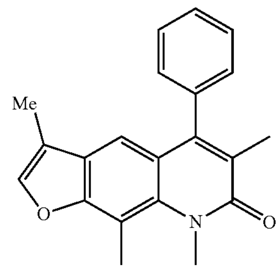 [SMILES: Cc1c(-c2ccccc2)c2cc3c(C)coc3c(C)c2n(C)c1=O] | +++ |
| 35 | 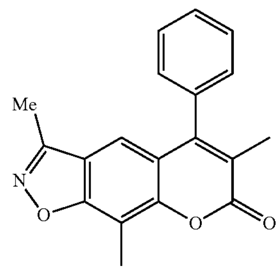 [SMILES: Cc1c(-c2ccccc2)c2cc3c(C)noc3c(C)c2oc1=O] | ++ |
| 36 | 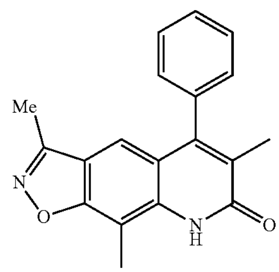 [SMILES: Cc1c(-c2ccccc2)c2cc3c(C)noc3c(C)c2[nH]c1=O] | +++ |
| 37 | 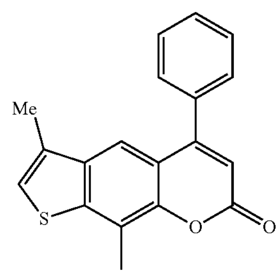 [SMILES: Cc1csc2c(C)c3oc(=O)cc(-c4ccccc4)c3cc12] | ++ |
| 38 | 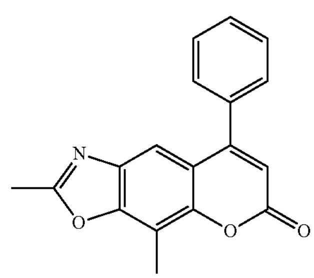 [SMILES: Cc1nc2cc3c(-c4ccccc4)cc(=O)oc3c(C)c2o1] | ++ |

TABLE 1-continued

Activity range of specific compounds of the invention on Kv1.3

| Ex | Structure | IC$_{50}$ |
|---|---|---|
| 39 | 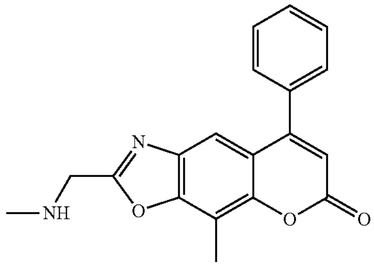 [SMILES: CNCc1nc2cc3c(-c4ccccc4)cc(=O)oc3c(C)c2o1] | + |
| 40 | 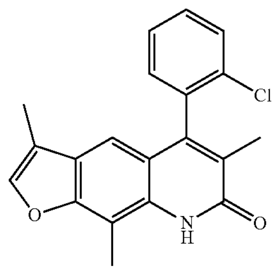 [SMILES: Cc1c(-c2ccccc2Cl)c2cc3c(C)coc3c(C)c2[nH]c1=O] | +++ |
| 41 | 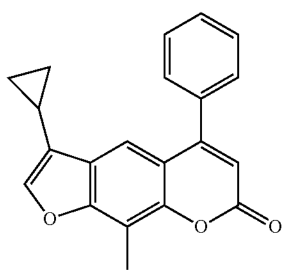 [SMILES: Cc1c2oc(=O)cc(-c3ccccc3)c2cc2c(C3CC3)coc12] | +++ |
| 42 | 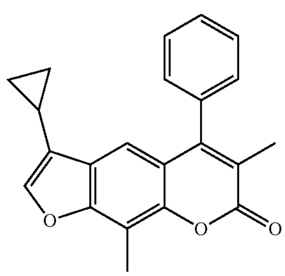 [SMILES: Cc1c(-c2ccccc2)c2cc3c(C4CC4)coc3c(C)c2oc1=O] | ++ |
| 43 | 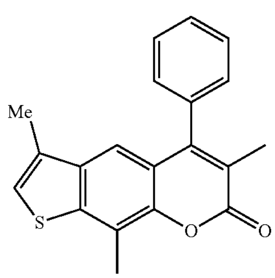 [SMILES: Cc1c(-c2ccccc2)c2cc3c(C)csc3c(C)c2oc1=O] | +++ |
| 44 | | + |
| 45 | | + |
| 46 | | + |
| 47 | | + |
| 48 | | ++ |

TABLE 1-continued

Activity range of specific compounds of the invention on Kv1.3

| Ex | Structure | IC$_{50}$ |
|---|---|---|
| 49 | 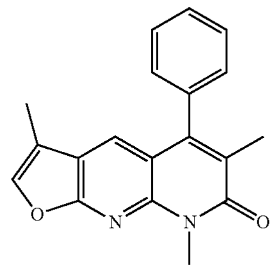 [SMILES: Cc1c(-c2ccccc2)c2cc3c(C)coc3nc2n(C)c1=O] | +++ |
| 50 | 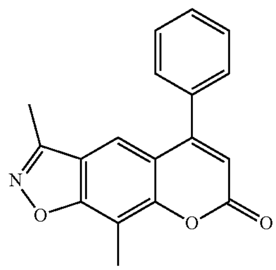 [SMILES: Cc1noc2c(C)c3oc(=O)cc(-c4ccccc4)c3cc12] | + |
| 51 | 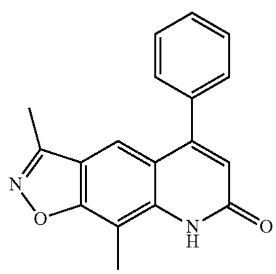 [SMILES: Cc1noc2c(C)c3[nH]c(=O)cc(-c4ccccc4)c3cc12] | ++ |
| 52 | 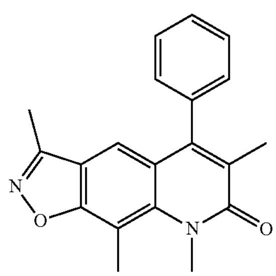 [SMILES: Cc1c(-c2ccccc2)c2cc3c(C)noc3c(C)c2n(C)c1=O] | ++ |
| 53 | 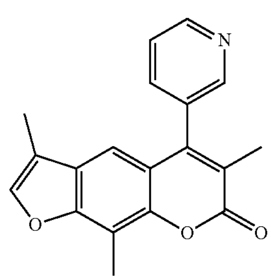 [SMILES: Cc1c(-c2cccnc2)c2cc3c(C)coc3c(C)c2oc1=O] | +++ |
| 54 | | +++ |
| 55 | | ++ |
| 56 | | + |
| 57 | | + |
| 58 | | ++ |

TABLE 1-continued

Activity range of specific compounds of the invention on Kv1.3

| Ex | Structure | IC$_{50}$ |
|---|---|---|
| 60 | 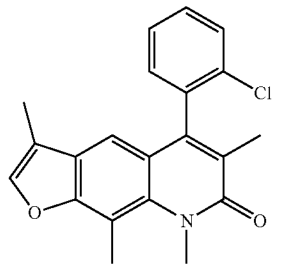 [SMILES: Cc1c(-c2ccccc2Cl)c2cc3c(C)coc3c(C)c2n(C)c1=O] | +++ |
| 62 | 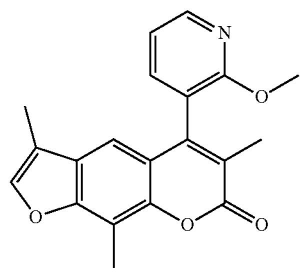 [SMILES: COc1ncccc1-c1c(C)c(=O)oc2c(C)c3occ(C)c3cc12] | ++ |
| 64 | 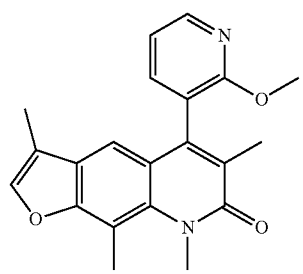 [SMILES: COc1ncccc1-c1c(C)c(=O)n(C)c2c(C)c3occ(C)c3cc12] | + |

Patch-clamp IC$_{50}$(Kv1.3) values:

\+ = 1501-3000 nM;

++ = 501-1500 nM;

+++ ≤500 nM

Note that examples 26-34, 36, 40, 49, 51, 52, 54-56, 59-61 and 64 are not part of the present invention and serve as illustrative examples.

T Cell Proliferation Assay (in Analogy to *Bioorg. Med. Chem. Lett.* 2009, 19, 2299)

Peripheral blood mononuclear cells (PBMC) from healthy human donors were isolated by centrifugation over a density gradient in an aqueous solution, comprising a high molecular weight polysaccharide and sodium diatrizonate, and having a density of 1.077±0.001 (Ficoll-Hypaque by Sigma-Aldrich, Germany; according to manufacturer's instructions). Purified PBMC were washed twice with PBS and resuspended in RPMI1640 culture medium (Gibco-Life Technologies) supplemented with 10% heat inactivated fetal calf serum, 1.5 mM L-glutamine, 100 U penicillin/ml, and 100 mg streptomycin/ml (all from PAA-GE Healthcare). For stimulation, PBMC were seeded at 1×10$^5$ cells/well, incubated with TRAM-34 (5 μM) and the test compounds for 4 h and activated with 50 ng/ml anti-CD3 (from eBioscience). After 48 hours proliferation was measured using a BrdU based cell proliferation ELISA according to the manual. IC$_{50}$ as calculated therefrom is shown in Table 2.

TABLE 2

Activity range of specific compounds of the invention within the T-cell assay

| Example | IC$_{50}$(BrdU) |
|---|---|
| 1 | + |
| 5 | ++ |
| 7 | ++ |
| 9 | +++ |
| 10 | +++ |
| 11 | ++ |
| 16 | +++ |
| 25 | ++ |
| 26 | +++ |
| 30 | ++ |
| 31 | +++ |
| 34 | ++ |
| 37 | + |
| 40 | +++ |
| 41 | ++ |
| 43 | ++ |
| 49 | + |
| 53 | ++ |
| 54 | + |
| 55 | + |

IC$_{50}$(BrdU incorporation):

\+ = 3.1-15.0 μM;

++ = 1.3-3.0 μM;

+++ ≤1.2 μM

Note that Examples 26-34, 40, 49, 54 and 55 are not part of the present invention and serve as illustrative examples.

Pristane-Induced Arthritis (PIA) Model:

Arthritis was induced in female Dark Agouti rats by intradermal injection of 150 μL/rat pristane into the base of the tail on DAY0, according to Vingsbo et al., Am. J. Pathol. 1996, 149, 1675. Compound treatment was started on DAY16 and continued until DAY30, dosing Example 53 at 60 mg/kg, p.o., sid, and Example 34 at 45 mg/kg, p.o., bid, each in a lipophilic formulation. As a positive control, methotrexate (MTX) was dosed i.p., sid, with 0.05 mg/kg, also starting DAY16. Arthritis development was monitored daily by a macroscopic scoring system for the four limbs ranging from 0 to 4 (0=no visible effects of arthritis; 1=edema and/or erythema of one digit; 2=edema and/or erythema of two joints; 3=edema and/or erythema of more than two joints; 4=severe arthritis of the entire paw and digits, associated with ankylosis and deformity of the paw.), resulting in an Arthritic Index (AI) reflecting the sum of scores of all 4 limbs per rat (maximum AI=16). Both treatment regimens resulted in significant amelioration of arthritis as illustrated in FIG. 1.

Disease induction in saline-treated and vehicle-treated control animals reached a maximum of AI around 14. MTX-treatment resulted in a disease stabilization around AI=8.7 (p=0.001). Treatment with Example 53 decreased the AI down to around 10.4 (p=0.01) and with Example 34 down to AI around 9.1 (p<0.001).

BRIEF DESCRIPTION OF DRAWINGS

FIG. 1 illustrates the results for the Pristane-induced arthritis (PIA) model.

The invention claimed is:

1. A compound of formula (II) or a pharmaceutically acceptable salt or solvate thereof,

II wherein
$A^1$ is C—$R^8$;
$A^2$ is C—$R^3$;
$A^3$ is N;
$A^4$ and $A^5$ and $A^6$ are independently N or C—$R^1$;
$R^1$ is hydrogen, ($C_1$-$C_3$)alkyl, halogen, ($C_1$-$C_3$)alkoxy, or ($C_1$-$C_3$)haloalkyl;
$R^2$ is hydrogen, halogen, or ($C_1$-$C_3$)alkyl;
$R^3$ is hydrogen, ($C_1$-$C_3$)alkyl, $NR^4R^5$, ($C_1$-$C_3$)alkyl-$NR^4R^5$, or cyano,
$R^4$ and $R^5$ are independently hydrogen, ($C_3$-$C_5$)cycloalkyl, ($C_3$-$C_5$)heterocycloalkyl or ($C_1$-$C_3$)alkyl, or $R^4$ and $R^5$ together with the nitrogen atom to which they are attached form a 5- to 7-membered heterocyclic ring optionally comprising in addition to the aforementioned nitrogen atom a further heteroatom, which is O or $NR^6$,
$R^6$ is hydrogen, methyl, acetyl or formyl;
Y is O; and
$R^8$ is ($C_1$-$C_4$)alkyl, ($C_3$-$C_5$)cycloalkyl or ($C_3$-$C_5$)heterocycloalkyl.

2. The compound according to claim 1 or a pharmaceutically acceptable salt or solvate thereof, wherein
$R^1$ is hydrogen, methyl, chloro, fluoro, methoxy, ethoxy or trifluoromethyl;
$R^2$ is hydrogen, bromo or methyl;
$R^3$ is hydrogen, methyl, morpholinyl, morpholinomethyl, N-methylaminomethyl, N,N-dimethylaminomethyl or cyano; and
$R^8$ is methyl, ethyl or cyclopropyl.

3. The compound according to claim 1 or a pharmaceutically acceptable salt or solvate thereof, wherein
$R^2$ is hydrogen or methyl; and
$R^3$ is hydrogen, morpholinyl, morpholinomethyl, N,N-dimethylaminomethyl or cyano.

4. The compound according to claim 1 or a pharmaceutically acceptable salt or solvate thereof, wherein
at least one of the following conditions is fulfilled:
1) $R^2$ is halogen, or
2) $R^3$ is $NR^4R^5$ or cyano, or
3) $A^4$ or $A^5$ or $A^6$ is N.

5. The compound according to claim 1 or a pharmaceutically acceptable salt or solvate thereof, wherein
one of $A^4$ and $A^5$ and $A^6$ is N and the others are N or C—$R^1$.

6. The compound according to claim 1 or a pharmaceutically acceptable salt or solvate thereof, wherein
$R^8$ is methyl; $R^1$ is hydrogen or methoxy;
$R^2$ is hydrogen or methyl; and
$R^3$ is hydrogen, methyl or N-methylaminomethyl.

7. A compound selected from:
3-methyl-5-phenyl-7H-furo[2,3-b]pyrano[3,2-e]pyridin-7-one,
3,6-dimethyl-5-phenyl-7H-furo[2,3-b]pyrano[3,2-e]pyridin-7-one,
or a pharmaceutically acceptable salt or solvate thereof.

8. A pharmaceutical composition comprising the compound according to claim 1 and a pharmaceutically acceptable carrier or diluent.

9. The compound according to claim 1 or a pharmaceutically acceptable salt thereof.

10. The compound according to claim 7 or a pharmaceutically acceptable salt thereof.

11. The compound according to claim 7, which is

12. The compound according to claim 1, wherein each of $A^4$ and $A^5$ and $A^6$ are C—$R^1$.

13. The compound according to claim 12, wherein each $R^1$ is H.

14. The compound according to claim 1, wherein $R^2$ is halogen.

15. The compound according to claim 1, wherein $R^3$ is $NR^4R^5$ or cyano.

16. The compound according to claim 1, wherein $R^8$ is methyl and $R^3$ is methyl.

* * * * *